(12) United States Patent
Aboody et al.

(10) Patent No.: US 10,426,801 B2
(45) Date of Patent: Oct. 1, 2019

(54) ENCAPSULATED DIAGNOSTICS AND THERAPEUTICS IN NANOPARTICLES—CONJUGATED TO TROPIC CELLS AND METHODS FOR THEIR USE

(71) Applicant: CITY OF HOPE, Duarte, CA (US)

(72) Inventors: Karen Aboody, Duarte, CA (US); Alexander Annala, Duarte, CA (US); Rachael Mooney, Duarte, CA (US); Jacob Berlin, Duarte, CA (US); Yiming Weng, Duate, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 14/256,777

(22) Filed: Apr. 18, 2014

(65) Prior Publication Data
US 2015/0056144 A1    Feb. 26, 2015

Related U.S. Application Data

(63) Continuation of application No. PCT/US2012/060916, filed on Oct. 18, 2012.

(60) Provisional application No. 61/548,668, filed on Oct. 18, 2011.

(51) Int. Cl.
| | |
|---|---|
| *A61K 35/30* | (2015.01) |
| *A61K 49/08* | (2006.01) |
| *A61K 31/4188* | (2006.01) |
| *A61K 47/51* | (2017.01) |
| *A61K 47/69* | (2017.01) |

(52) U.S. Cl.
CPC .......... *A61K 35/30* (2013.01); *A61K 31/4188* (2013.01); *A61K 47/51* (2017.08); *A61K 47/6901* (2017.08); *A61K 47/6923* (2017.08); *A61K 47/6929* (2017.08); *A61K 49/085* (2013.01)

(58) Field of Classification Search
None
See application file for complete search history.

(56) References Cited

U.S. PATENT DOCUMENTS

| | | |
|---|---|---|
| 7,598,335 B2 | 10/2009 | Wang et al. |
| 7,625,764 B2 | 12/2009 | Stayton et al. |
| 2010/0055167 A1 * | 3/2010 | Zhang ............ A61K 9/0085 424/450 |
| 2010/0190257 A1 | 7/2010 | Salem et al. |
| 2011/0027239 A1 | 2/2011 | Paek |
| 2011/0034753 A1 | 2/2011 | Dobson et al. |
| 2011/0206740 A1 | 8/2011 | Karp et al. |

FOREIGN PATENT DOCUMENTS

| | | | |
|---|---|---|---|
| WO | WO2009134866 | * | 11/2009 |
| WO | WO 2010028087 | * | 3/2010 |
| WO | WO2010059253 | * | 5/2010 |
| WO | WO2011047277 | * | 4/2011 |
| WO | WO-2011/056685 A1 | | 5/2011 |
| WO | WO 2013/079105 | * | 6/2013 |

OTHER PUBLICATIONS

Song et al., "Labeling Efficacy of Superparamagnetic Iron Oxide Nanoparticles to Human Neural Stem Cells; Comparison of Ferumoxides, Monocrystalline Iron Oxide, Cross-linked Iron Oxide (CLIO)-NH2 and tat-CLIO", Korean J Radiol, 2007, vol. 8, No. 5, pp. 365-371.*
Laquitana et al., "New Strategies to deliver anticancer drugs to brain tumors", Expert Opin Drug Deliv, 2009, vol. 6, No. 10, pp. 1017-1032.*
Sperling et al., "Biological applications of gold nanoparticles", Chemical Society Reviews, 2008, vol. 37, pp. 1896-1908.*
Liu et al., "Highly Sensitive, Colorimetric Detection of Mercury(II) in Aqueous Media by Quaternary Ammonium Group-Capped Gold Nanoparticles at Room Temperature", Analytical Chemistry, 2010, vol. 82, pp. 9606-9610.*
Chittasupho, Chuda, "Targeting of nanoparticles to cell adhesion molecules for potential immune therapy", KU ScholarWorks, Dec. 10, 2010, pp. i-viii, pp. 1-200. (Year: 2010).*
Aboody, K.S., et al., "Neural Stem Cells Display Extensive Tropism for Pathology in Adult Brain: Evidence from Intracranial Gliomas," Proc. Natl. Acad. Sci. USA 97(23):12846-12851 (2000).
Aboody, K.S., et al., "Targeting of Melanoma Brain Metastases Using Engineered Neural Stem/Progenitor Cells," Neuro-Oncology 8:119-126 (2006).
Aboody, K.S., et al., "Translating Stem Cell Studies to the Clinic for CNS Repair: Current State of the Art and the Need for a Rosetta Stone," Neuron 70(4):597-613 (2011).
Acharya S., et al., "PLGA Nanoparticles Containing Various Anti-cancer Agents and Tumour Delivery by EPR Effect," Advanced Drug Delivery Reviews Mar. 2011.
Allard, E., et al., "Convection-Enhanced Delivery of Nanocarriers for the Treatment of Brain Tumors," Biomaterials Apr. 2009;30(12):2302-18, Epub Jan. 24, 2009 (2009).

(Continued)

*Primary Examiner* — Laura Schuberg
(74) *Attorney, Agent, or Firm* — Mintz, Levin, Cohn, Ferris Glovsky and Popeo, P.C.

(57) ABSTRACT

A therapeutic or diagnostic delivery vehicle is provided. The delivery vehicle may include one or more particles, such as microparticles, nanoparticles and stimuli-responsive particles, conjugated to a tropic cell that targets at least one pathological entity or site. In addition, a pharmaceutical composition is provided. The pharmaceutical composition may include, among other things, a particle conjugated to a tropic cell such as those discussed above and at least one diagnostic or therapeutic agent, such as those described herein. In some aspects, the tropic cell may target at least one pathological entity or site. Further, methods for diagnosing, monitoring or treating a pathological condition in a subject are provided. Such methods may include administering a therapeutically effective amount of the pharmaceutical composition to a subject.

6 Claims, 45 Drawing Sheets

(56) References Cited

OTHER PUBLICATIONS

Allard, E., et al., "188Re-Loaded Lipid Nanocapsules as a Promising Radiopharmaceutical Carrier for Internal Radiotherapy of Malignant Gliomas," Eur J Nucl Med Mol Imaging. Oct. 2008;35(10):1838-46. Epub May 9, 2008.
Alon, R., et al., "Cell adhesion to streptavidin via RGD-dependent integrins," Eur J Cell Biol. Feb;60(1):1-11 (1993).
Arbab A.S., et al., "Labeling of Cells with Ferumoxides-Protamine Sulfate Complexes does not Inhibit Function or Differentiation Capacity of Hematopoietic or Mesenchymal Stem Cells," NMR Biomed. 18: 553-559 (2005).
Arbab A.S., et al., "Comparison of Transfection Agents in Forming Complexes With Ferumoxides Cell Labeling Efficiency, and Cellular Viability," Mol Imaging. 3: 24-32 (2004).
Aryal, S., et al., "Polymer-Cisplatin Conjugate Nanoparticles for Acid-Responsive Drug Delivery," ACS Nano. 4(1):251-258 (2010).
Barth R.F, "Brain Tumor Models in Experimental Neurooncology: The 9L, C6, T9, F98, RG2, D74, RT-2, and CNS-1 Gliomas," Journal of Neruooncology; 36: 91-102 (1998).
Bobola, M.S., et al., "Role of O6-Methylguanine-DNA Methyltransferase in Resistance of Human Brain Tumor Cell Lines to the Clinically Relevant Methylating Agents Temozolomide and Streptozotocin," Clin. Cancer Res. 2:735-741 (1996).
Brady, M.L., et al., "Pathways of Flow for Infusions into Putamen," http://kineticsfoundation.org/wp-content/uploads/2012/06/PutamenInfusions20120415.pdf, pp. 1-17.
Brown, A.B., et al., "Intravascular Delivery of Neural Stem Cell Lines to Target Intracranial and Extracranial Tumors of Neural and Non-Neural Origin," Hum Gene Ther. Dec. 10, 2003;14(18):1777-85.
Brownell, G.L., et al., "Quantitative Dynamic Studies Using Short-Lived Radioisotopes and Positron Detection," Proceedings of the Symposium on Dynamic Studies with Radioisotopes in Medicine, Rotterdam. IAEA. Vienna. 161 (1970).
Bryant S. et al., "Properties Influence ECM Production by Chondrocytes Photoencapsulated in Poly(Ethylene Glycol) Hydrogels," J. Biomed. Mater. Res. 59: 63-72 (2002).
Burke, A.R., et al., "The Resistance of Breast Cancer Stem Cells to Conventional Hyperthermia and their Sensitivity to Nanoparticle-mediated Photothermal Therapy," Biomaterials. 33(10):2961-2970 (2012).
Carare, R.O., et al., "Solutes, but not Cells, Drain from the Brain Parenchyma Along Basement Membranes of Capillaries and Arteries: Significance for Cerebral Amyloid Angiopathy and Neuroimmunology," Neuropathology and Applied Neurobiology 34:131-144 (2008).
Castro, M.G. et al., "Current and Future Strategies for the Treatment of Malignant Brain Tumors," Pharmacol. Ther; 98: 71-108 (2003).
Chakraborty, S., et al., "Contrasting Effect of Gold Nanoparticles and Nanorods with Different Surface Modifications on the Structure and Activity of Bovine Serum Albumin," Langmuir, 27 (12), 7722-7731 (2011).
Chen, J., et al., "Immuno Gold Nanocages with Tailored Optical Properties for Targeted Photothermal Destruction of Cancer Cells," Nano Lett. 7(5):1318-1322 (2007).
Chen, M.Y., et al., "Surface Properties, More Than Size, Limiting Convective Distribution of Virus-Sized Particles and Viruses in the Central Nervous System," J Neurosurg, Aug;103(2):311-9 (2005).
Cheng, H., et al., "Nanoparticulate Cellular Patches for Cell-Mediated Tumoritropic Delivery," ACS Nano. 4(2):625-631 (2010).
Christofk, H., et al., "The M2 Splice Isoform of Pyruvate Kinase is Important for Cancer Metabolism and Tumour Growth," Nature. 452: 230-233 (2008).
Claes, A., et al., "Diffuse Glioma Growth: a Guerilla War," Acta Neuropathol. 114:443-458 (2007).
Clapper, J., et al., "Biotinylated Biodegradable Nanotemplated Hydrogel Networks FOR Cell Interactive Applications," Biomacromolecules 9: 1188-1194. (2008).
Cole, J.R., et al., "Photothermal Efficiencies of Nanoshells and Nanorods for Clinical Therapeutic Applications," The Journal of Physical Chemistry C, 113 (28), 12090-12094 (2009).
Connor, E. E., et al., "Gold Nanoparticles are Taken up by Human Cells but do not Cause Acute Cytotoxicity," Small, 1 (3), 325-327(2005).
Cowen, R.L., et al., "Adenovirus Vector—Mediated Delivery of the Prodrug-Converting Enzyme Carboxypeptidase G2 in a Secreted or GPIAnchored form: High-Level Expression of this Active Conditional Cytotoxic Enzyme at the Plasma Membrane," Cancer Gene Therapy 9:897-907 (2002).
Cui, W., et al., "Photosensitive Nanoparticles of Chitosan Complex for Controlled Release of Dye Molecules," Nanotechnology, 22, 065702 (2011).
Daniel, M.C., et al., "Gold Nanoparticles: Assembly, Supramolecular Chemistry, Quantum-Size-Related Properties, and Applications Toward Biology, Catalysis, and Nanotechnology," Chem Rev, 104 (1), 293-346 (2004).
Danks, M.K., et al., "Tumor-Targeted Enzyme/Prodrug Therapy Mediates Long-Term Disease-Free Survival of Mice Bearing Disseminated Neuroblastoma," Cancer Res. 67:22-25 (2007).
Decuzzi, P., et al., "Size and Shape Effects in the Biodistribution of Intravascularly Injected Particles," Journal of Controlled Release. 141(3): p. 320-327 (2010).
Deeken, J.F., et al., "The Blood-Brain Barrier and Cancer: Transporters, Treatment, and Trojan Horses," Clin. Cancer Res. 13:1663-1674 (2007).
Desanknai, S., et al., "Local Tumor Irradiation Enhances the Anti-Tumor Effect af a Double-Suicide Gene Therapy System in a Murine Glioma Model," The Journal of Gene Medicine; 5: 377-385 (2003).
Ehtesham, M., et al., "Induction of Glioblastoma Apoptosis Using Neural Stem Cell-Mediated Delivery of Tumor Necrosis Factor-Related Apoptosis-Inducing Ligand," Cancer Res. 62:7170-7174 (2002).
Ehtesham, M., et al., "The Use of Inteleukin 12-Secreting Neural Stem Cells for the Treatment of Intracranial Glioma," Cancer Res. 62:5663 (2002).
Ehtesham, M., et al., "Use of Neural Stem Cells as Therapeutic Vehicles for the Treatment of Malignant Glioma," Expert Rev. Neurotherapeutics 3(6), 883-895 (2003).
Elias, M.C., et al., "TWIST is Expressed in Human Gliomas and Promotes Invasion," Neoplasia 7(9):824-837 (2005).
El-Sayed, I.H., et al., "Selective Laser Photo-Thermal Therapy of Epithelial Carcinoma Using Anti-EGFR Antibody Conjugated Gold Nanoparticles," Cancer Letters, 239 (1), 129-135 (2006).
Eseonu, C., "Intracranial Drug Delivery of siRNA Nanoparticles to Tumor Cells. ProQuest Dissertations and Theses," Biomedical engineering (2011).
Eskandary, H., et al., "The Role of Stem Cells in Tumor Targeting and Growth Suppression of Gliomas," Biologics: Targets and Therapy 5:61-70 (2011).
Fang, J., et al., "The EPR Effect: Unique Features of Tumor Blood Vessels for Drug Delivery, Factors Involved, and Limitations and Augmentation of the Effect," Adv Drug Deliv Rev. Mar. 18m 2011;63(3):136-51. Epub May 2, 2010.
Fay, F., et al., "Antibody-Targeted Nanoparticles for Cancer Therapy," Immunotherapy, 3 (3), 381-394 (2011).
Fernandez, A.M., et al., "Calcineurin in Reactive Astrocytes Plays a Key Role in the Interplay Between Proinflammatory and Anti-Inflammatory Signals," The Journal of Neuroscience; 27:8745-8756 (2007).
Flax, J.D., et al., "Engraftable Human Neural Stem Cells Respond to Developmental Cues, Replace Neurons, and Express Foreign Genes," Nat Biotechnol.Nov. 1998;16(11):1033-9.
Flexman, J.A., et al., "Quantitative Analysis of Neural Stem Cell Migration and Tracer Clearance in the Rat Brain by MRI," Mol Imaging Biol. Feb. 2011;13(1):104-11.
Frank, J,A., et al., "Clinically Applicable Labeling of Mammalian and Stem Cells by Combining Superparamagnetic Iron Oxides and Transfection Agents," Radiology, 228, 480 (2003).

(56) References Cited

OTHER PUBLICATIONS

Frank, R.T., et al, "Neural Stem Cells as a Novel Platform for Tumor-Specific Delivery of Therapeutic Antibodies," PLoS ONE, 4 (12), e8314 (2009).
Fukui, T., et al., "Intracellular Delivery of Nanogel-Quantum Dot Hybrid Nanoparticles Into Human Periodontal Ligament Cells," Drug Metab Lett, 1(2):131-5 (2007).
Fukumori, Y., et al., "Nanoparticles for cancer therapy and diagnosis," Adv Poweder Technol. 17: 1-28 (2002).
Fulford, L.G., et al., "Specific Morphological Features Predictive for the Basal Phenotype in Grade 3 Invasive Ductal Carcinoma of Breast," Histopathology, 49 (1), 22-34 (2006).
Furnari, F.B., et al., "Malignant Astrocytic Glioma: Genetics, Biology, and Paths to Treatment," Genes and Development; 21: 2683-2710 (2007).
Gao, W., et al., "ph-Responsive Nanoparticles for Drug Delivery," Molecular Pharmaceutics.7:1913-1920 (2010).
Gennet, N., et al., "Microspheres as a Vehicle for Biomolecule Delivery to Neural Stem Cells," N Biotechnol. Sep. 2009;25(6):442-9. Epub Jun. 11, 2009.
Glangchai, L., et al., "Nanoimprint Lithography Based Fabrication of Shape-Specific, Enzymatically-Triggered Smart Nanoparticles," Journal of Controlled Release. 125: 263-272 (2008).
Glass, R., et al, "Glioblastoma-Induced Attraction of Endogenous Neural Precursor Cells is Associated with Improved Survival," The Journal of Neuroscience; 25: 2637-2646 (2005).
Grabinski, C., et al., "Effect of Gold Nanorod Surface Chemistry on Cellular Response," ACS Nano, 5 (4), 2870-2879 (2011).
Greish, K., "Enhanced Permeability and Retention (EPR) Effect for Anticancer Nanomedicine Drug Targeting," Methods Mol Biol, 624,25-37 (2010).
Guichard S., et al., "Conversion of the CPT-11 Metabolite APC to SN-38 by Rabbit Liver Carboxylesterase," Clinical Cancer Research. 4: 3089-3094. (1998).
Gullotti, E., et al., "Extracellularly Activated Nanocarriers: A New Paradigm of Tumor Targeted Drug Delivery," Mol. Pharm. 6: 1041-1051 (2009).
Guo, P., et al., "Up-Regulation of Angiopoietin-2, Matrix Metalloprotease-2, Membrane Type 1 Metalloprotease, and Laminin 5 Gamma 2 Correlates with the Invasiveness of Human Glioma," Am J Pathol, 166,877 (2005).
Gutova, M., et al., "Neural Stem Cell-Mediated CE/CPT-11 Enzyme/Prodrug Therapy in Transgenic Mouse Model of Intracerebellar Medulloblastoma," Gene Ther (2012).
Haiyan, C., et al., "Characterization of pH- and Temperature-Sensitive Hydrogel Nanoparticles for Controlled Drug Release," PDA Journal of Pharmaceutical Science and Technology. 61, 303, (2007).
Hansen, K., et al., "A 3-Dimensional Extracellular Matrix as a Delivery System for the Transplantation of Glioma-Targeting Neural Stem/Progenitor Cells," Neuro Oncol. Jul. 2010;12(7):645-54. Epub Feb. 14, 2010.
Harrington, K.J., et al., "Biodistribution and Pharmacokinetics of 111 In-DTPA-Labelled Pegylated Liposomes in a Human Tumour Xenograft Model: Implications for Novel Targeting Strategies," British journal of cancer, 83 (2), 232-238 (2000).
Hirsch, L.R., et al., "Nanoshell-Mediated Near-Infrared Thermal Therapy of Tumors Under Magnetic Resonance Guidance," Proc Natl Acad Sci U S A, 100 (23), 13549-13554 (2003).
Holden, C.A., et al., "Surface Engineering of Macrophages with Nanoparticles to Generate a Cell—Nanoparticle Hybrid Vehicle for Hypoxia-Targeted Drug Delivery," International Journal of Nanomedicine:5 25-36 (2010).
Holmberg, A., et al., "The Biotin-Streptavidin Interaction Can be Reversibly Broken Using Water at Elevated Temperatures," Electrophoresis. Feb. 2005;26(3):501-10.
Holzapfel, V., et al., "Preparation of Fluorescent Carboxyl and Amino Functionalized Polystyrene Particles by Miniemulsion Polymerization as Markers for Cells," Macromolecular Chemistry and Physics, 2005. 206(24): p. 2440-2449.
Huang, X., et al., "Plasmonic Photothermal Therapy (PPTT) Using Gold Nanoparticles," Lasers Med Sci, 23 (3), 217-228 (2008).
Huff, T.B., et al., "Hyperthermic Effects of Gold Nanorods on Tumor Cells," Nanomedicine (Lond), 2 (1), 125-132 (2007).
Ignatova, T.N., et al., "Human Cortical Glial Tumors Contain Neural Stem-Like Cells Expressing Astroglial and Neuronal Markers in Vitro," Glia; 39:193-206 (2002).
Ikawa M., et al., "Generation of Transgenic Mice Using Lentiviral Vectors: A Novel Preclinical Assessment of Lentiviral Vectors for Gene Therapy," Molecular Therapy; 4: 666-673 (2003).
Iyer, A.K., et al., "Exploiting the Enhanced Permeability and Retention Effect for Tumor Targeting," Drug Discov Today. 11: 812-818. (2006).
Jackson, J.S., et al., "Homing of Stem Cells to Sites of Inflammatory Brain Injury after Intracerebral and Intravenous Administration: A Longitudinal Imaging Study," Stem Cell Res Ther. Jun. 15, 2010;1(2):17.
Jain, A., et al., "Transferrin-Appended Pegylated Nanoparticles for Temozolomide," Journal of Microencapsulation, 28, 21 (2011).
Jain, R.K., et al.,"Stylianopoulos, Delivering Nanomedicine to Solid Tumors," Nat Rev Clin Oncol. Nov. 2010;7(11):653-64. Epub Sep. 14, 2010.
Jain, R., "Delivery of Molecular and Cellular Medicine to Solid Tumors," Adv. Drug Deliv. Rev. 46: 149-168 (2001).
James, W., et al., "Application of INAA to the Build-Up and Clearance of Gold Nanoshells in Clinical Studies in Mice," Journal of Radioanalytical and Nuclear Chemistry, 271 (2), 455-459 (2007).
Johnson, R.M., et al., "Therapeutic Applications of Cell-Penetrating Peptides. Cell-Penetrating Peptides: Methods and Protocols," Methods in Molecular Biology, 683: DOI 10.1007/978-1-60761-919-2_38 (2011).
Jolesz, F.A, "MRI-Guided Focused Ultrasound Surgery," Annu Rev Med 60, 417-430 (2009).
Karp, J.M., et al., "The Devil Is in the Details," Cell stem cell, 4(3): p. 206-216 (2009).
Kelly, K.L., et al., "The Optical Properties of Metal Nanoparticles: The Influence of Size, Shape, and Dielectric Environment," The Journal of Physical Chemistry B, 107 (3), 668-677(2002).
Kendall, S.E., et al., "Neural Stem Cell Targeting of Glioma Is Dependent on Phosphoinositide 3-Kinase Signaling," Stem Cells, 26(6): p. 1575-1586 (2008).
Kim, S.U., et al., Production of Immortalized Human Neural Crest Stem Cells. Methods, Mol Biol, 198, 55-65 (2002).
Kim. S.U., et al., "Human Neural Stem Cells Genetically Modified for Brain Repair in Neurological Disorders," Neuropathology, 24 (3), 159-171 (2004).
Kim, M., et al., "pH-Responsive PEG-Poly(betaamino ester) Block Copolymer Micelles with a Sharp Transition," Macromol. Rapid Commun. 27: 447-451 (2006).
Kim. S.K., et al., "Human Neural Stem Cells Target Experimental Intracranial Medulloblastoma and Deliver a Therapeutic Gene Leading to Tumor Regression," Clinical Cancer Research, 12 (18), 5550-5556 (2006).
Kim. S.U., et al., "Production and Characterization of Immortal Human Neural Stem Cell Line with Multipotent Differentiation Property," Methods Mol Biol, 438:103-21(2008).
Kim, J.H., et al., "Stereological Analysis on Migration of Human Neural Stem Cells in the Brain of Rats Bearing Glioma," Neurosurgery, Feb;66(2):333-42; discussion 342 (2010).
Kim, D.S. et al., "Highly Pure and Expandable PSA-NCAM-Positive Neural Precursors from Human ESC and Ipsc-Derived Neural Rosettes," PLoS ONE. 7(7): p. e39715 (2011).
King, G.D., et al., "Gene Therapy and Targeted Toxins for Glioma," Current Gene Therapy, 5: 535-557 (2005).
Kraitchman, D., et al., "In Vivo Magnetic Resonance Imaging of Mesenchymal Stem Cells in Myocardial Infarction," Circulation, 10: 2290-2293 (2003).
Krauze, M.T., et al., "Reflux-Free Cannula for Convection-Enhanced High-Speed Delivery of Therapeutic Agents," J Neurosurg. Nov. 2005;103(5):923-9.
Krishnamachari, Y., et al., "Self-Assembly of Cell—Microparticle Hybrids. Advanced Biomaterials," 20: 989-993 (2008).

(56) References Cited

OTHER PUBLICATIONS

Krishnamachari, Y., et al., "Innovative Strategies for Co-Delivering Antigens and Cpg Oligonucleotides," Adv Drug Deliv Rev: 61 205-217 (2009).
Krystofiak, E.S., et al., "Elimination of Tumor Cells Using Folate Receptor Targeting by Antibody-Conjugated, Gold-Coated Magnetite Nanoparticles in a Murine Breast Cancer Model," Journal of Nanomaterials, p. 9 (2012).
Kunwar, S., "Convection Enhanced Delivery of the LI13-PE38QQR for Treatment of Recurrent Malignant Glioma: Presentation of Interim Findings from Ongoing Phase 1 Studies," Acta Neurochir Suppl; 88: 105-111 (2003).
Kvols, L.K., "Radiation Sensitizers: A Selective Review of Molecules Targeting DNA and non-DNA Targets," Journal of Nuclear Medicine, 46: 187s (2005).
Laske, D.W., et al., "Tumor Regression with Regional Distribution of the Targeted Toxin TF-CRM107 in Patients with Malignant Brain Tumors," Nature Medicine; 3: 1362-1368 (1997).
Levin, V.A., et al., "Sucrose and Inulin Space Measurements of Cerebral Cortex in Four Mammalian Species," Am J Physiol. Nov. 1970;219(5):1528-33.
Li, L., et al., "Silica Nanorattle-Doxorubicin-Anchored Mesenchymal Stem Cells for Tumor-Tropic Therapy," ACS Nano, 5 (9), 7462-7470 (2011).
Lin, D., et al., "Novel Method for Visualizing and Modeling the Spatial Distribution of Neural Stem Cells within Intracranial Glioma," Neuroimage. 2007;37 Suppl 1:S18-26. Epub May 13, 2007 (2007).
Link, S., et al., "Spectral Properties and Relaxation Dynamics of Surface Plasmon Electronic Oscillations in Gold and Silver Nanodots and Nanorods," The Journal of Physical Chemistry B, 103 (40), 8410-8426 (1999).
Liu, Y., et al., "Synthesis, Stability, and Cellular Internalization of Gold Nanoparticles Containing Mixed Peptide-Poly(Ethylene Glycol) Monolayers," Anal Chem, 79 (6), 2221-2229 (2007).
Lorenz, M.R., et al., "Synthesis of Fluorescent Polyisoprene Nanoparticles and Their Uptake into Various Cells," Macromol Biosci, Aug. 11;8(8):711-27 (2008).
Lorenz, M.R. et al., "Uptake of Functionalized, Fluorescent-Labeled Polymeric Particles in Different Cell Lines and Stem Cells," Biomaterials. May 2006;27(14):2820-8. Epub Jan. 23, 2006.
Love, Z., et al., "Imaging of Mesenchymal Stem Cell Transplant by Bioluminiescence and PET," J Nucl Med. 48: 2011-2020 (2007).
Macewan, S., et al., "Stimulus-Responsive Macromolecules and Nanoparticles for Cancer Drug Delivery," Nanomedicine. 5:793-806 (2010).
Mackay, J.A., et al., "Distribution in Brain of Liposomes after Convection Enhanced Delivery; Modulation by Particle Charge, Particle Diameter, and Presence of Steric Coating," Brain Research, 1035(2): p. 139-153 (2005).
MacLauren, D.C., et al., "PET Imaging of Transgene Expression," Biol Psychiatry. 48: 337-348 (2000).
Mailander, V., et al., "Interaction of Nanoparticles with Cells," Biomacromolecules, 10(9): p. 2379-2400 (2009).
Malugin, A., et al., "Cellular Uptake and Toxicity of Gold Nanoparticles in Prostate Cancer Cells: A Comparative Study of Rods and Spheres," J Appl Toxicol, 30 (3), 212-217(2010).
Marumoto, T., et al., "Novel Mouse Glioma Model: Cell-Type and Region Specific Activation of Oncogenes Using Lentiviral Vectors," Nature Protocols; DOI: 10.1038/nprot.2008.207 (2008).
Mayer-Proschel, M., et al., "Isolation of Lineage-Restricted Neuronal Precursors from Multipotent Neuroepithelial Stem Cells," Neuron; 19: 773-785 (1997).
McBain, S.C., et al., "Magnetic Nanoparticles for Gene and Drug Delivery," Int J Nanomedicine. 3, 169-180, (2008).
Meikle, S.R., et al., "Pharmacokinetic Assessment of Novel Anti-Cancer Drugs Using Spectral Analysis and Positron Emission Tomography: A Feasibility Study," Cancer Chemotherapy and Pharmacology, 42(3): p. 183-193 (1998).
Meyer, D.L., et al., "Reduced Antibody Response to Streptavidin through Site-Directed Mutagenesis," Protein Sci., Mar;10(3):491-503 (2001).
Mirza, A.N., et al., "Radiofrequency Ablation of Solid Tumors," Cancer J., 7 (2), 95-102 (2001).
Moon J., et al., "Synthetic Biomimetic Hydrogels Incorporated with Ephrin-A1 for Therapeutic Angiogenesis," Biomacromolecules. 8: 42-49, (2007).
Mooney, R., et al., "Neural Stem Cells Improve Intracranial Nanoparticle Retention and Tumor-Selective Distribution," Future Oncol., 10(3), 401-415, (2014).
Mooney, R., et al., "Conjugation of pH-responseive Nanoparticles to Neural Stem Cells Improves Intratumoral Theraphy," Journal of Controlled Release, 8 pgs. (2014).
Muller, F.J., et al., "Gene Therapy: Can Neural Stem Cells Deliver?" Nature Reviews; 7: 75-84 (2006).
Murphy, C.J., et al., "Anisotropic Metal Nanoparticles: Synthesis, Assembly, and Optical Applications," J Phys Chem B, 109 (29), 13857-13870 (2005).
Neeves, K.B., et al., "Dilation and Degradation of the Brain Extracellular Matrix Enhances Penetration of Infused Polymer Nanoparticles," Brain Res. Nov. 14, 2007;1180:121-32. Epub Aug. 29, 2007.
Neuberger, T., et al., "Superparamagnetic Nanoparticles for Biomedical Applications: Possibilities and Limitations of a New Drug Delivery System," J Magn Magn Mater. 293: 483-496 (2005).
Niidome, T., et al., "PEG-Modified Gold Nanorods with a Stealth Character for in Vivo Applications," J Control Release, 114 (3), 343-347 (2006).
Niidome, Y., et al., "Surface Modification of Gold Nanorods with Synthetic Cationic Lipids," Chem Commun (Camb), (36), 3777-3779 (2007).
Paciotti, G.F., et al., "Colloidal Gold Nanoparticles: A Novel Nanoparticle Platform for Developing Multifunctional Tumor-Targeted Drug Delivery Vectors," Drug Development Research, 67 (1), 47-54 (2006).
Panyam, J., et al., "Biodegradable Nanoparticles for Drug and Gene Delivery to Cells and Tissue," Adv Drug Deliv Rev; 55: 329-47 (2003).
Pardridge, W.M., "Blood-Brain Barrier Drug Targeting Enables Neuroprotection in Brain Ischemia Following Delayed Intravenous Administration of Neurotrophins," adame Curie Bioscience Database Austin (TX): Landes Bioscience; 2000-2011, Landes Bioscience and Springer Science+Business Media, 2002 pp. 397-430.
Parkin, D.M., et al., "Global cancer statistics," Cancer Journal for Clinicians; 55:74-108 (2002).
Patil, R., et al., "Temozolomide Delivery to Tumor Cells by a Multifunctional Nano Vehicle Based on Poly(B-L-Malic Acid)," Pharm Res, 11, 2317, (2010).
Peer, D., et al., "Nanocarriers as an Emerging Platform for Cancer Therapy," Nat Nano, 2 (12), 751-760 (2007).
Penas-Prado, M., et al., "Moleculary Targeted Therapies for Malignant Gliomas: Advances and Challenges," Expert Review of Anti-Cancer Therapy; 7: 641-661 (2007).
Peppas, N., et al., "Physiochemical Foundations and Structural Design of Hydrogels in Medicine and Biology," Annu. Rev. Biomed. Eng. 2:9-29. (2000).
Perlstein, B., et al., "Convection-Enhanced Delivery of Maghemite Nanoparticles: Increased Efficacy and MRI Monitoring," Neuro Oncol. Apr. 2008;10(2):153-61. Epub Mar. 3, 2008.
Petersen, M.A., et al., "Diverse Microglial Motility Behaviors During Clearance of Dead Cells in Hippocampal Slices," Glia. Apr. 15, 2004;46(2):195-206.
Pfenninger, C.V., et al., "CD133 Is Not Present on Neurogenic Astrocytes in the Adult Subventricular Zone, but on Embryonic Neural Stem Cells, Ependymal Cells, and Glioblastoma Cells," Cancer Research; 6: 5727-5736 (2007).
Philipp, C.M., et al., Nd:YAG Laser Procedures in Tumor Treatment, Semin Surg Oncol, 11 (4), 290-298 (1995).
Pollenzi, A., et al., "Gene Transfer by Lentiviral Vectors Is Limited by Nuclear Translocation and Rescued by HIV-1 Pol Sequences," Nature Genetics; 25: 217-222 (2000).

(56) References Cited

OTHER PUBLICATIONS

Prayson, R., "Cyclooxygenase-2 (COX-2) Expression by Immunohistochemistry in Glioblastoma Multiforme," Annals of Diagnostic Pathology; 6: 148-153 (2002).
Prescher, J.A., et al., "Chemical Remodeling of Cell Surfaces in Living Animals," Nature; 430: 873-877 (2004).
Prudhomme, M., et al., "Interstitial Diode Laser Hyperthermia in the Treatment of Subcutaneous Tumor," Lasers Surg Med, 19 (4), 445-450 (1996).
Rebner, K., et al., "Dark-Field Scattering Microscopy for Spectral Characterization of Polystyrene Aggregates," Opt Express. Feb. 1, 2010;18(3):3116-27. doi: 10.1364/OE.18.003116.
Rejman J., et al., "Size-Dependent Internalization of Particles via the Pathways of Clathrin-and Caveolae-Mediated Endocytosis," Biochem J. Jan. 1, 2004;377(Pt 1):159-69.
Roger, M., et al., "Mesenchymal Stem Cells as Cellular Vehicles for Delivery of Nanoparticles to Brain Tumors," Biomaterials, 31 (32), 8393-8401 (2010).
Saito, R., et al., "Convection-Enhanced Delivery of Tumor Necrosis Factor-Related Apoptosis-Inducing Ligand with Systemic Administration of Temozolomide Prolongs Survival in an Intracranial Glioblastoma Xenograft Model," Cancer Research; 64: 6858-6862 (2004).
Sampson, J.H., et al., "Progress Report of a Phase I Study of The Intracerebral Microinfusion of a Recombinant Chimeric Protein Composed of Transforming Growth Factor Alpha and a Mutated Form of the Pseudomonas Exotoxin Termed PE-38 for the Treatment of Malignant Brain Tumors," J Neurooncol; 65: 27-35 (2003).
Sanai, N., et al., "Neural Stem Cells and the Origins of Gliomas," New England Journal of Medicine; 353:811-822 (2005).
Sawhney, A.S., et al., "Bioerodable Hydrogels Based on Photopolymerized Poly(Ethylene Glycol)-Co-Poly(Alpha-Hydroxy Acid) Diacryalte Macromers," Macromolecules, 26: 581-587. (1993).
Schafer, R., et al., "Labeling of Human Mesenchymal Stromal Cells with Superparamagnetic Iron Oxide Leads to a Decrease in Migration Capacity and Colony Formation Ability," Cytotherapy. 11:68-78. (2009).
Schafer R., et al., "Transferrin Receptor Upregulation: In Vitro Labeling of Rat Mesenchymal Stem Cells with Superparamagnetic Iron Oxide," Radiology. 244: 514-523. (2007).
Schluep, T., et al., "Pharmacokinetics and Tumor Dynamics of the Nanoparticle IT-101 From PET Imaging and Tumor Histological Measurements," Proc Natl Acad Sci. 106: 11394-11399. (2009).
Schmidt, N.O., et al., "Brain Tumor Tropism of Transplanted Human Neural Stem Cells is Induced by Vascular Endothelial Growth Factor," Neoplasia: 7:623-629 (2005).
Schnarr, K., et al., "Gold Nanoparticle-Loaded Neural Stem Cells for Photothermal Ablation of Cancer," Adv. Healthcare Mater, 7 pages, (2013).
Seki, T., et al., "Percutaneous Microwave Coagulation Therapy for Patients with Small Hepatocellular Carcinoma: Comparison with Percutaneous Ethanol Injection Therapy," Cancer, 85 (8), 1694-1702 (1999).
Seneterre, E., et al., "Detection of Hepatic Metastases: Ferumoxides-Enhanced MR Imaging Versus Unenhanced MR Imaging and CT During Arterial Portography," Radiology, 200,785, (1996).
Shubayev, V.I., et al., ". Magnetic Nanoparticles for Theragnostics," Adv Drug Deliv Rev. 61:467-477. (2009).
Singh, J.P., "Enabling Technologies for Homing and Engraftment of Cells for Therapeutic Applications," J Am Coll Cardiol Intv, 2,803, (2009).
Singh, S.K., et al., "Identification of Brain Tumor Initiating Cells," Nature; 432: 396-401 (2004).
Soderquist, R., et al., "Release of Plasmid DNA-Encoding IL-10 From PLGA Microparticles Facilitates Long-Term Reversal of Neuropathic Pain Following a Single Intrathecal Administration," Pharmaceutical Research. 27: 841-854. (2010).
Srinivas L., et al., "Preferential Oxidation of Cell Surface Sialic Acid by Periodate Leads to Promotion of Transformation in JB6 Cells," Carcinogenesis Apr;5(4):515-9 (1984).
Stephan, M.T., et al., "Therapeutic Cell Engineering with Surface-Conjugated Synthetic Nanoparticles," Nature Medicine:16:1035-1041 (2010).
Stephan, M. T., et al., ", Enhancing Cell Therapies from the Outside in: Cell Surface Engineering Using Synthetic Nanomaterials," Nano Today. Jun. 1, 2011;6(3):309-325 (2011).
Stuart C.M, et al., "Magnetic Nanoparticles for Gene and Drug Delivery," Int J Nanomedicine. 3, 169-180, (2008).
Stupp, R., et al., "Radiotherapy Plus Concomitant and Adjuvant Temozolomide for Glioblastoma," New England Journal of Medicine; 352: 987-996 (2005).
Sykov, E., et al., "Diffusion in Brain Extracellular Space," Physiological Reviews 88(4): p. 1277-1340 (2008).
Tang, C., et al., "Concise Review: Nanoparticles and Cellular Carriers-Allies in Cancer Imaging and Cellular Gene Therapy?" Stem Cells: Translational and Clinical Research. 28: 1686-1702. (2010).
Tang, Y., et al., "In Vivo Tracking of Neural Progenitor Cell Migration to Glioblastomas," Hum Gene Ther. Sep. 1, 2003;14(13):1247-54.
Thu, M., et al., Iron Labeling and Pre-Clinical MRI Visualization of Therapeutic Human Neural Stem Cells in a Murine Glioma Model, PloS ONE, Iron-Labeled NSC and MRI4: e7218. (2009).
Tong, L., et al., "Gold Nanorods Mediate Tumor Cell Death by Compromising Membrane Integrity," Adv Mater, 19, 3136-3141 (2007).
Van Der Zee, J., "Heating the Patient: A Promising Approach?" Ann Oncol, 13 (8), 1173-1184 (2002).
Vaupel, P., "Tumor Microenvironmental Physiology and Its Implications for Radiation," Oncology Semin. Radiat. Oncol. 14: 198-206. (2004).
Vavra, M., et al., "Comparative Pharmacokinetics of 14C-Sucrose in RG-2 Rat Gliomas after Intravenous and Convection-Enhanced Delivery," Neuro-oncology; 6:104-112 (2004).
Verma, M., et al., "Effect of Surface Properties on Nanoparticle-Cell Interactions," Small. Jan. 2010;6(1):12-21.
Von Maltzahn, G., et al., "Computationally Guided Photothermal Tumor Therapy Using Long-Circulating Gold Nanorod Antennas," Cancer Research, 69 (9), 3892-3900 (2009).
Weber, F.W., et al., "Local Convection Enhanced Delivery of IL4-Pseudomonas Exotoxin for Treatment of Patients with Recurrent Malignant Glioma," Acta Neurochir. Suppl; 88: 93-103 (2003).
Weissleder, R., et al., "Shedding Light onto Live Molecular Targets," Nature Medicine; 9:123-128 (2003).
Wen, P.Y., et al., "Malignant Gliomas in Adults," New England Journal of Medicine 2008; 359:492-507 (2008).
Wu, Y., et al., "Imaging of Activated Caspase-3 in Living Cell by Fluorescence Resonance Energy Transfer During Photosensitization-Induced Apoptosis," SPIE 5630, 376. (2005).
Xing, Y., et al., "Quantum Dot Bioconjugates for in Vitro Diagnostics & In Vivo Imaging," Cancer Biomarkers 4, 307-319, (2008).
Yang, J., et al., "Tumor Tropism of Intravenously Injected Human-Induced Pluripotent Stem Cell-Derived Neural Stem Cells and Their Gene Therapy Application in a Metastatic Breast Cancer Model," Stem Cells. May 2012;30(5):1021-9. doi: 10.1002/stem.1051.
Yesavage, J.A.,et al., "Donepezil and Flight Simulator Performance: Effects on Retention of Complex Skills," Neurology, 59, 123, (2002).
Zhang, Y., et al., "Temozolomide/PLGA Microparticles: A New Protocol for Treatment of Glioma in Rats," Med Oncol. DOI 10.1007/s12032-010-9531-2. (2010).
Zhang, J., et al., "Endogenously EGFP-Labeled Mouse Embryonic Stem Cells," Aging Dis. Feb. 2011;2(1):18-29.
Zhao, D., et al., "Human Neural Stem Cell Tropism to Metastatic Breast Cancer," Stem Cells, 30 (2), 314-325 (2012).
Zhao, D., et al., "Neural Stem Cell Tropism to Glioma: Critical Role of Tumor Hypoxia," Mol Cancer Res, 6 (12), 1819-1829 (2008).
Ziu, M., et al., "Glioma-Produced Extracellular Matrix Influences Brain Tumor Tropism of Human Neural Stem Cells," J Neurooncol. Sep. 2006;79(2):125-33. Epub Apr. 6, 2006.
Bible E. et al. (Jun. 2009, e-published Mar. 10, 2009). "The support of neural stem cells transplanted into stroke-induced brain cavities by PLGA particles," *Biomaterials* 30(16):2985-2994.

(56) References Cited

OTHER PUBLICATIONS

Liu, D. et al (Sep. 15, 2010). "Biocompatible silica nanoparticles-insulin conjugates for mesenchymal stem cell adipogenic differentiation," Bioconjug Chem 21(9):1673-1684.

Mack, M. et al. (Jul. 2000). "Transfer of the chemokine receptor CCR5 between cells by membrane-derived microparticles: a mechanism for cellular human immunodeficiency virus 1 infection," *Nat Med* 6(7):769-775.

* cited by examiner

MPEG-BAE synthesis

Temozolomide and Iron Loading:

A    Unloaded Control      Loaded

Temozolomide Loading Efficiency: 78.6%

**Rhodamine is similar to temozolomide in size*

B    Unloaded Control      Loaded

Feraheme Loading Efficiency: 98.8%

Delayed Release profile:

FIGS. 28A-28J
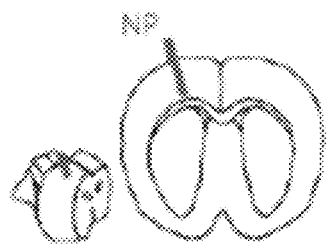
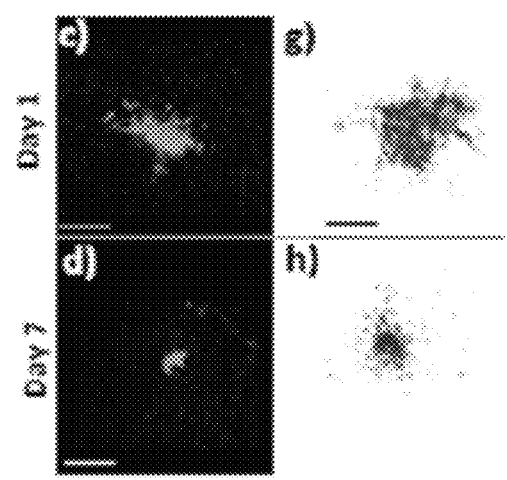
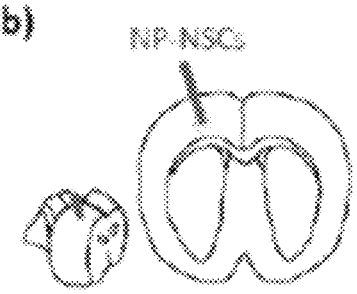
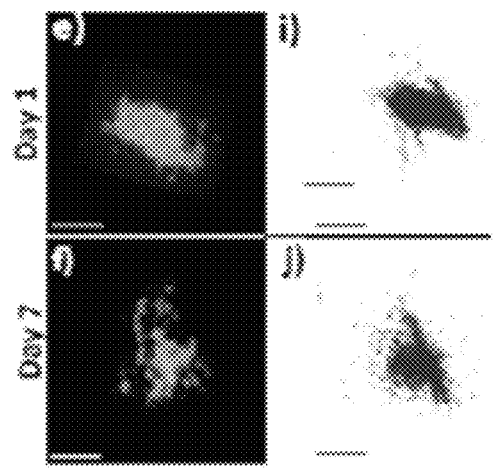

FIGS. 36A-36C
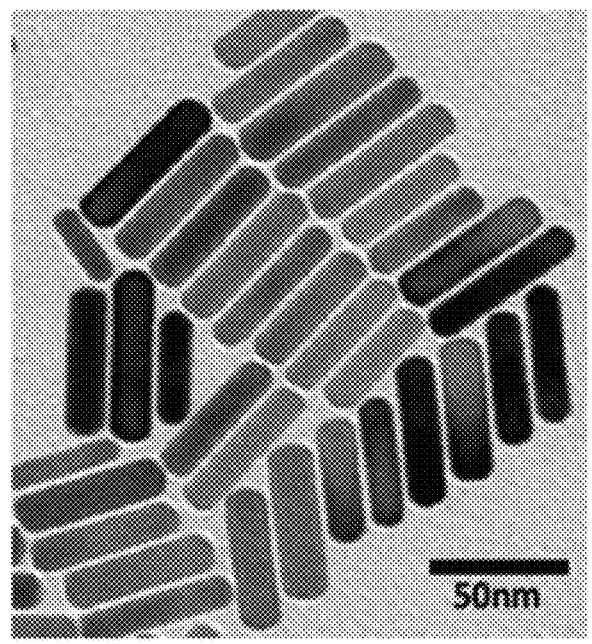
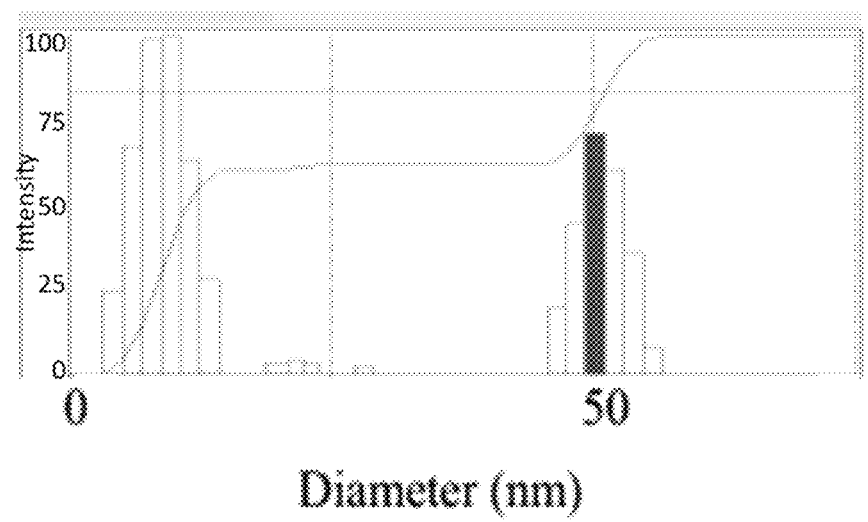
Diameter (nm)
C
| Zeta Potential (mV) |
| --- |
| 32.5 ± 1.6 |

FIGS. 38A-38I
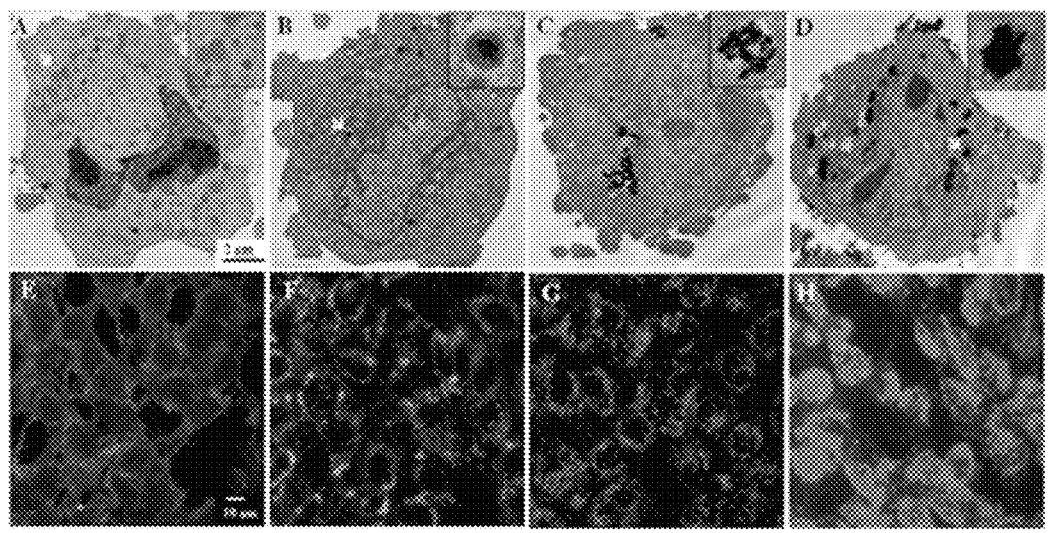
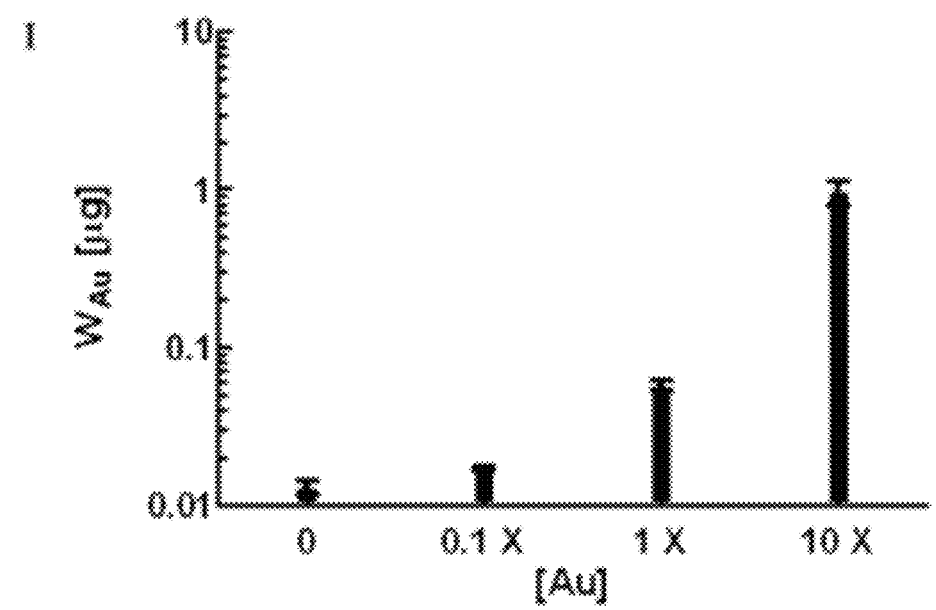

ENCAPSULATED DIAGNOSTICS AND THERAPEUTICS IN NANOPARTICLES—CONJUGATED TO TROPIC CELLS AND METHODS FOR THEIR USE

PRIORITY CLAIM

This application is a continuation of International Application Number PCT/US2012/060916, filed Oct. 18, 2012, which claims the benefit of U.S. Provisional Application No. 61/548,668, filed Oct. 18, 2011, the disclosures of which are incorporated herein by reference in their entirety, including the drawings.

BACKGROUND

Malignancies, such as infiltrative brain tumors and breast cancer (e.g., triple-negative breast cancer), often result in poor prognosis due to incomplete detection, resistance to treatment, and failure to eliminate of invasive tumor cells that migrate distant from the tumor. For example, malignant gliomas account for 70% of all brain tumors in adults (Wen & Kesari 2008) and approximately 190,000 patients are diagnosed every year (Parkin et al. 2002). There is currently no cure for this condition, and the majority of patients diagnosed with malignant gliomas die within 1 year (Parkin et al. 2002). Malignant gliomas are conventionally treated by surgery, radiotherapy, and chemotherapy (Castro et al. 2003). This treatment regimen, though aggressive, is almost always futile because tumor resurgence is common (King et al. 2005).

Several reasons may explain why these tumors are so resistant to treatment. First, once malignant transformation occurs, the glioma cells extensively infiltrate into normal brain parenchyma through the dense network of neuronal and glial cell processes and/or disseminate via cerebrospinal fluid pathways to generate distant tumor foci called microsatellites (Claes et al. 2007). Current treatment regimens fail to eliminate microsatellites. Limitations of current imaging technology makes the possibility of identifying and removing all tumor microsatellites by surgical excision unlikely because diffuse infiltration of glioma cells usually spreads beyond evident tumor boundaries (Yu & Ehtesham 2008; Wen & Kesari 2008). Invasive glioma cells also escape localized radiation therapy (Stupp et al. 2005), and chemotherapy has limited impact on the outcome of malignant gliomas because of difficulties delivering drugs across the blood-brain barrier and the lack of specificity of chemotherapeutic drugs for tumor cells (Deeken & Loscher 2007; Penas-Prado & Glibert 2007).

Another reason malignant gliomas may be so resistant to treatment is due to the heterogeneous cell composition of these tumors, which results in the emergence of drug-resistant cell populations (Cowen et al. 2002). Further, current treatment regimens fail to eliminate CD133+ malignant glioma tumor stem cells that may survive or escape treatment and cause recurrence of a tumor (Furnari et al. 2007).

Despite the development of magnetic resonance imaging (MRI) contrast enhancing agents such as superparamagnetic iron-oxide nanoparticles (SPIONs) (Shubayev et al. 2009; Arbab et al. 2005), improved formulations of standard tumor-toxic small molecule compounds such as Temozolomide (194.151 g/mol) (Zhang et al. 2010), and newer tumor-ligand specific toxic drugs such as targeted toxins directed against the IL-13 receptor (Kunwar 2003), the IL-4 receptor (Weber et al. 2003), the TGF-α receptor (Sampson et al. 2003), and the transferrin receptor (Laske et al. 1997); complete elimination of invasive cells has not been practicable given the inability to accurately detect the full extent of tumor cells or selectively deliver these agents to isolated invasive cells at effective concentrations (Zhang et al. 2010; Peer et al. 2007; Gullotti & Yeo 2009).

Many of the factors that contribute to the difficulty of treating malignant glioma also apply to other malignancies and cancers. Therefore, new carriers and therapeutic regimens that are capable of distinguishing between normal and malignant cells, eliminating heterogeneous populations of cancer cells and eliminating CD133+ cancer stem cells without harming healthy cells, and targeting tumor cells and diffuse glioma microsatellites are needed.

SUMMARY

In one embodiment, a therapeutic or diagnostic delivery vehicle is provided. The delivery vehicle may include one or more particles, such as microparticles nanoparticles (NPs) and stimuli-responsive particles, conjugated to a tropic cell that targets at least one pathological entity or site. The tropic cell may be a neural stem cell, a mesenchymal stem cell, a mesenchymal stromal cell, a hematopoietic stem cell, an adoptively transferred T-lymphocyte, a macrophage, a liver stem cell or an embryoid body.

Pathological entities or sites that may be targeted by the tropic cells described herein may include solid tumors (e.g. benign or malignant tumors; primary or metastatic tumors); tumor bulk, microsatellites or hypoxic tumor regions; pathologies that require passage of the blood brain barrier including, but not limited to, 1) brain tumors including, but not limited to, glioma and medulloblastoma, 2) stroke, 3) traumatic head injury, 4) dopaminergic or gabaergic dysfunction, 5) amyloid plaques, 6) ALS, 7) Spinal chord dysfunction, 8) inflammed central nervous system (CNS); Non-CNS pathologies (e.g., cancers, non-cancerous diseases or conditions) including, but not limited to, hepatic tumors, lung tumors, prostate tumors, breast tumors, ovarian carcinoma, hypoxia and ischemia, subcutaneous wounds, radiation damage, lung pathologies, thymus pathologies, bone pathologies, skin pathologies, melanoma, gastrointestinal tract pathologies, liver pathologies including hepatocellular carcinoma, bone marrow pathologies, bone pathologies, spleen, myocardial infarction, subarachnoidal space for autoimmune diseases, gastric gland pathologies, gastric cancer, Kaposi's sarcoma, multiple Sclerosis (MS), chronic inflammation, chronic wounds, tissue damage, muscular dystrophy, osteogenesis imperfect, infections, bacterial infections, Hodgkin's lymphoma, graft-versus-host disease.

In some aspects, the particle may be further conjugated to at least one chemotherapeutic agent such as temozolomide, carboplatin, cyclophosphamide, docetaxel, doxorubicin, gemcitabine, methotrexate, paclitaxel, sunitinib, Cisplatin, 5-fluorouracil, 7-ethyl-10-hydroxycamptothecin (SN-38), or a combination thereof. In another embodiment the entrapped therapeutic may be a neurotrophic factor, differentiative agent, signal transduction inhibitor, antioxidant, anti-angiogenic, immunostimulatory, or anti-inflammatory agent. In other aspects, the particle may be further conjugated to at least one diagnostic agent such as a superparamagnetic iron-oxide nanoparticle (SPION), Fluorine-19 ($^{19}F$), a long organic chain labeled with $^{19}F$, a CdT luminescent compound, gold, quantum dots, a radioisotope or other radioactive material, or a material that is activated by thermal neutrons.

In another embodiment, a pharmaceutical composition is provided. The pharmaceutical composition may include, among other things, a particle conjugated to a tropic cell such as those discussed above and at least one diagnostic or therapeutic agent, such as those described above. In some aspects, the tropic cell targets at least one pathological entity or site such as those described above.

In another embodiment, methods for diagnosing, monitoring or treating a pathological condition are provided. Such methods may include administering a therapeutically effective amount of a pharmaceutical composition such as the composition described above. In some aspects, the methods are directed toward a pathological condition such as amytrophic lateral sclerosis (ALS), hypoxia, ischemia, muscular dystrophy, osteogenesis imperfect, graft-versus-host disease, subcutaneous wounds, radiation sickness, a viral infection, a bacterial infection, a chronic inflammatory or proliferative disease, a cancer, a chronic wound, Kaposi's sarcoma, an autoimmune disease, inflammation related to tissue damage, wound or injury, dopaminergic dysfunction, Alzheimer's disease, or spinal chord dysfunction. Cancers that may be diagnosed, treated or monitored may include glioma, medulloblastoma brain cancer, breast cancer, ovarian cancer, gastric cancer, lung cancer, melanoma, prostate cancer, leukemia, lymphoma, pancreatic, or hepatic cancer.

BRIEF DESCRIPTION OF THE FIGURES

FIG. 36 illustrates the characterization of MUTAB-AuNRs according to one embodiment. A) TEM image of MUTAB-AuNRs deposited from DI water. B) Dynamic light scattering is consistent with the data from the TEM. C) Zeta Potential measurement verified the cationic charge of MUTAB-AuNRs.

FIG. 38 shows uptake of MUTAB-AuNRs bu NSCs using transmission electron microscopy (TEM) in accordance with one embodiment. NSCs were incubated for 16 h with either media alone or [0.01×], [0.1×], or [1×] MUTAB-AuNRs and then imaged by A-D) TEM or E-H) dark field microscopy with hyperspectral mapping. (A) and (E) are untreated control NSCs. (B) and (F) were treated with [0.01×] MUTAB-AuNRs. (C) and (G) were treated with [0.1×] MUTAB-AuNRs. (D) and (H) were treated with [1×] MUTAB-AuNRs. Areas enlarged inset in (B-D) correspond to the locations indicated by white arrows, where each indicates a clearly defined endosome containing MUTAB-AuNRs. (I) ICP-MS measurements confirm that uptake of the MUTAB-AuNRs by the NSCs is dose dependent.

DETAILED DESCRIPTION

Figure 1:
FIG. 1 is a schematic diagram of Feraheme® (~17-31 nm), which is an example of a SPION that may be used as a diagnostic agent in accordance with the embodiments described herein. When administered to a subject, Feraheme® can provide anatomical context, and enhance magnetic resonance imaging (MRI) sensitivity to $1 \times 10^5$ cells.

Tropic cells conjugated to a particle (e.g., a microparticle or a nanoparticle) for targeting pathological entities and sites, therapeutic conjugates, diagnostic conjugates and compositions including the same and methods for their use are provided herein. Specifically, a tropic cell may be conjugated to one or more microparticles or nanoparticles to form a delivery vehicle that specifically targets a pathological entity or site for the diagnosis, treatment and monitoring of a pathological condition. The particle or tropic cell may be further conjugated to a therapeutic agent, a diagnostic agent, or both, which may be part of a pharmaceutical composition that is used for diagnosing, monitoring, or treating a pathological condition. The tropic cell-particle conjugate, when further conjugated to one or more therapeutic agent, diagnostic agent or a combination of both travels to a tumor or tumor microsatellites to deliver a sustained release of a therapeutic and/or diagnostic cocktail that is capable of eliminating heterogeneous populations of cancer cells and cancer stem cells (e.g., The putative CD133+ glioma stem cell population) without harming normal cells.

Nanoparticle-Tropic Cell Delivery Vehicles

In some embodiments, a delivery vehicle for targeting pathological entities and sites includes a tropic cell component that is conjugated to one or more particle component to form a particle-tropic cell conjugate ("particle-tropic cell conjugate," "nanoparticle-tropic cell conjugate," "nanoparticle-tropic cell hybrid," or "NP-cell conjugate"). The tropic cell component may be conjugated to a single nanoparticle, to more than one nanoparticles, or to a plurality of nanoparticles.

The tropic cell component of the delivery vehicle is a type of tropic cell or cells that exhibits intrinsic tropism toward a particular physiological or pathological site or entity. It may possible to generate tropism where it doesn't exist using magnetic-directed cell migration (Singh 2009), where cells labeled with FE or Nd-FE-B can be directed to a specific location within the body, using an externally applied magnetic field. The tropic cell or cells used in accordance with the embodiments described herein may be any suitable cell type that exhibits intrinsic tropism including, but not limited to, Neural Stem Cells, Mesenchymal Stem Cells, Mesenchymal Stromal Cells, Hematopoetic Stem Cells, Adoptively transferred T-lymphocytes, Macrophages, Liver stem cells and Embryoid Bodies (ES cells). Such tropic cells may be used to target pathological sites or entities which tropic cell types exhibits tropism toward.

In some embodiments, the tropic cells may be used to target one or more physiological site, pathological site or entity. Examples of physiological sites, pathological sites and entities that may be targeted by tropic cells include, but are not limited to any solid tumors (e.g. benign or malignant tumors; primary or metastatic tumors); tumor bulk, microsatellites or hypoxic tumor regions; pathologies that require passage of the blood brain barrier including, but not limited to, 1) brain tumors including, but not limited to, glioma and medulloblastoma, 2) stroke, 3) traumatic head injury, 4) dopaminergic or gabaergic dysfunction, 5) amyloid plaques, 6) ALS, 7) Spinal chord dysfunction, 8) inflammed central nervous system (CNS); Non-CNS pathologies (i.e., cancers described below or elsewhere in the disclosure, non-cancerous diseases and conditions) including but not limited to hepatic tumors, lung tumors, prostate tumors, breast tumors, ovarian carcinoma, hypoxia and ischemia, subcutaneous wounds, radiation damage lung pathologies, thymus pathologies, bone pathologies, skin pathologies, melanoma, gastrointestinal tract pathologies, liver pathologies including hepatocellular carcinoma, bone marrow pathologies, bone pathologies, spleen, myocardial infarction, subarachnoidal space for autoimmune diseases, gastric gland pathologies, gastric cancer, Kaposi's sarcoma, multiple Sclerosis (MS), chronic inflammation, chronic wounds, tissue damage, muscular dystrophy, osteogenesis imperfect, infections, bacterial infections, Hodgkin's lymphoma, graft-versus-host disease.

Table 1 (below) shows tropic cells and their respective pathological tissues that may be targeted according to the embodiments described herein.

TABLE 1

Different cell types that exhibit tropism towards various pathologies

| Tropic Cell Type | Respective Pathology |
| --- | --- |
| Neural Stem Cells | Glioma, medulloblastoma, brain tumors in general, breast cancer metastasis, stroke, head injury, dopaminergic dysfunction, brain tumors and amyloid plaques, ALS, Spinal chord dysfunction |
| Mesenchymal Stem Cells | hepatic tumors, lung tumors, breast tumors, glioma, ovarian carcinoma, hypoxia and ischemia, subcutaneous wounds, radiation damage |
| Mesenchymal Stromal Cells | lung, thymus, bone, skin, cerebellum, and gastrointestinal tract, liver, bone marrow, bone, skin, brain, spleen, myocardial infarction, subarachnoidal space for autoimmune diseases, gastric glands, gastric cancer, Kaposi's sarcoma, brain cancer, Multiple Sclerosis (MS), chronic inflammation, chronic wounds, tissue damage, inflammed central nervous system (CNS), muscular dystrophy, osteogenesis imperfect |
| Hematopoetic Stem Cells | Glioma, brain tumors, lung tumors, prostate tumors, and breast tumors |
| Adoptively transferred T-lymphocytes | Brain Tumors, breast tumors, prostate tumor, infections, bacterial infections, melanoma, ovarian cancer, breast carcinoma, Hodgkin's lymphoma, lung cancer, and graft-versus-host disease. |
| Macrophages | Tumors, Viral infections, Bacterial infections |
| Liver stem cells | hepatocellular carcinoma |
| Embryoid Bodies (ES cells) | Glioma |

Figure 3:
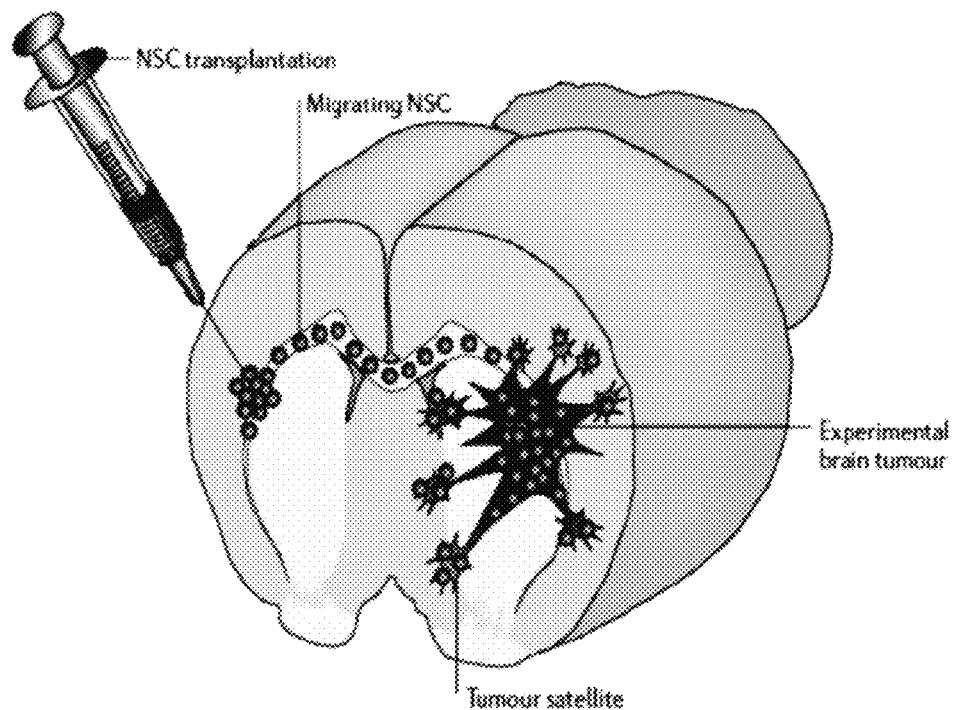
FIG. 3 is a schematic diagram illustrating tropism of neural stem cells (NSCs) toward malignant tumors according to some embodiments (adapted from Muller et al 2006). NSCs transplanted into one brain hemisphere migrate transcallosally to the tumor growing other hemisphere and also infiltrate tumor satellites distant from the main tumor mass.

*Sources of cells could include primary, immortalized, embryonic stem cell or induced pluripotent stem cells The use of tumor-tropic stem cells is advantageous because they inherently migrate through the blood-brain barrier (BBB), are distributed selectively to tumors and invasive tumor foci (Aboody et al. 2000), and penetrate to hypoxic tumor regions (Zhao et al. 2008). Thus, in one embodiment, the tropic cell that may be used as part of the particle-cell conjugate is a neuronal stem cell (NSC). NSCs are cells that can continuously self-renew while maintaining the potential to differentiate into both glial and neuronal cell lineages. NSCs transfected with the luciferase gene have been shown to migrate from the right hemisphere of mice, across the corpus callosum to tumor growth in the left hemisphere (Weissleder & Ntziachristos 2003), and were able to infiltrate small tumor satellites distant from the main tumor mass (Schmidt et al. 2005) (FIG. 3). The molecular basis of such NSC tropism seems to involve a response to gradients of chemotactic signals that emanate from lesioned brain regions (Schmidt et al. 2005). NSC tropism may be harnessed in order to deliver therapeutic substances to brain tumor satellites. Because NSCs can home selectively to invasive tumor cells (Aboody et al. 2000; Zhao et al. 2008), they provide an opportunity for developing targeted delivery strategies. Additionally, tumor tropic NSCs are an attractive choice of carrier for anti-cancer agents because they do not have pro-angiogenic or immunomodulatory properties that favor tumor growth (Tang et al. 2010).

It was previously demonstrated that tumor-tropic NSCs can be genetically engineered to express and deliver therapeutic proteins to infiltrative brain tumor cells (Aboody et al. 2000). However, this genetic approach is limited because many of the most effective diagnostic and therapeutic compounds are synthetic, inorganic, and/or extremely toxic, and therefore, cannot be expressed by NSCs. NSCs can also be induced to phagocytose SPIONs (Shubayev et al. 2009; Arbab et al. 2005; Neuberger et al. 2005), and can be used to track the migration of NSCs to tumors. However, phagocytosis of SPIONs has been shown to damage cell viability and alter stem cell states (Arbab et al 2004; Schafer et al. 2009; Schafer et al. 2007). In addition, cells do not endocytose more than 100 pg SPIONs per NSC (Tang et al. 2010). Further, NSCs do not remain viable for more than a week (Aboody et al. 2000), preventing sustained therapeutic or diagnostic effects. The particle-tropic cell delivery vehicles described herein will greatly broaden the type, concentration, and duration of therapeutic and diagnostic compounds that NSCs can target to tumors.

In one embodiment, the nanoparticle-tropic cell delivery vehicles and system described herein may be used to transport nanoparticles across the BBB. In one embodiment, a NSC-nanoparticle conjugate system enables small molecule therapeutics that cannot otherwise cross the BBB to be delivered directly to brain pathologies. As described in detail in Example 2 below, NPs were stably bound to the surface of a clinically relevant NSC line to analyze their ability to distribute NPs to tumor foci. The NPs used in Example 2 are larger (798 nm) than others previously conjugated to tropic cells and are too large to passively diffuse through brain tissue or cross the tumor-brain-barrier. The results demonstrate that 169 NPs per NSC did not impair tumor tropism in vitro. In vivo, NSC-coupled NPs exhibited significantly improved tumor-selective distribution and retention whether injected adjacent to the intracerebral glioma, contralaterally, or intravenously. These results indicate that NSCs can facilitate selective NP distribution to glioma, providing a means for improved drug delivery.

In another embodiment, the particle-tropic cell delivery vehicles described herein overcome some of the limitations of nanoparticle-mediated drug delivery. While some nanoparticle and microparticle carriers can also cross the BBB using tumor-compromised vasculature (Fukumor & Ichikawa 2002; Iyer et al. 2006), specific targeting of tumors with nanoparticles still remains a challenge. Increased tumor specificity has been attempted by modifying the surface of nanoparticles to contain tumor-retention peptide sequences (Peer et el. 2007). Despite these efforts, tumor-selective distribution of nanoparticles remains inefficient (<10% retained in tumor (Schluep et al. 2009)) and off-target deposits in the liver and spleen are common (Peer et el. 2007; Schluep et al. 2009; Gullotti & Yeo 2009). To increase specificity, drug release may be controlled by using nanoparticles that release therapeutic payloads in response to external signals such as pH (MacEwan et al. 2010), temperature (Haiyan et al. 2007), magnetic fields (Stuart et al. 2008), and light (Cui et al. 2011). Despite the development of these stimuli-responsive nanoparticles, challenges still remain including drug penetration within the tumor bulk, particularly due to poorly vascularized hypoxic regions, dense matrices and outward fluid-pressure gradients (MacEwan et al. 2010; Krishnamachari et al. 2009). It is also difficult to treat migratory tumor cells that disseminate distant from the primary tumor (Aboody et al. 2000). Therefore, according to some embodiments, the particle-cell hybrids can specifically target and penetrate tumors more efficaciously than existing nanoparticle technologies. The Examples below show that tumor-tropic neural stem cells (NSCs) can overcome these NP delivery obstacles by their ability to traverse vascular barriers, target, and penetrate invasive tumor foci.

The tropic cell may be conjugated to any suitable particle known in the art that enables the delivery vehicle to carry a diagnostic payload, a therapeutic payload or both to the pathological or physiological site or entity. The term "particle" as used herein may refer to any particle or substance having a diameter in the micrometer range, such as a "microparticle," which typically has a diameter of approximately <1 μm and higher, or a "nanoparticle," which typically has a diameter of 1 nm to 1 μm. In some embodiments, the size of the particles used herein typically have a diameter of 1 μm or less and may include microparticles, nanoparticles or both, but the size may vary based on their application. An increased particle size may enable increased amounts of diagnostic and therapeutic cargo to reach target cells or structures such as tumors. The size of the particles used herein may be between 300-500 nanometers, which is a size that cannot currently target brain tumors by relying on the Enhanced Permeability and Retention effect, as the maximum diameter for EPR effect is 200 nanometers (Acharya & Sahoo in press)).

In some embodiments, the particles used for NSC-conjugation may be synthesized using any suitable method known in the art. For example, approaches that may be used for particle fabrication may include, but are not limited to, oil-water emulsion/solvent evaporation, dispersion polymerization, template controlled (gellation, or photopolymerization), precipitation polymerization, self-assembly, spray drying of polymer solutions, or microfluidic-based polymerization.

According to some embodiments, the particles, microparticles or nanoparticles used herein may be carrier structures which are biocompatible with and sufficiently resistant to chemical and/or physical destruction by the environment of use such that a sufficient amount of the nanoparticles remain substantially intact after injection into the blood stream, by any other suitable route of administration or when incubated with an in vitro sample so as to be able to reach the nucleus of a cell or some other cellular structure. Drugs, active agents, bioactive or other relevant materials can be incubated with the nanoparticles, and thereby be adsorbed, encapsulated or attached to the particle.

In some embodiments, the particle, microparticle or nanoparticle may be a stimuli-responsive particle to ensure that the therapeutic and/or diagnostic compounds are released at the desired target site or entity, reducing the chance of off target effects. Several types of stimuli-responsive particles may be linked to cells to enable control over drug release according to the embodiments described herein. Stimuli responsive particles may also be employed for diagnostic purposes using FRET-based systems in which the diagnostic signal is only detectable in the presence of a disease-specific environment (ex. Tumor-specific low pH), or upon tumor killing if the signal is activated by caspase-3 (Wu et al. 2005). Table 2 (below) shows examples of particles that are responsive to various stimuli that may be used for controlled drug release within a particular environment according to embodiments described herein (e.g., pH-responsive particles for controlled drug release).

TABLE 2

Stimuli-responsive particles

| Drug Release Stimuli | Particle Composition |
|---|---|
| Optic (UV, xray, IR) | 1. liposomes or polymers composed of amphilphiles connected to photo-cleavable headgroups like Azobenzene, or 2'nitrobenzyl dendrons, Cinnamic Acid, or Fumaric Acid<br>2. Self-assembled polysaccharide nanogels |
| biochemical | 1. Enzymatically degradable peptides grafted into polymer, intrinsic to polymer (dextran, or protein-derived polymer), or grafted within self-assembled polysaccharide particles that degrade only in the presence of MMPs. (ex. MMP-2 is upregulated in gliomas, but any other Serine proteases or Cystein proteases (cathepsins) in general could be targeted)<br>2. Graft hydrogels with antigen and antibodies to create crosslinks that can be undone by the competitive binding of free antigen in environment (Ex. SDF-polymer conjugate particle cross-linked using CXCR4; then tumor-derived SDF competes for the CXCR4 binding and unravels the particle releasing the drug). The same concept could be applied for HCF-cMET or inflammatory cytokines |
| Time (hydrolysis) | 1. Poly(ethylene) glycol-Poly (lactic) acid, Poly (lactic) acid<br>2. Poly (glycolic) acid, Poly(ethylene) glycol-Poly(glycolic) acid<br>3. Poly (lactic-co-glycolic) acid (PGLA). Poly(ethylene) glycol-Poly (lactic-co-glycolic) acid (PEG-PGLA) |
| Thermal | 1. poly(N-isopropylacrylamide) poly(PIPAAm); PNIPAM<br>2. dithiol crosslinked poly(N-isopropylacrylamide)<br>3. poly(N-isopropylacrylamide-co-acrylic acid)<br>4. acrylic acid and acrylamide (1:1 ratio)<br>5. 2-carboxyisopropyl acrylamide, 2-aminoisopropyl acrylamide, 2-hydroxy-isopropyl acrylamide.<br>6. Poly(methacrylamide) derivatives<br>7. Poly (butyl vinyl ether)<br>8. Poly (ε-caprolactam)<br>9. Poly (n-vinylcaprolactam)<br>10. Poly(ethylene oxide)-block-poly(proyreneoxide)-block-PEO (Pluronics)<br>11. Self-assembled polysaccharide nanogels, Hydroxypropylcellulose, Methylcellulose<br>12. Elastin-like peptides |
| Chemical | 1. Particles that require oxygen to hold the particle together that degrade in hypoxic environments.<br>2. Particles that degrade in response to hydroxyl radicals that release antioxidants.<br>3. Oxidizing agents concentrate in inflammation sites and tumors and can induce drug release from the swelling of hydrogels through gluconic acid enzymatic production.<br>4. Oxidizing poly-sulfide nanoparticles—glucose oxidase oxidizes in the presence of glucose, so maybe if glucose oxidase were present with a bunch of oxidizing agents, then its enzyme production would be increased and it would degrade the particle. |
| Ultrasonic | This can be applied to enhance the mass-transport regulated release from many particle systems. |
| pH | 1. poly[2-(N,N-ditethylamino)ethyl methacrylate] (PEAMA )<br>2. Butanediolacrylate<br>3. Ethylacrylate<br>4. Diethylamino methacrylate copolymerized with poly(propyleneglycol)diacrylate<br>5. Diisopropylaminoethyl methacrylate copolymerized with poly(propyleneglycol)diacrylate<br>6. Self-assembled polysaccharide nanogels<br>7. methyl ether PEG conjugated to a pH-labile linker poly(β-amino ester) (MPAE)<br>8. Poly(histidine)-β-PEG<br>9. PEG-conjugated to ester, hydrazone, carboxy dimethylaleic anhydride, orthoester, imine, beta-thiopropianoate, vinylether, phophoramididate pH-libile crosslinkers<br>10. Thiolated heparin nanogels<br>11. Poly(ethylene oxide-beta-aspartic acis) (PEG-beta-ASp)<br>12. PolyKetal |

TABLE 2-continued

Stimuli-responsive particles

| Drug Release Stimuli | Particle Composition |
|---|---|
| Responsive to Multiple Stimuli | 1. Temperature, pH, and ionic strength sensitive: copolymerization of PNIPAM with COOH-containing monomers such as Acrylic acid, methacrylic acid, allylacetic acid, or amine-containing monomers like vinyl pyridine.<br>2. pH and temperature responsive: PMAC-poly (2-dimethylamino)ethylmethacrylate (DMAEMA)<br>3. pH and hydrolytically degradable: mixed micelles of PEG-PLA and methyl ether PEG conjugated to a pH-labile linker poly($\beta$-amino ester) (MPEG-PAE); or mixed micelles of PEG-PLA and poly(histidine)-$\beta$-PEG. |

In another embodiment, the linkage between (1) the therapeutic agent or the diagnostic agent and the particle or (2) the entire nanoparticle (including any associated therapeutic agents, diagnostic agents or combinations thereof) may be severable by a stimuli that releases the one or more therapeutic agent, diagnostic agent or a combination thereof in response to hydrolysis, swelling, chemical stimuli, electric stimuli, ultrasound, temperature, magnetism, light or pH. Alternatively, a cell-penetrating peptide on the surface of the nanoparticle may carry the payload inside the tumor cells.

In some embodiments, the particles may be tailored to ensure a linear, first-order, enteric release profile of the therapeutic. The timescale of release may range from immediate to months or years.

The particle, microparticle or nanoparticle may be conjugated to a tropic cell by any suitable coupling or conjugation method. In some embodiments, a tropic cell and a particle or nanoparticle may be linked to each other by any suitable tethering moiety that stably links functional groups present on the surfaces of particles and cells. In some embodiments, the cell surface group and/or the particle surface functional group are endogenously present on the cell and/or particle. Table 3 (below) shows endogenously present functional groups that may be used to link a tropic cell to a particle based on the type of tethering moiety selected.

TABLE 3

Endogenously Present Functional Groups

| Tethering Moiety | Cell Surface Functional Group | Possible Particle-Surface Functinal Group |
|---|---|---|
| Proteins | Amine | Particles with surfaces covered with carboxyl groups via ECD/NHS chemistry, or by using a carbodiimide EDAC crosslinker.<br>Perhaps particles covered with aldehydes, isothiocynates, or active esters would react directly. |
|  | Carboxyl | Particles with surfaces covered with amines via ECD/NHS chemistry, or by using a carbodiimide EDAC crosslinker |
|  | Thiol | Particles with surfaces covered with maleimide, 2-pyridyldithio, iodoacetyl, acrylates, methacrylates, or norbornenes |
| Proteins | Proteins | Antibody |
| Carbohydrates | Carbohydrates | Lectins/Selectins (ex. Sialyl-LewisX) |
| Lipids | Lipids | Antibody |
| Cholesterol | Cholesterol | Antibody |

In other embodiments, the cell surface group and/or the particle surface functional group are not endogenously present, but are instead engineered to be present on the surface. Table 4 (below) shows directly engineered cell surface functional groups that may be added to a cell and/or particle surface that may be used to link a tropic cell to a particle based on the type of tethering moiety selected.

TABLE 4

Engineering Exogenously Present Functional Groups-Direct cell surface engineering

| Tethering Moiety | Directly Engineered Cell Surface Functional Group | Paticle-Surface Functional Group |
|---|---|---|
| Lipid Bilayer | Lipid-PEG-Avidin, -streptavidin, -neutravidin inserts into cell | Biotinylated Particles |

TABLE 4-continued

Engineering Exogenously Present Functional Groups-Direct cell surface engineering

| Tethering Moiety | Directly Engineered Cell Surface Functional Group | Paticle-Surface Functional Group |
|---|---|---|
| | membrane (example: Oleyl PEG conjugates) | |
| Lipid Bilayer | Lipid-PEG-hepten inserts into cell membrane | Particles with anti-hapten on the surface |
| Lipid Bilayer | Lipid-PEG-methacyrylate, -acrylate, -norbornene inserts into cell membrane | Particles with photo-reactive acrylates, acrylamides, methacrylates, thiols on the surface |
| Lipid Bilayer | The extracellular region of certain receptors can be linked to glycosylphosphatidylinositol and anchored into the membrane | Particles with the corresponding ligand on the outside. |
| Lipid Bilayer | metal chelators that are covalently linked to acyl-like chains or lipids that insert into the cell membrane | Particles displaying a his-tag on the surface. |
| Amines | succinimidyl ester of 6-((acryloyl)amino)hexanoic acid reacts with amines of proteins to yield acrylamides | Copolymerize with polyacrylamide or acrylate/methacrylate particle surfaces |
| Hydroxyl groups present on polysaccharides, glyoproteins, and carbohydrates (e.g., Sailic acid, galactose serine, and threonine) | Hydroxyl groups undergo periodate oxidation to form reactive aldehydes or ketones. Ex. Galactose oxidase oxidizes terminal galactose residues to aldehydes. The aldehydes and ketones can further react with hydrazines derivatives, including hydrazides, semicarbazides, and carbohydrazides, and hydroxylamines (aminooxy compounds). Ex. Biotin hydrazide, Biotin-hydroxylamine, PEG-Hydrazide | 1. Particles with hydrazides, semicarbazides, carbohydrazides, or hydroxylamines (aminooxy compounds) on the outside. Ex. This can be done my modifying surface amino groups with SANH to form surface hydrazides. 2. If biotin hydrazine/hydroxylamine is used, particles with either Avidin, streptavidin, or neutravidin on the surface would couple. |
| Proteins | Haptenylation of cell surface proteins | Particles with anti-hapten on the surface |
| Carboxylic Acids | In aqueous solution, carboxylic acids can be converted to amides (see below), acyl hydrazides (see above) or hydroxamic acids | Azide-coated particles |
| Glutamine residues | transglutaminase-catalzyed transamidation reaction of glutamine residues on proteins | Amines on the surface of proteins. aliphatic spacer in the amine probe enhances the reaction. The cadaverine (—NH(CH$_2$)$_5$NH—) spacer is usually optimal. Biotin-cadavarines are available, in which case and avidin, streptavidin, or neutravidin coated particle could be used. |

Figure 4:
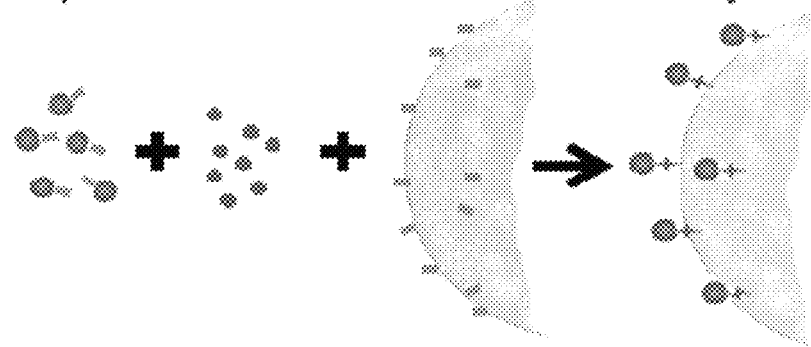
FIG. 4 is a schematic diagram illustrating a fabrication/preparation scheme for a particle-cell conjugate or hybrid using a biotin-avidin linkage according to some embodiments.
Figure 16:
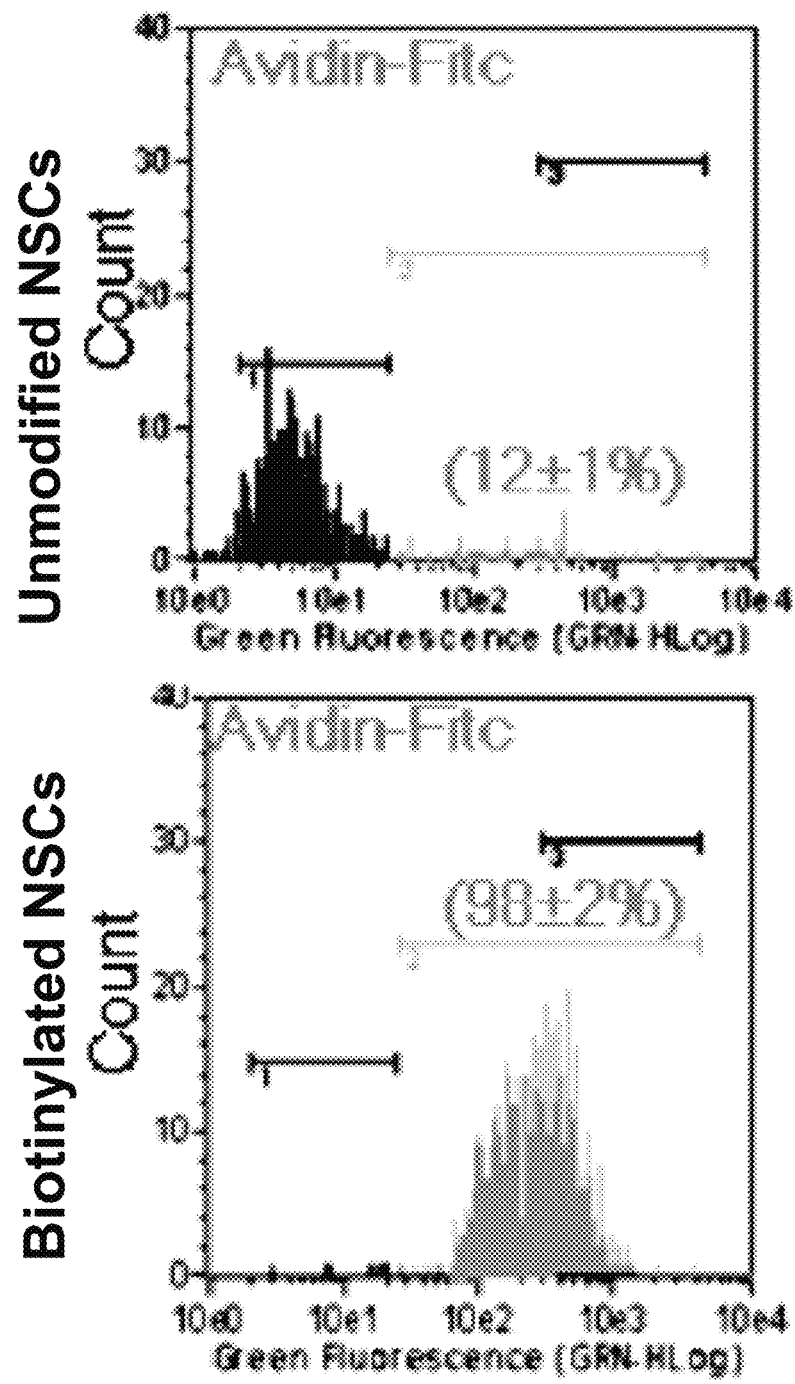
FIG. 16 shows results of a FACs analysis quantifying avidinylation efficiency for unmodified (top panel) and biotinylated (bottom panel) NSCs according to one embodiment.
Figure 17:
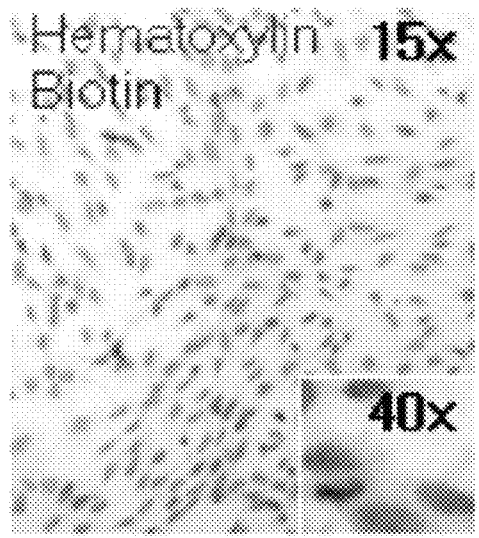
FIG. 17 shows NSC biotinylation as visualized via chromogenic (hematoxylin and biotin, left panels) and fluorescent (Nestin and Avidin-dsRed, right panels) immunological techniques for both unmodified (top panel) and biotinylated (bottom panel) NSCs, according to some embodiments.
Figure 17:
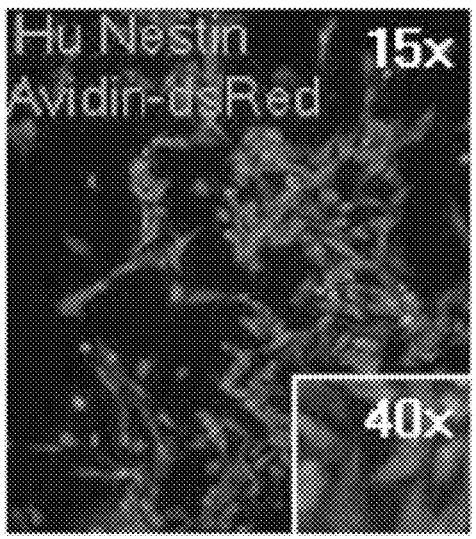
Figure 17:
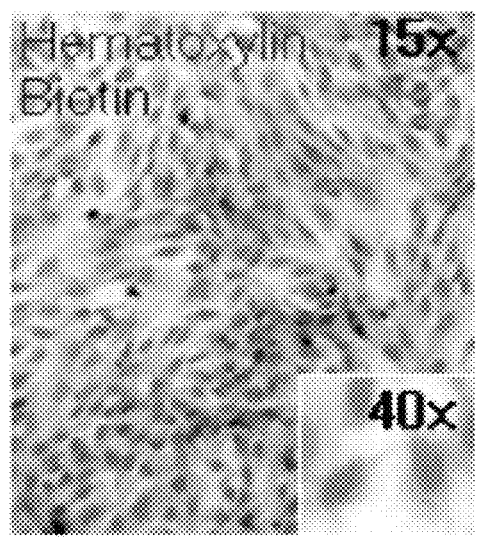
Figure 17:
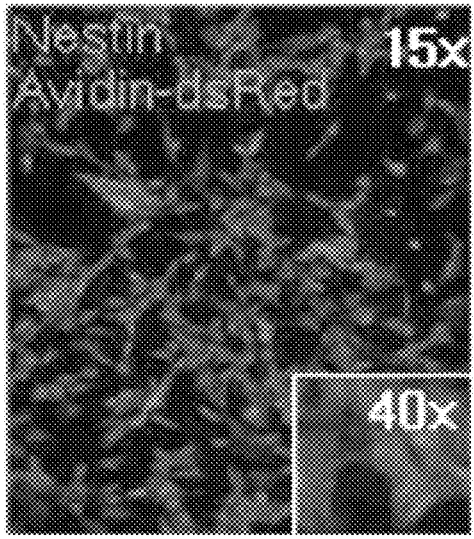

In another embodiment, the particle and tropic cell are conjugated using a previously established cell surface engineering approach in which sailic acid residues are biotinylated prior to linking to nanoparticles (Krishnamachari et al. 2008; U.S. Patent Application Publication No. 20100190257 to Krishnamachari, both of which are hereby incorporated by reference as if fully set forth herein). In this approach, cells may be connected to microparticles by employing a standard biotin-avidin binding scheme (FIG. 4), where biotinylated microparticles are bound to biotinylated cell surfaces with avidin as the bridging protein (FIG. 16-17) (Krishnamachari et al 2008).

In another embodiment, the cell surface group and/or the particle surface functional group are added to the cell and particle surface by metabolic cell surface engineering Table 5 (below) shows metabolically engineered cell surface functional groups that may be used to link a tropic cell to a particle based on the type of tethering moiety selected.

TABLE 5

Engineering Exogenously Present Functional Groups-Metabolic cell surface engineering

| Tethering Moiety | Metabolically Engineered Cell Surface Functional Group | Particle-Surface Functional Group |
|---|---|---|
| Glycoproteins (See FIG. 18) | Azides 1. Click-iT GalNAz metabolic glycoprotein labeling reagent (tetraacetylated N-azidoacetylgalactosamine for labeling O-linked glycoproteins. 2. Click-iT ManNAz metabolic glycoprotein labeling reagent (tetraacetylated N-azidoacetylmannosamine for labeling sialic acid-modified glycoproteins. 3. Click-iT GlcNAz metabolic glycoprotein labeling | Alkyne 1. Modify NHS-terminated nanoparticles with Click-iT succinimidyl ester DIBO alkyne; 2. Modify SH-terminated nanoparticles with Click-iT maleimide DIBO alkyne 3. Modify carboyl-terminated nanoparticles with Click-iT amine |

TABLE 5-continued

Engineering Exogenously Present Functional Groups-Metabolic cell surface engineering

| Tethering Moiety | Metabolically Engineered Cell Surface Functional Group | Particle-Surface Functional Group |
|---|---|---|
| | reagent (tetra-acetylated N-azidoacetylglucosamine for labeling O-linked N-acetylglucosamine (O-GlcNAcymodified glycoproteins.<br>Thiols<br>$Ac_5ManNTGc$ metabolic glycoprotein reagent to generate free Thiols on the surface of the cells | DIBO alkyne<br>Particles with surfaces covered with maleimide, 2-pyridyldithio, iodoacetyl, acrylates, methacrylates, or norbornenes |
| Amino groups | Alkynes<br>1. Modify cells NHS groups with Click-iT succinimidyl ester DIBO alkyne.<br>2. Modify cells SH— groups with Click-iT maleimide DIBO alkyne. | Azides<br>Modify nanoparticle surface to contain surface Azide groups. |
| Sialic Acid | Azides<br>$Ac_4ManNAz$ metabolic glycoprotein labeling reagent (peracetylated azidoacetylmannosamine for labeling sialic acid-glycoconjugates).<br>**no pH change like the other reaction | Phosphanes<br>Modify nanoparticle surface to contain phosphane groups "Staudinger reaction" |
| Lipids | Azides<br>1. Click-iT farnesyl alcohol, azide,<br>2. Click-iT geranylgeranyl alcohol, azide,<br>3. Click-iT palmitic acid, azide (15-azidopentadecanoic acid)<br>4. Click-iT myristic acid, azide (12-azidododecanoic acid) | Alkyne<br>1. Modify NHS-terminated nanoparticles with Click-iT succinimidyl ester DIBO alkyne;<br>2. Modify SH-terminated nanoparticles with Click-iT maleimide DIBO alkyne<br>3. Modify carboyl-terminated nanoparticles with Click-iT amine DIBO alkyne |

In another embodiment, the linkage between the particle and the tropic cell may be severable by a stimuli that releases the loaded particle which may or may not contain an internalization ligand to enable subsequent uptake of the particle by the pathological cells. This mechanism would enable delivery of siRNA, shRNA, plasmid DNA, or other therapeutics that require nuclear or endosomal loacalization.

Therapeutic Agents

Because particles carrying many different cargo types can be attached to the same NSC, this approach may be used in any suitable combinatorial drug regimens and simultaneous diagnostic and therapeutic purposes, such as those described below.

According to the embodiments described herein, one or more therapeutic agents may be entrapped or encapsulated in or otherwise conjugated to the particle component of the particle-tropic cell conjugate delivery vehicles described above. The one or more therapeutic agents may include, but are not limited to, anti-cancer agents, antibiotic, anti-viral agents, anti-HIV agents, anti-parasite agents, anti-protozoal agents, anesthetics, anticoagulants, inhibitors of enzymes, steroidal agents, steroidal or non-steroidal anti-inflammatory agents, antihistamines, immunosuppressant agents, anti-neoplastic agents, antigens, vaccines, antibodies, toxins, targeted toxins, decongestants, sedatives, opioid, analgesics, anti-pyretics, birth control agents, hormones, prostaglandins, progestational agents, anti-glaucoma agents, ophthalmic agents, anti-cholinergics, analgesics, anti-depressants, anti-psychotics, neurotoxins, hypnotics, tranquilizers, anti-convulsants, muscle relaxants, anti-Parkinson agents, anti-spasmodics, muscle contractants, channel blockers, miotic agents, anti-secretory agents, anti-thrombotic agents, anticoagulants, anti-cholinergics, beta-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), inhibitors of DNA, RNA, or protein synthesis, or any suitable small molecule therapeutics, protein therapeutics or nucleic acid therapies (e.g., siRNAs or DNA plasmids).

In one embodiment, the therapeutic agent is a chemotherapeutic agent. Examples of chemotherapeutic agents that may be used according to the embodiments described herein include, but are not limited to 13-cis-Retinoic Acid, 2-CdA 2-Chlorodeoxyadenosine, 5-Azacitidine, 5-Fluorouracil, 5-FU, 6-Mercaptopurine, 6-MP, 6-TG, 6-Thioguanine, 7-ethyl-10-hydroxycamptothecin (SN-38), Abraxane, Actinomycin-D, Aldesleukin, Alemtuzumab, ALIMTA, Alitretinoin, All-transretinoic Acid, Alpha Interferon, Altretamine, Amethopterin, Amifostine, Aminoglutethimide, Anagrelide, Anastrozole, Arabinosylcytosine, Ara-C, Arsenic Trioxide, Asparaginase, ATRA, Azacitidine, BCG, BCNU, Bendamustine, Bevacizumab, Bexarotene, Bicalutamide, BiCNU, Bleomycin, Bortezomib, Busulfan, C225, Calcium Leucovorin, Camptothecin-11, Capecitabine, Carboplatin, Carmustine, Carmustine Wafer, CC-5013, CCI-779, CCNU, CDDP, CeeNU, Cetuximab, Chlorambucil, Cisplatin, Citrovorum Factor, Cladribine, Cortisone, CPT-11, Cyclophosphamide, Cytarabine, Cytarabine Liposomal, Dacarbazine, Dacogen, Dactinomycin, Darbepoetin Alfa, Dasatinib, Daunomycin, Daunorubicin, Daunorubicin Hydrochloride, Daunorubicin Liposomal, Decadron, Decitabine, Denileukin, Diftitox, Dexamethasone, Dexamethasone Acetate, Dexamethasone Sodium Phosphate, Dexasone, Dexrazoxane, DHAD, DIC, Diodex, Docetaxel, Doxorubicin, Doxorubicin Liposomal, DTIC, Epirubicin, Epoetin Alfa, Erbitux, Erlotinib, Erwinia L-asparaginase, Estramustine, Ethyol, Etoposide, Etoposide Phosphate, Everolimus, Filgrastim, Floxuridine, Fludarabine, Fluorouracil, Fluorouracil (cream), Fluoxymesterone, Flutamide, Folinic Acid, Fulvestrant, G-CSF, Gefitinib, Gemcitabine, Gemtuzumab ozogamicin, Gemzar, GM-CSF, Goserelin, Granulocyte—Colony Stimulating Factor, Granulocyte Macrophage Colony Stimulating Factor, Hexadrol, Hexamethylmelamine, HMM, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idarubicin, IFN-alpha, Ifosfamide, IL-11, IL-2, Imatinib mesylate, Imidazole Carboxamide, Interferon alfa, Interferon Alfa-2b (PEG Conjugate), Interleukin—2, Interleukin-11, Irinotecan, Isotretinoin, Ixabepilone, Kidrolase (t), Lapatinib, L-asparaginase, LCR, Lenalidomide, Letrozole, Leucovorin, Leukeran, Leuprolide, Leurocristine, Liposomal Ara-C, Lomustine, L-PAM, L-Sarcolysin, Maxidex, Mechlorethamine, Mechlorethamine Hydrochloride, Megestrol, Megestrol Acetate, Melphalan, Mercaptopurine, Mesna, Methotrexate, Methotrexate Sodium, Methylprednisolone, Mitomycin, Mitomycin-C, Mitoxantrone, MTC, MTX, Mustine, Nelarabine, Nilotinib, Nilutamide, Nitrogen Mustard, Nplate, Octreotide, Octreotide acetate, Ofatumumab, Oprelvekin, Oxaliplatin, Paclitaxel, Paclitaxel Protein-bound, Pamidronate, Panitumumab, Pazopanib, PEG Interferon, Pegaspargase, Pegfilgrastim, PEG-L-asparaginase, PEMETREXED, Pentostatin, Phenylalanine Mustard, Prednisolone, Prednisone, Procarbazine, Prolifeprospan 20 with Carmustine Implant, Raloxifene, Rituximab, Romiplostim, Rubidomycin hydrochloride, Sargramostim, Sorafenib, STI-571, Streptozocin, SU11248, Sunitinib, Temozolomide, Temsirolimus, Tenipo-side, TESPA, Thalidomide, Thioguanine, Thiophosphoamide, Thiotepa, Topotecan, Toremifene, Tositumomab, Trastuzumab, Tretinoin, TSPA, VCR Vinblastine, Vinblastine Sulfate, Vincristine, Vinorelbine, Vinorelbine tartrate, VLB, VM-26, Vorinostat, Votrient, VP-16, Zoledronic acid, Zolinza, or a combination thereof. Such chemotherapeutic agents may be used to treat glioma or any other type of cancer described herein according to treatment regimens known in the art. Effective combinatorial regimens are also possible because particles carrying different cargo loads can be attached to the same NSC.

Several combination or combinatorial chemotherapy treatment regimens are known in the art and may be encapsulated by the particles in accordance with the embodiments described herein. Such chemotherapies may include, but are not limited to 5-FU/LV 5-FU/LV+BV, 6-MP/CPM/Ara-C, 8 in 1, ABV, ABVD, AC, ACE, AC-T, AD, AIDA, AP, AT, BEACOPP, BEP, BIC, BIP, BV, CA, CAE, CAF, CAP, Carbo—Tax, CAV, CAV/EP, CC, CD, CDDP/VP-16, CDE, CEF, CF, CFM, ChIVPP, CHOP, CHOP+R, CISCA, CMF, CMFP, CMV, CNOP, CODOX-M, COMLA, COMP, COP, COPE, COPP, CP, CT, CVD, CVP, Cy/A, CYVADIC, DA, Dartmouth Regimen, DAT, DAV, DCTER, de Gramont Regimen, DHAP, DI, DVD, EAP, EC, ECF, ELF, EMA-86, EP, EPOCH, EPOCH+R, ESHAP, EVA, EVAP, FAM, FAMTX, FAP, FC, FEC, FL, FND, FOLFIRI, FOLFIRIB, FOLFOX, FOLFOX4+BV, FP, French Regimen, FUP, FZ, GC, GEMOX, German Regimen, HEC, HI-CDAZE, HiDAC, ICE, IDMTX, IDMTX/6-MP, IE, IFL, IFL/BV, IFoVP, ITP, IVAC, Linker Regimen Consolidation, Linker Regimen Induction, Linker Regimen Maintenance, M2, MACOP-B, Magrath Protocol, MAID, Mayo Clinic schedule, m-BACOD, MINE, MINE-ESHAP, Mini-BEAM, MOBP, MOPP, MOPP/ABVD, MP, MTX/6-MP, MTX/6-MP/VP, MTX-CDDP/Adr, MVAC, NA, NFL, NOVP, OD, OPA, OPPA, PC, PC*, PCB, PCE, PCV, PE, PEB, PF, PFL, POC, ProMACE/cytaBOM, PVA, PVB, PVDA, RICE, Roswell Park schedule, Saltz Regimen, SMF, Stanford 5, Stanford Five, Stanford Regimen, Stanford V, TAC, TAP, TIC, TIP, TIT, Topo/CTX, VAB-6, VAC, VAC/Adr, VAD, VATH, VBMCP, VeIP, VIP, VP, X+T, XELIRI, and XELOX.

In another embodiment, a chemotherapeutic agent such as those above may be combined with at least one additional therapeutic agent. For example, a chemotherapeutic agent may be delivered in combination with one or more additional chemotherapeutic agents or with another therapeutic agent such as an inhibitor of detoxification (particularly where the inhibitor of detoxification would be systemically toxic at the required dose). In this case, at least 2 therapeutic agents are entrapped or encapsulated in or otherwise conjugated to the particle component of the particle-tropic cell conjugate delivery vehicles described above.

For example, Temozolomide resistance is often dependent on DNA repair proteins such as O6-methylguanine DNA methyltransferase (MGMT) (Bobola et al 1996). Thus, a primary drug such as Temozolomide (TMZ) may be delivered from a first set of nanoparticles, and a secondary drug such as MGMT may be delivered by a second set of particles. The release profiles of each drug may be appropriately adjusted to ensure maximum susceptibility of tumor cells to the primary drug and minimize drug resistance. This treatment regimen may overcome current challenges with DNA-repair inhibitors including the associated bone marrow toxicities. The ability to target delivery of multiple chemotherapeutic agents together with multiple inhibitors of their detoxification pathways may present an additional effective approach.

In another embodiment, the therapeutic agent is a compound that prevents tumor invasion. Such compounds may include, but are not limited to tissue inhibitors of metalloproteinases (TIMPS) such as inhibitors of MMP-2 (Guo et al. 2005) and anti-twist siRNA (Elias et al. 2005).

In another embodiment, the one or more therapeutic agents may include a non-radioactive radiation sensitizer. These drugs may be delivered to the tumor in a targeted fashion while minimizing exposure of healthy cells to these drugs. The lower-dose radiation is then applied so that the tumor cells exposed to the drug are more susceptible to radiation-induced damage than the healthy tissue. Example radiation sensitizers include, but are not limited to, 5'FU, platinum analogs, gold, silver, gemcitabine, DNA Topoisomerase I-Targeting Drugs, farnesyltransferase Inhibitors, or COX-2 Inhibitors (Kvols 2005). This approach allows for targeted distribution of the radiosensitizer, and also allows for combinations of sensitizers that have different mechanisms of action.

In another embodiment, a metal such as gold, gold colloid, gold spheres, gold rods or other gold particles that are functionalized and are coupled to, bound to or internalized by the NSCs to form an NSC-metal delivery vehicle may target tumor cells. Once the NSC-metal delivery vehicle has reached the tumor site, they may be heated by externally by any suitable heat or frequency source including, but not limited to, applied near infared (NIR) wavelength laser, deeply invasive side looking NIR laser cannula or externally applied radiofrequency waves, causing death of the targeted cells. Alternatively, silver or carbon nanotubes may be used to target and destroy tumor cells in the same manner.

Gold nanoparticles (AuNPs) have shown great promise as a novel therapeutic technology for the treatment of cancer due to their non-cytotoxic nature, ease of synthesis and functionalization and, most importantly, their tunable plasmonic properties (Murphy et al. 2005; Connor et al. 2005; Kelly et al. 2002; Link & El-Sayed 1999). This allows AuNPs to be designed such that they cause local heating when exposed to near-infrared (NIR) light (El-Sayed et al. 2006). This is significant because of the wavelengths of light, NIR is least absorbed by blood and water, which allows it to penetrate deeply enough into tissue (~4 mm) to be focused on AuNPs for selective photothermal ablation of tumors (Daniel & Astruc 2004; Huang et al. 2008). Current clinical thermal ablation strategies have shown promise for a number of tumor types, particularly liver and kidney cancers, but are limited by the lack of selective heating. The surrounding healthy tissue is heated at the same rate as the tumor making it nearly impossible to destroy tumor margins without causing significant collateral damage (van der Zee 2002; Prudhomme et al. 1996; Jolesz 2009; Philipp et al. 1995; Seki et al. 1999; Mirza et al. 2001). AuNPs with varied morphologies, including nanospheres, nanoshells, nanocages, and nanorods, have been used to add selectivity to this photothermal ablation (James et al. 2007; Tong et al. 2007; Chen et al. 2007; Hirsch et al. 2003). Selective accumulation of the AuNPs within the tumor allows for the use of a NIR laser to significantly heat AuNPs and surrounding tumor tissue, without appreciably heating or damaging normal tissue. A recent report suggests that with current production techniques gold nanorods (AuNRs) exhibit the best photothermal efficiency as compared to other AuNPs (Malugin & Ghandehari 2010; von Maltzahn et al. 2009; Niidome et al. 2006; Cole et al. 2009).

The use of AuNPs thus renders the problem of specific heating to be one of depositing and retaining the AuNPs selectively within the tumor. Currently, passive and active targeting strategies have been attempted for delivery of AuNPs to tumor foci. Most passive strategies depend on the fact that tumors are prone to the accumulation of particles in the size range of approximately 50-200 nm. This is commonly referred to as enhanced permeability and retention (EPR) (Greish 2010), and it is the result of rapidly growing tumor vasculature being malformed with larger pores, allowing particles to extravasate out. In addition, tumor tissue generally has poor lymphatic drainage, making particles that enter the tumor environment prone to remain there. Active targeting of nanoparticles is accomplished by functionalizing them with ligands, such as monoclonal antibodies, that specifically bind to receptors overexpressed in the tumor environment (El-Sayed et al. 2006; Fay & Scott 2011; Harrington et al. 20001 Paciotti et al. 2006; Peer et al. 2007). Using these strategies, progress has been made in NP-mediated targeting of drugs to tumors, but even in the best cases, several major challenges remain for controlling the biodistribution of nanoparticles. In general, nanoparticles predominantly accumulate in the liver and spleen, have difficulty penetrating poorly vascularized hypoxic tumor regions and are unable to cross the blood-brain barrier.

As described above, NSCs may be used as carriers for nanoparticles in order to overcome these biodistribution challenges. NSCs have demonstrated inherent tumor tropic properties in pre-clinical brain and other invasive and metastatic tumor models, migrating selectively to invasive tumor foci, penetrating hypoxic tumor regions, and even traversing the blood-brain barrier to target intracranial tumor foci following intravenous administration (Kim et al. 2006b; Zhao et al. 2008; Frank et al. 2009; Aboody et al. 2000; Aboody et al. 2006; Danks et al. 2007). NSCs do not intrinsically have any anti-tumor efficacy, but can be modified to carry various anti-cancer payloads. One strategy involves genetically modifying NSCs to express an enzyme that will convert a prodrug into the active compound. This approach has been shown to produce a significant tumor-killing effect, decreasing tumor burden and/or increasing long-term survival in mice models (Zhao et al. 2008; Danks et al. 2007; Gutova et al. 2012; Zhao et al. 2012). Moreover, an established, clonal immortalized human NSC line (Kim 2004; Kim et al. 2002) which expresses cytosine deaminase (HB1.F3.CD) in order to convert the prodrug 5-fluorocytosine into the active chemotherapeutic 5-fluorouracil, is currently in a first in-human Phase I clinical trial for the treatment of recurrent glioma patients (NCT01172964).

As described in the Examples below, in vitro and in vivo studies demonstrate NSC internalization of cationicly charged 11-mercaptoundecyltrimethylammonnium bromide (MUTAB) stabilized gold nanorods (AuNRs). Transmission electron microscopy (TEM) and dark field microscopy demonstrated robust uptake of MUTAB-AuNRs into cells, with no significant affect on NSC viability or tumor-tropism. Moreover, NSCs loaded with MUTAB-AuNRs are able to eradicate tumor cells when stimulated with near-IR (NIR) laser. In vivo studies also demonstrate enhanced distribution and retention of AuNPs at tumor sites when loaded into NSCs, as compared to free AuNPs into the bloodstream. This should increase the thermoablation of tumor cells upon stimulation with NIR.

In another embodiment, the one or more therapeutic agents may include a neuroprotective agent and/or nootropic drug. Childhood cancers treated with traditional methods (including surgery, radiation, and chemotherapy) produce significant amounts of physiological stress in a patient leading to major injury to the brain. These pathological insults frequently induce cognitive "fog" which leads to an acute, and often long term, developmentally sensitive decline in information processing abilities of patients. Neuroprotective agents and/or Nootropic drugs may be of use in preventing or treating this condition (Partridge 2000-2011); Yesavage et al. 2002). However, ineffective delivery of these compounds across the BBB is the primary hurdle slowing the translation of therapies into the clinic for brain tumors, stroke, and also neurodegenerative diseases (Partridge 2000-2011). These proteins may be delivered from the nanoparticles attached to NSCs enabling a new means to carry these compounds across the BBB. Example neurotrophic factors that act as a neuroprotective agent and/or nootropic drug include, but are not limited to, brain derived neurotrophic factor (BDNF), glial derived neurotrophic factor (GDNF), ciliary neurotrophic factor (CNTF), insulin-like growth factor (IGF)-1, and nerve growth factor (NGF). Antioxidants are also neuroprotective. More than one agent may be used to produce an optimal effect, and this too is a possibility using NSC-particle conjugates either by loading defined factors into nanoparticles attached to the surface, or also due to intrinsic or genetically engineered protein products that NSCs can produce.

The therapeutic embodiments described above may be combined with the diagnostic embodiments described herein for simultaneous diagnosis and treatment of brain cancer because particles carrying different cargo loads can be attached to the same NSC.

Figure 2:
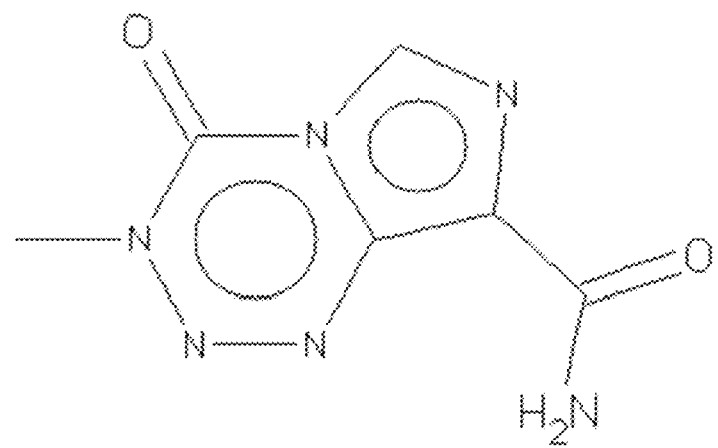
FIG. 2 shows the structure of Temozolomide (TMZ) (194.151 g/mol), a tumor-toxic small molecule that may be used as a therapeutic agent in accordance with the embodiments described herein.

In one embodiment, the one or more therapeutic agents encapsulated by the particles described herein is Temozolomide. Temozolomide (TMZ) is a DNA alkylating agent that is regarded as the first-line chemotherapy for glioblastoma (FIG. 2). In another embodiment, the one or more therapeutic agent encapsulated by the particles described herein is Docetaxel a the first-line chemotherapy for breast cancer, or any of the chemotherapeutic agents discussed above.

Diagnostic Agents

According to the embodiments described herein, one or more diagnostic agents may be entrapped or encapsulated in or otherwise conjugated to the particle component of the particle-tropic cell conjugate delivery vehicles described above. The one or more therapeutic agents may include, but are not limited to, superparamagnetic iron-oxide nanoparticles (SPIONs) (e.g., Feraheme®), Fluorine-19 ($^{19}F$) or long organic chains labeled with $^{19}F$, CdT luminescent compounds (e.g., CdSe, CdTe, HgTe, PbS, PbSe, PbTe, InAs, InP, and GaAs), gold, quantum dots, radioisotopes or other radioactive materials that emit alpha, beta or gamma rays (e.g., Barium-133, Cadmium-109, Cesium-137, Cobalt-60, Europium-152, Iodine-125, Iodine-131, Manganese-54, Palladium-103, Polonium-210, Ruthenium-106, Rhodium-103, Strontium-89, Technetium 99m, Yttrium-90, and Zinc-65), materials that are activated by thermal neutrons (e.g. Boron-11 captures a thermal neutron and generates an energetic lithium-7 nucleus and an alpha particle).

Various other attempts have been made to develop a way to track and visualize tumor cells in vivo (Holden et al 2010; U.S. Pat. No. 7,598,335 to Wang et al.), however, such attempts are limited due to, among other things, their reliance on the enhanced permeability and retention effect (EPR effect) for distribution and imaging sensitivity issues (Shubayev et al. 2009; Arbab et al. 2005). While this approach has improved the MRI detection sensitivity of liver metastases by 95% for example (Senterre et al. 1996), this passive approach has proven inefficient and non-specific distribution causes high background noise (Peer et al. 2007; Gullotti & Yeo 2009; Schluep et al. 2009). Furthermore, some diagnostics aggregate upon being exposed to an MRI field, which can cause embolization. Moreover, tumor specificity is not reliably improved by modifying the surface of the diagnostics to contain tumor-retention peptide sequences (Peer et al. 2007).

To overcome challenges associated with nonspecific distribution, it was previously shown that tumor-tropic stem cells may be labeled with SPIONs by inducing endocytosis (Thu et al. 2009; Frank et al. 2003). One SPION is a FDA approved commercial Feraheme® SPION formulation. Feraheme® comprises a crystalline iron-oxide core coated with biocompatible dextran and is ~17-31 nm in diameter (FIG. 1). While this approach improves distribution accuracy, the sensitivity of detection is limited by the small amount of SPIONs that cells can endocytose (100 pg SPIONs per NSC (Tang et al. 2010)) without impairing viability or altering cell fates (Schafer et al. 2009; Schafer et al. 2007; Tang et al. 2010). Currently, the detection sensitivity of animal MRI is limited to 10 cells per 100 µm voxel (Kraitchman et al. 2003), which allows tracking of NSCs to the primary tumor but leaves isolated invasive tumor cells invisible. Other imaging techniques (e.g., Positron Emission Tomography (PET) or Single Photon Emission Computerized Tomography (SPECT)) are less useful for tracking NSC migration because they do not provide sufficient anatomical context (resolution from 6 mm-1 cm) (Love et al. 2007; MacLauren et al. 2000). Furthermore, most PET and SPECT isotopes are expensive and require special regulatory permissions because they produce harmful radiation. Also, most decay within a few hours and would not be useful to monitor cell migration to tumors over the course of a few days (Brownell et al. 1970).

Therefore, in one embodiment, at least one or more SPIONS or other diagnostic agents entrapped or encapsulated in or otherwise conjugated to the particle, microparticle or nanoparticles. The particles may be engineered to either permanently entrap diagnostic compounds (non-degradable particle compositions may include, but are not limited to, poly(ethylene)glycol diacrylate, poly(ethylene)glycol dimethacrylate, 4-arm poly(ethylene)glycol norbornene, Polystyrene, Polyacrylamide and Silicon, Silk Fibroin); or to release the therapeutics over a controlled timescale only in the immediate vicinity of the tumor (see Table 2) after NSC migration to the tumor and invasive tumor cells has completed. This approach will allow the delivery of diagnostics across the blood brain barrier (BBB) that were not previously deliverable and may provide the ability to improve detection sensitivity by enabling diagnostic quantities to accompany each NSC, particularly for invasive tumor cells that disseminate from the primary tumor.

To entrap diagnostic agents within a non-degradable particle, any suitable method known in the art may be used. Examples of methods that may be used to entrap diagnostic agents within a non-degradable particle may include, but are not limited to, polymerization polymeric particles in the presence of the SPIONS-entrapment, diffusion and penetration of SPIONs into pre-existing polymeric particles and SPION formation within the pre-existing polymeric particle.

Methods of Diagnosing, Monitoring or Treating Pathological Conditions

In some embodiments, methods for diagnosing a pathological condition, treating a pathological condition, or monitoring a response to a treatment or a treatment regiment for a pathological condition are provided. The pathological condition may be any condition associated with a pathological site or entity that may be targeted by a tropic cell as described above and in Table 1. For example, a pathological condition that may be treated, monitored or diagnosed using the methods described herein may include, but are not limited to, cancers, tumors or other proliferative disease (e.g., glioma, medulloblastoma, or other brain cancers), amytrophic lateral sclerosis (ALS), hypoxia, ischemia, muscular dystrophy, osteogenesis imperfect, graft-versus-host disease, subcutaneous wounds, radiation sickness, a viral infection, a bacterial infection, a chronic inflammatory or proliferative disease, a chronic wound, Kaposi's sarcoma, an autoimmune disease (e.g., multiple sclerosis, psoriasis, lupus), inflammation related to tissue damage, wound or injury (e.g., a head injury), dopaminergic dysfunction, Alzheimer's disease, or spinal chord dysfunction.

Cancers, tumors or other related proliferative diseases that may be treated, monitored or diagnosed using the methods described herein may include, but are not limited to, Acute Lymphoblastic Leukemia (ALL), Acute Myeloid Leukemia (AML), Adrenocortical, Carcinoma, AIDS-Related Cancers, Anal Cancer, Appendix Cancer, Astrocytomas, Atypical Teratoid/Rhabdoid Tumor, Central Nervous System, Basal Cell Carcinoma, Bile Duct Cancer, Bladder Cancer, Bone Cancer, Osteosarcoma and Malignant Fibrous Histiocytoma, Brain Stem Glioma, Brain Tumors, Breast Cancer, Bronchial Tumors, Burkitt Lymphoma, Carcinoid Tumors, Central Nervous System Cancers, Cervical Cancer, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Embryonal Tumors, Central Nervous System, Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor Extrahepatic Bile Duct Cancer, Eye Cancer Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST)—see Soft Tissue Sarcoma, Germ Cell Tumor, Gestational Trophoblastic Tumor, Glioma, Hairy Cell Leukemia, Head and Neck Cancer, Heart Cancer, Hepatocellular (Liver) Cancer, Histiocytosis, Hodgkin Lymphoma, Hypopharyngeal Cancer, Intraocular Melanoma, Islet Cell Tumors (Endocrine Pancreas), Kaposi Sarcoma, Kidney cancer, Langerhans Cell Histiocytosis, Laryngeal Cancer, Leukemia, Lip and Oral Cavity Cancer, Liver Cancer (Primary), Lobular Carcinoma In Situ (LCIS), Lung Cancer, Lymphoma, Macroglobulinemia, Male Breast Cancer, Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma, Multiple, Myeloproliferative Disorders, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Oropharyngeal Cancer, Osteosarcoma and Malignant Fibrous Histiocytoma of Bone, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma, Sezary Syndrome, Small Cell Lung Cancer, Small Intestine Cancer, Soft Tissue Sarcoma, Squamous Cell Carcinoma, Squamous Neck Cancer, Stomach (Gastric) Cancer, Supratentorial Primitive Neuroectodermal Tumors, T-Cell Lymphoma, Cutaneous, Testicular Cancer, Throat Cancer, Thymoma and Thymic Carcinoma, Thyroid Cancer, Transitional Cell Cancer of the Renal Pelvis and Ureter, Trophoblastic Tumor, Ureter and Renal Pelvis Cancer, Urethral Cancer, Uterine Cancer, Uterine Sarcoma, Vaginal Cancer, Vulvar Cancer, Waldenström Macroglobulinemia, and Wilms Tumor.

"Diagnosing" or a "diagnosis of" a condition may include, but is not limited to, visualizing said condition using an imaging method. Imaging methods that may be used in accordance with the embodiments described herein may include, but are not limited to, positron emission tomography (PET), computer assisted tomography (CAT), single photon emission computerized tomography, x-ray, fluoroscopy, and magnetic resonance imaging (MRI), each of which may be used with the method for diagnosing or visualizing a disease.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "response to a cancer treatment or treatment regimen" refers to the clinical benefit imparted to a subject suffering from a disease or condition (e.g., cancer) from or as a result of the cancer treatment or treatment regimen. A clinical benefit includes a complete remission, a partial remission, a stable disease without progression, progression-free survival, disease free survival, improvement in the time-to-progression of the disease, improvement in the time to death, or improvement in the overall survival time of the patient from or as a result of the treatment or treatment regimen. There are criteria for determining a response to therapy and those criteria allow comparisons of the efficacy to alternative treatments (see Slapak and Kufe, Principles of Cancer Therapy, in Harrison's Principles of Internal Medicine, $13^{th}$ ed., eds., Isselbacher et al., McGraw-Hill, Inc., 1994).

According to some embodiments, the methods described herein may include, but are not limited to administering a therapeutically effective amount of a pharmaceutical composition to a subject suffering from a pathological condition. The pharmaceutical composition may include any suitable particle-tropic cell conjugate, such as those described above, to target a pathological site or entity associated with the pathological condition. For example, in some embodiments, the pharmaceutical composition includes a delivery vehicle such as an NSC-nanoparticle as described above for diagnosing, treating and monitoring a brain cancer, such as a glioma. The particle-tropic cell conjugate may include a tropic cell coupled to one or more particles, wherein the particles encapsulate or are otherwise associated with a diagnostic agent, a therapeutic agent, or both. Examples of therapeutic and diagnostic agents that may be used in accordance with the methods described herein may include those described above.

A "therapeutically effective amount" or a "therapeutically effective dose is an amount of a compound that produces a desired therapeutic effect in a subject, such as preventing or treating a target condition or alleviating symptoms associated with the condition. The most effective results in terms of efficacy of treatment in a given subject will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{st}$ Edition, Univ. of Sciences in Philadelphia (USIP), Lippincott Williams & Wilkins, Philadelphia, Pa., 2005.

In some embodiments, the pharmaceutical composition may also include a pharmaceutically acceptable carrier. A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Figure 18:
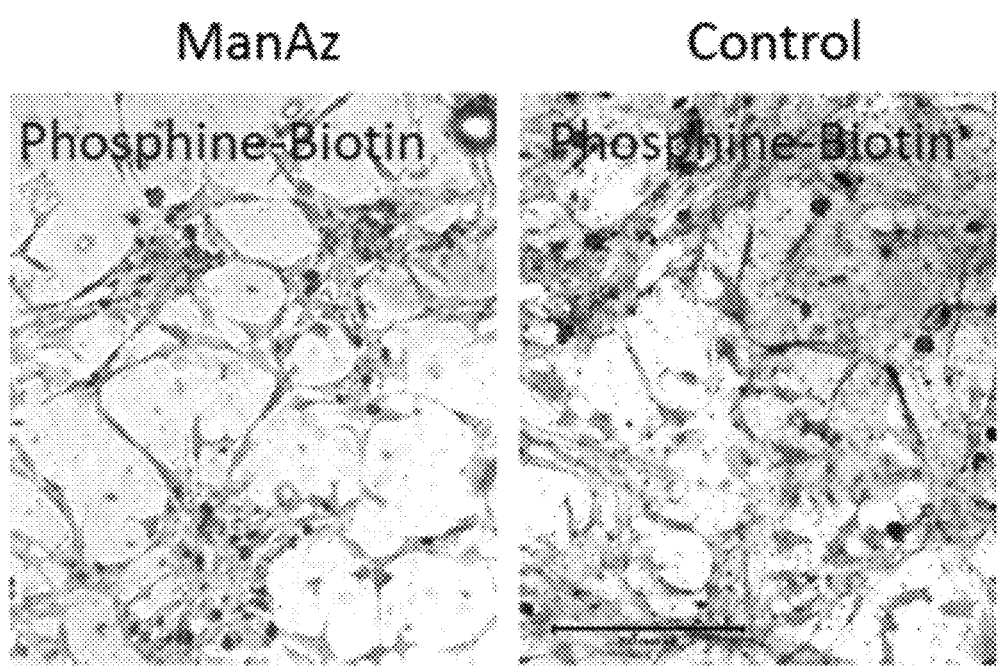
FIG. 18 shows NSCs expressing mannose azide that binds phosphine as an example of another potential coupling mechanism according to some embodiments. The phosphine in this case was biotinylated for visualization using immunological techniques for both unmodified (right panel) and those fed mannose-azide for 7 days (left panel).
Figure 21:
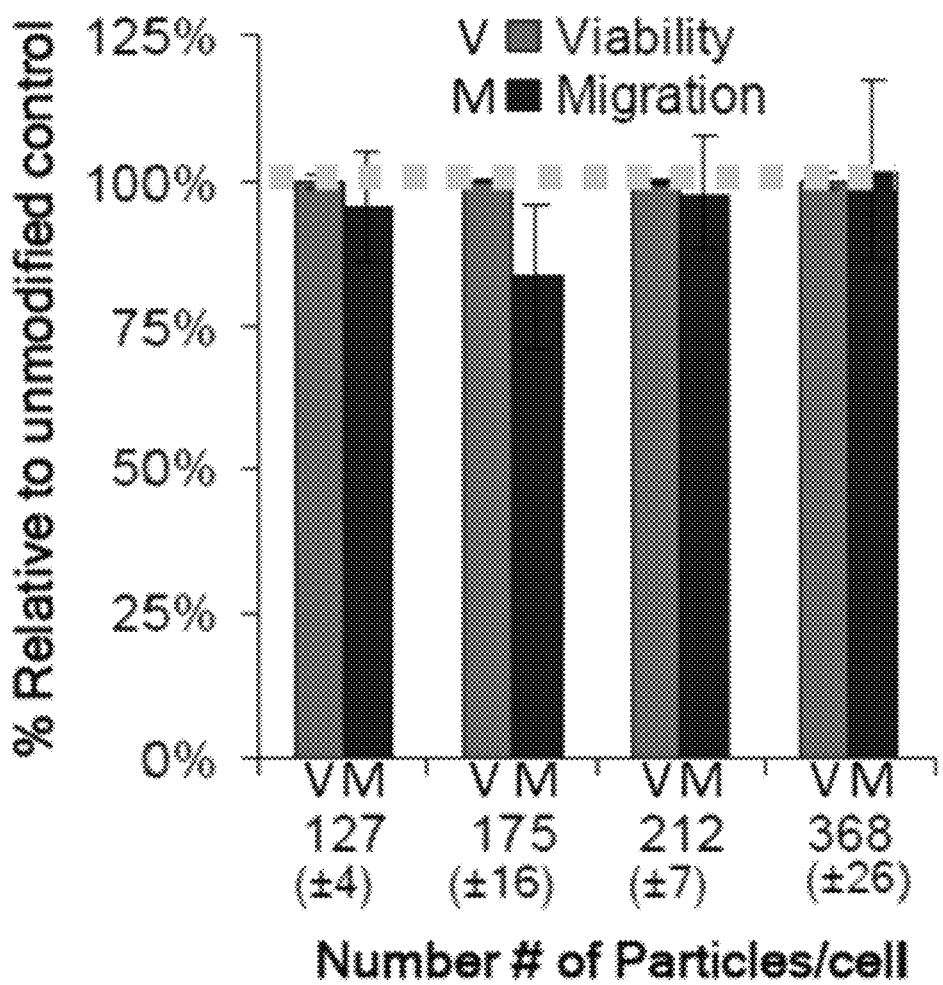
FIG. 21 is a graph illustrating that biotinylation does not affect in vitro viability or tumor tropism of NSCs as compared to a control according to some embodiments. Viability assessments of biotinylated cells were performed using Guava EasyCyte and ViaCount software. Tumor tropism was assessed using a Boyden-chamber migration assay of NSC-nanoparticle conjugates to glioma-conditioned media with BSA as the negative control (not shown).

Example 1: Neural Stem Cell-Nanoparticle Conjugates can Cross the Blood Brain Barrier to Target Intracranial Tumors To determine whether NSCs can be biotinylated and coupled to nanoparticles via avidin without impairing their viability or tumor tropism, NSCs were biotinylated by modifying cell surface sialic acid residues as previously described (Krishnamachari et al. 2008). FACs analysis of avidin-FITC labeled cells showed that 85±9% of cells were biotinylated (FIG. 16) and NSC viability, as determined by determining the percentage of live cells after modification, was not affected by the process of biotinylation (p>0.05) (FIG. 21). Immunostaining results confirmed that the NSCs were efficiently biotinylated (FIG. 17), as surface biotin moieties that were amplified using an avidin and biotinylated horseradish peroxidase macromolecular complex developed upon exposure to DAB substrate. In addition, nestin-expressing NSCs stained positively after incubation with avidin-dsRed. Another example coupling scheme (NSCs expressing exogenous azide bound to phosphine-conjugates) are also demonstrated (FIG. 18).

Figures 19A, 19B, 19C:
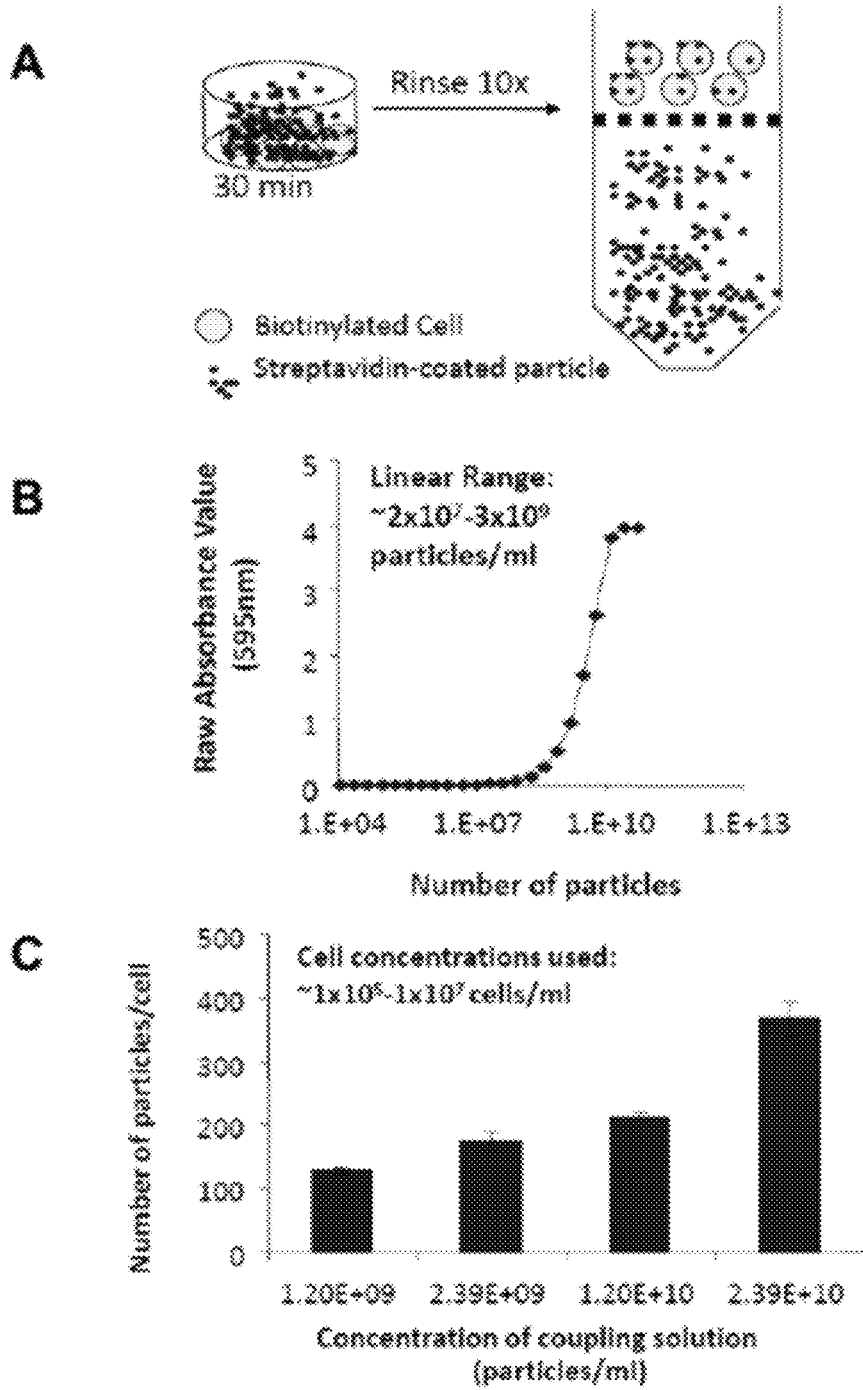
FIG. 19 shows an absorbance based standard curve assay that was used to determine that the number of particles bound to NSCs is dependent upon the concentration of the particle-coupling solution, according to some embodiments.
Figure 20:
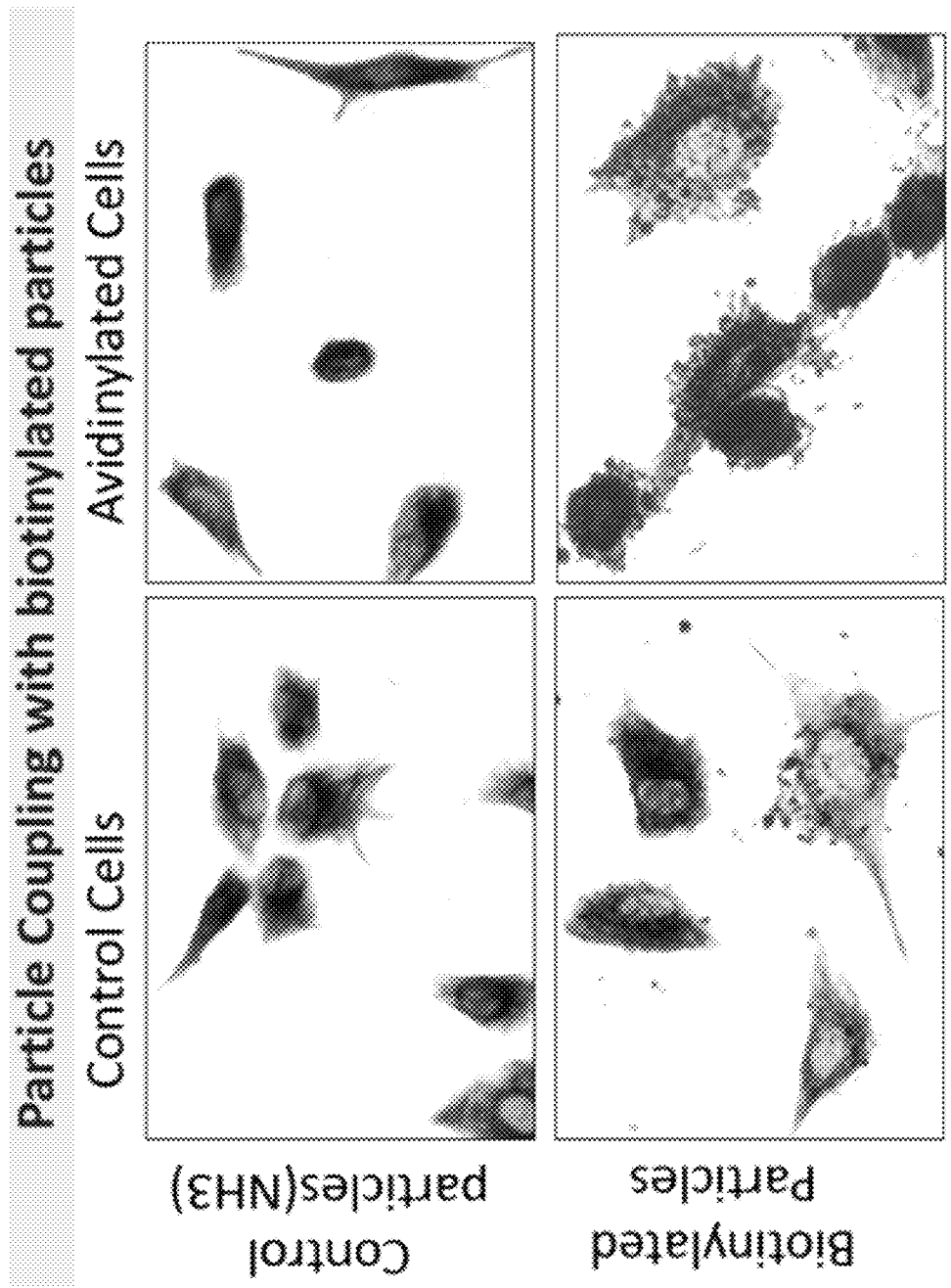
FIG. 20 shows bright-field microscopic images demonstrating NSC-particle hybrids according to some embodiments. Nestin-positive NSCs (either control (left panel) or avidinylated (right panel)) were incubated with Iron-loaded particles containing either control NH3 or Biotin moieties on the surface.

Biotinylated cells were incubated with streptavidin-conjugated nanoparticles (diameter=300 nm) which resulted in the stable addition of an average of <100 nanoparticles/cell (FIG. 19A), and the number of particles per cells increased with increasing concentrations of the particle coupling solution (FIGS. 19B-19C). A lower level of nanoparticle adsorption to unmodified control NSCs was also observed (<15 nanoparticles/cell) (FIG. 20).

Figure 22:
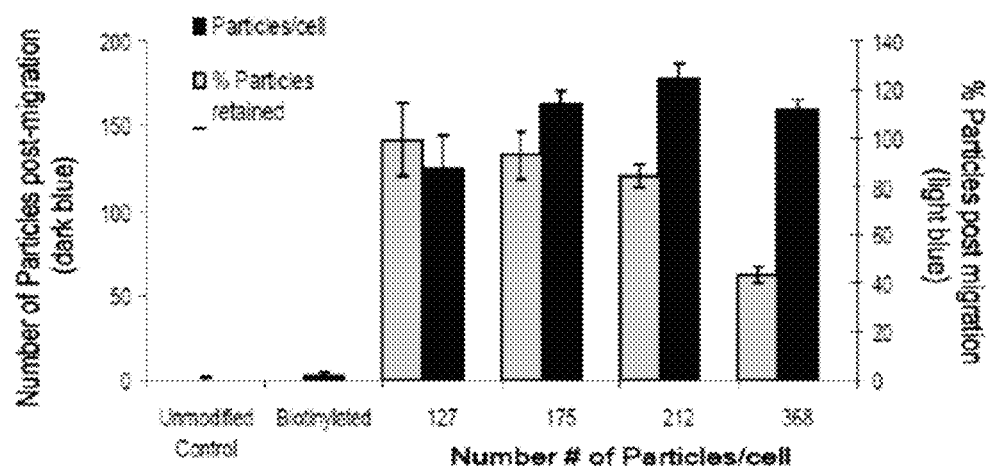
FIG. 22 is a graph illustrating that biotinylation does not affect in vitro viability or tumor tropism of NSCs as compared to a control, according to some embodiments. Viability assessments of biotinylated cells were performed using Guava EasyCyte and ViaCount software. Tumor tropism was assessed using a Boyden-chamber migration assay of NSC-nanoparticle conjugates to glioma-conditioned media with BSA as the negative control (not shown).
Figure 23:
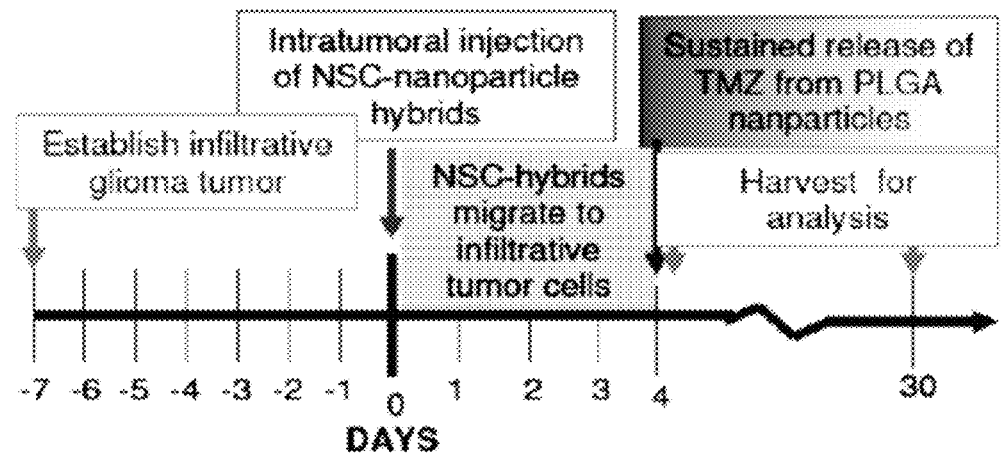
FIG. 23 is a schematic illustrating an NSC-nanoparticle treatment regimen according to some embodiments.
Figure 24:
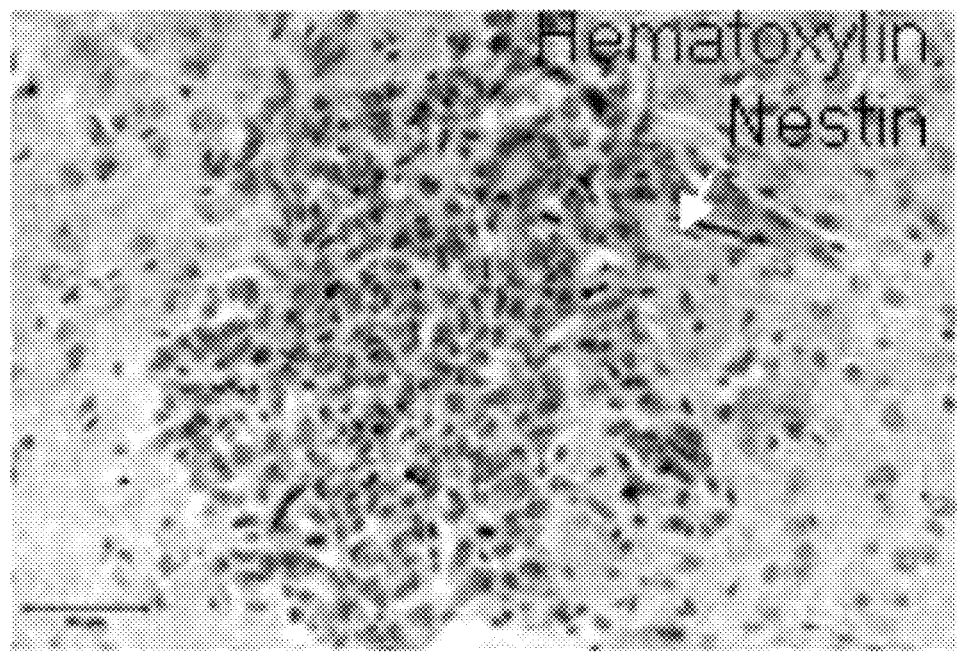
FIG. 24 demonstrates in vivo confirmation of NSC-nanoparticle tumor tropism using a brightfield image of a brain section through a tumor stained with hematoxylin and anti-human nestin according to some embodiments. The arrow indicates an NSC-nanoparticle hybrid intravenously injected 2 days prior to tissue harvesting.
Figure 24:
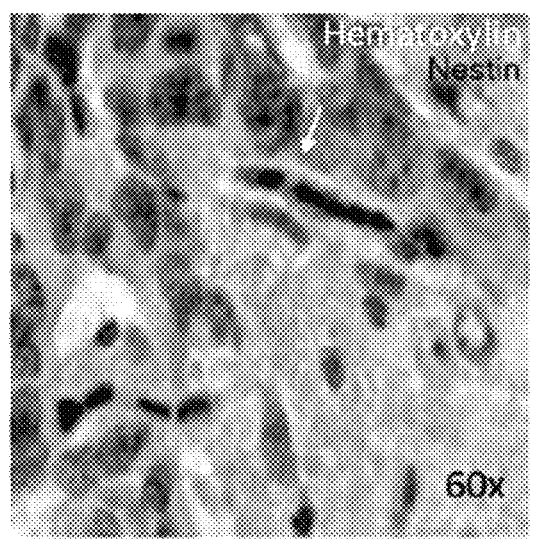
Figure 25:
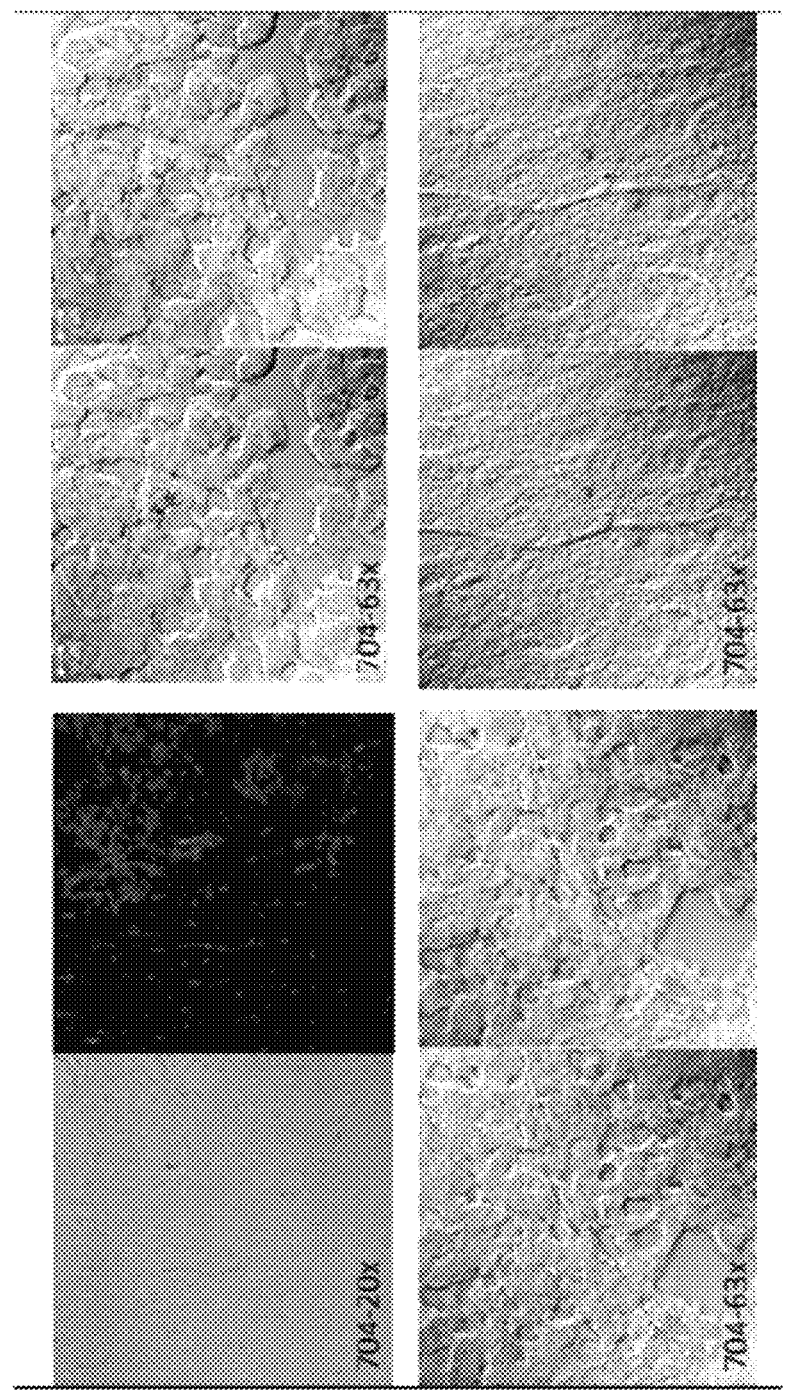
FIG. 25 demonstrates in vivo confirmation of NSC-nanoparticle tumor tropism using a fluorescent/DIC overlay image of a brain section through a tumor stained with DAPI (blue) and anti-human nestin (red) according to some embodiments. The particles appear as dark contrast in the DIC images. Animals were sacrificed 3 days after NSC injection.

To assess if NSC-nanoparticle conjugates maintained tumor tropism in vitro, Boyden-chamber chemotaxis assays were performed as previously described (Aboody et al. 2000). NSC-nanoparticle conjugates retained the ability to selectively migrate to tumor-conditioned media (p>0.05) independent of the number of particles bound (FIG. 21); however, a maximum of ~175 particles/cell was retained post-migration (FIG. 22) suggesting a threshold loading of 175 particles/cell. Preliminary in vivo studies also demonstrated that NSC-nanoparticle conjugates injected intravenously into mice with intracranial syngeneic glioma (FIG. 23) were able to cross the BBB and home to the tumor, as evidenced by the presence of human-nestin positive NSC-nanoparticle conjugates within the tumor (FIGS. 24-25). Together, this data illustrates that NSC-nanoparticle conjugates can be generated without impairing NSC tumor tropism, and that NSC-nanoparticle conjugates can cross the BBB to reach intracranial tumors.

Modifications of these NSC-particle conjugates may be used to enable NSCs to deliver gold-standard small-molecule chemotherapeutics within stimuli-responsive particles directly to invasive glioma, improve retention and tumor-selective distribution of NSC-particle conjugates, and increase the MRI detection sensitivity for SPION-labeled NSCs; as well as enable NSCs to deliver sustained release combinatorial regimens of compounds currently unable to cross the BBB such as targeted immunotoxins. Further, a combination of diagnostic and therapeutic nanoparticle preparations may be loaded onto the same NSCs to allow for simultaneous detection and treatment of invasive tumor cells.

Example 2: Neural Stem Cells Improve Intracranial Nanoparticle Retention and Tumor-Selective Distribution Selective targeting of therapeutic agents to glioma foci could significantly improve patient prognosis. Since intravenously administered therapies exhibit inefficient penetration across the tumor-brain-barrier and within hypoxic tumor regions (Meikle et al. 1998), research efforts are focused on intratumoral drug infusions. The pharmacokinetics of these infusions have been improved through the combined use of therapeutic nanoparticles (NPs) and convection-enhanced delivery (Allard & Benoit 2009). Co-infusions of NPs with digestive enzymes or dialating hypo-osmolar solutions have improved NP penetration into the tumor (Neeves et al. 2007; Sykov & Nicholson 2008). Unfortunately, poor NP retention and off-target toxicities still occur when infused NPs overflow the intended distribution range or get lost along conductive flow paths such as perivascular spaces or white matter tracts (see Brady et al.).

One innovative NP distribution strategy that may improve penetration, retention, and tumor-selective distribution involves coupling NPs to the surface of tumor tropic cells that can home to and penetrate tumors. Adjuvant-loaded NPs have been surface-conjugated to T-cells and hematopoetic stem cells without impairing tropism to peripheral sites in vivo (Stephan et al. 2010). Doxorubicin-loaded NPs have been surface-conjugated to mesenchymal stem cells (MSCs) without impairing MSC viability (Li et al. 2011); however, tropism towards intracranial glioma has not yet been assessed. Because MSCs can contribute to glioma progression (Eskandary et al. 2011); neural stem cells (NSCs) may be safer and more effective in distributing NPs to glioma sites. NPs have not previously been surface-conjugated to NSCs, which was the first objective of the present study.

For the NP-conjugation studies, a human neural stem cell line (HB1.F3 NSCs) currently being used in Phase I clinical studies was used to target a prodrug activating enzyme (Aboody et al. 2011) and endocytosed diagnostic NPs (Thu et al. 2009) to glioma (NCT 1172964). A previously described coupling approach (Krishnamachari et al. 2008)

was used to biotinylate the NSCs (see Kim et al. 2012) which were then coupled to streptavidin-conjugated polystyrene NPs. These NPs were selected for their stability, pre-clinical biocompatibility, commercial availability Mailander & Landfester 2009) and prior use as a generic model of intracranial NP distribution (Chen et al. 2005). The NPs used here (diameter=797.7 nm) exceed the size range (150 nm—300 nm) of surface-conjugated NPs previously distributed in vivo using tropic cells (Stephan et al. 2010; Li et al. 2011). Despite the known importance of chemokine (Kendall et al. 2008), integrin (Ziu et al. 2006; Karp & Teo 2009), and selectin (Karp & Teo 2009) receptors for tumor tropism, it was demonstrated that NP-conjugation has a negligible impact on NSC viability or tropism in vitro.

If the NP-NSC interaction remains stable in vivo, one can expect significant improvements in NP retention. Free-NP injections are subject to perivascular clearance as edema from the initial injection subsides over 1 week (Carare et al. 2008; MacKay et al. 2005). In contrast, viable NSC-coupled NP injections should remain in the extracellular space for at least 30 days (Jackson et al. 2010). Significant improvements in tumor-penetration and tumor-selective NP distribution are also expected because the NPs used here are too large to passively diffuse through intracranial intercellular spaces (38-64 mm), and too large to passively accumulate within tumors due to leaky vasculature (<30-200 nm). The second objective was therefore to utilize immunological techniques and microscopic imaging to determine if NSCs can improve intracranial NP retention, tumor penetration, and tumor-selective distribution in an orthotopic glioma mouse model, following injection immediately adjacent to the tumor, into the contralateral hemisphere, or into the tail vein.

Materials and Methods

Cell Culture.

All cell lines were cultured in Dulbecco's Modified Eagle's Medium (DMEM) (Invitrogen) supplemented with 10% fetal bovine serum (Gemini Bio), 1% I-glutamine (Invitrogen), and 1% penicillin-streptomycin (Invitrogen) and maintained at 37° C. in humidified incubator (Thermo Electron Corporation) containing 6% $CO_2$. Cells were passaged using a 0.05% trypsin/EDTA solution (Invitrogen) at 80% confluency and media was changed every 2-3 days. Glioma cell lines: Firefly Luciferase expressing U251 (U251.ffluc) and U87 human glioma cell lines were obtained from American Type Culture Collection (Rockville, Md.). U87 cells were used to generate tumor cell-conditioned media by replacing culture media with serum-free media when cells were 80% confluent, followed by a 48 hour incubation. Neural Stem Cell lines: The human, v-myc immortalized, HB1.F3 NSC line (Kim et al. 2008) was obtained from Dr. Seung Kim. Extensive characterization studies have demonstrated that the HB1.F3.CD is chromosomally and functionally stable, non-tumorigenic, and minimally immunogenic (HLA class II negative). This cell line was further transduced with lentivirus to stably express green fluorescent protein (eGFP) (Flax et al. 1998 (and used to track stem cell distribution in vivo.

Biotinylation of NSCs.

NSCs were biotinylated as described previously (Krishnamachari et al. 2008). Briefly, cells were grown to 80% confluency, then culture media was removed and cells were washed twice with phosphate buffered saline (PBS) before incubation within a cold 1 mM $NaIO_4$/PBS solution for 20 min in the dark at 4° C. NSCs were washed with PBS at pH 6.5 at room temperature. Next, the cells were incubated in a 0.5 mM biotin hydrazide (Sigma) solution in DMEM (Invitrogen) (pH 6.5) for 90 min at room temperature. The cells were washed twice with PBS solution (pH=7.4).

Biotinylated NSC Surface Characterization.

For Fluorescent Activated Cell Sorting (FACs), Freshly trypsinized biotinylated NSCs cells were re-suspended at $5 \times 10^6$ cells/ml in staining/wash buffer (SWB) (94% PBS [without $Ca^{2+}$ and $Mg^{2+}$], 5% FBS and 0.001% w/v $NaN_3$ (Sigma). Cells were fixed (Fix and Perm kit, Caltag) and rinsed. Control or biotinylated NSCs were immunostained with fluorescien-conjugated avidin at (10 µg/ml) and incubated for 20 min at RT in the dark. After two final rinses with SWB, the cell pellets were re-suspended to $2.5 \times 10^4$ cells/µl in SWB. The number of positive cells were analyzed by flow cytometry (GuavaCyte, Guava Technologies). Representative plot is shown, with mean±stedev listed in the text (3 experiments; n=10 samples). For β1-integrin assessments, control NSCs were immunostained with anti-β-integrin primary antibody (0.01 µg/ml; BD Pharmingen) or mouse IgG1 kappa isotype control antibody (0.01 µg/ml; BD Pharmingen) for 40 min at RT. The samples were then washed twice with SWB, stained with 10 µg/ml of goat anti-mouse-IgG/IgM-FITC (BD Pharmingen) and incubated for 20 min at RT in the dark.

For Immunohistochemistry, control and biotinylated NSCs were rinsed then fixed in 4% paraformaldehyde and processed for immunoperoxidase-3,3'-diaminobenzidine (DAB) staining after quenching endogenous peroxidases with 0.3% hydrogen peroxide/PBS for 30 min. To identify cell surface biotinylation, control and biotinylated NSCs were incubated with Vectastain ABC Elite kit (Vector Laboratories) which builds an avidin-biotin-horseradish peroxidase macromolecular complex in the presence of cell-surface biotin moieties. Antibody reactivity to β1-integrins were detected using the same method after incubating serum-blocked NSCs treated with either a monoclonal anti-β1-integrin or mouse IgG control with a biotinylated anti-mouse IgG secondary antibody.

Nanoparticle Characterization.

Nile-red-loaded, streptavidin-conjugated polystyrene NPs were commercially obtained from (Sphereotech). Nanoparticle size was estimated using dynamic light scattering at a temperature of 25° C. Five measurements were taken following dilution of the nanoparticle dispersion in filtered deinoized water. The surface charge of the nanoparticles in pH 7.4 deionized water was investigated by zeta potential measurement at 25° C.

Coupling of Streptavidin-Conjugated NPs to Biotinylated NSCs.

Biotinylated cells were trypsinized, rinsed once with PBS, then resuspended in a streptavidin-conjugated particle suspension in pH 7.4 PBS. Coupling occurred during a 20 minute incubation at room temperature with periodic tritration of the suspension. The cell-particle mixture was then centrifuged and the uncoupled particles remaining in the supernatant were removed. The cells were rinsed twice in large volumes (12 mls) of PBS to encourage removal of loosely bound particles.

Microscopic Imaging of Surface-Associated NPs In Vitro.

For confocal microscopy, suspensions of NSCs or NSC-NP Hybrids ($1 \times 10^7$ cells/mL) were fixed in 4% Paraformaldehyde, rinsed in 0.1% Tween/PBS, then stained for 15 minutes at room temperature in the dark with a PBS solution containing alexafluor-488 conjugated phalloidin (1:200) to stain cellular filamentous-actin and DAPI (1:1000) to stain cell nuclei. Cells were pelleted and rinsed, then encapsulated within 1% low melting-point agarose (Sigma) to stabilize the cells for imaging. The 200 µl of the agarose suspension was placed on a glass slide and the coverslip used to create a thin gel layer that was polymerized upon exposure to 4° C. for 10 min. Images were acquired using a confocal microscope (Zeiss) equipped with a 100× oil immersion objective. Each image represents a z-stack compiled from 1 μm optical slices spanning the entire thickness of the cell.

For scanning electron Microscopy (SEM), NP surface localization was verified with SEM after growing NSCs or NP-coupled NSCs on glass coverslips for 12 hours then fixed with 1.5% glutaraldehyde in 0.1 M cacodylate buffer. Samples were then sputter coated with gold then imaged using a FEI Quanta 200 scanning electron microscope.

Quantification of Surface-Associated NPs In Vitro.

For FACs, biotinylated NSCs with or without exposure to 0.1% (wt/vol) nile-red labeled, streptavidin-conjugated polystyrene nanoparticles were washed twice, then resuspended in PBS. The increase in red fluorescence as a result of particle binding was quantified using a GuavaCyte FACs cytometer and results analyzed using FlowJo Software (2 experiments; n=8 samples).

For the Fluorimeter:

A standard curve of nile red-particles in PBS measured in the presence of 1e5 cells/ml was used for quantifying the number of NPs bound to NSCs. Control or particle-coupled NSCs were diluted to 1e5 cells/ml either before or after migration, then samples in triplicate were analyzed on a Spectromax M3 fluorimeter using 520 nm excitation and 605 nm emission filters. Plot showing mean±SEM is shown (3 experiments; n=12 samples).

NP-Coupled NSC In Vitro Viability and Tumor Tropism Assessments.

To assess viability, freshly trypsinized cells were labeled with ViaCount a proprietary mixture that distinguishes between viable and non-viable cells based on the differential permeability of DNA-binding dyes within ViaCount. The fluorescence of each dye is resolved using the Guava Easy-Cyte Flow cytometer, and data was analyzed using FlowJo software. Representative plot is shown, with mean±stedev listed in the text (7 experiments; n=9 samples).

To assess tumor tropism, modified Boyden chamber chemotaxis assays were performed using 24 well cell culture plates with polycarbonate inserts will pore diameter of 8 um as described previously (Brown et al. 2003). 5% BSA/DMEM, and conditioned media from tumor cell lines was added to the lower chamber of 24-well plates (500 μl/well, triplicate samples). Inserts were placed into wells and suspensions of NSCs or NP-coupled NSCs were added to the upper chamber ($5\times10^4$ cells/250 μl suspended in 5% BSA/DMEM to each well). After incubation for 4 hours at 37° C., the cells that did not migrate were removed from the inner surface of the filter. The membrane tray was then placed in a new lower chamber containing pre-warmed Accutase (Sigma-Aldrich) at 37° C. for 10 min. Detached cells in the buffer were then transferred to a V-bottom 96 well plate and centrifuged at 1500 rpm for 5 min. The buffer was aspirated, cells were labeled with Viacount, and counted using Guava EasyCyte flow cytometer. Plot showing mean±SEM is shown (4 experiments; n=12 samples).

In Vivo Glioma Xenografts and NP Injections.

Esterase-deficient SCID mice were anesthetized with an intra-peritoneal injection of 132 mg/kg Ketamine and 8.8 mg/kg Xylazine. Animals were then immobilized in a stereotactic apparatus and received stereotactically-guided intracranial 2 μl injections 2 mm lateral, 0.5 mm anterior to bregma, tracked from a depth of 2.5 mm to 2.25 mm to 2.0 mm; 0.667 μl of cell suspension was injected at each level. Intracranial injections contained either 1) Free-NP ($3.5\times10^7$ NPs), 2) NSC-coupled NPs ($2\times10^5$ cells, $3.5\times10^7$ NPs), or 3) U251 human glioma cells ($5\times10^4$ cells). Injections were performed with a 30-gauge 5-μl hamilton syringe over 3-5 minutes. After retracting the needle over 2-4 minutes, bone-wax was used to occlude the burr hole, and skin was closed with skin glue. Intravenous NP injections contained 200 μl of either free-NPs ($3.5\times10^8$ NPs) or NSC-coupled NPs ($2\times10^6$ cells, $3.5\times10^8$ NPs). Buprenorphine analgesic was administered subcutaneously at 0.05 mg/kg to relieve post-operative pain. Results were obtained from 3 different experiments that resulted in 3 mice per group receiving free-NP injections, and 4-6 mice per group receiving NP-NSC injections. When injecting NPs in the presence of glioma xenografts, tumor injections were performed 7 days prior to NP injections. When mice appeared to be in discomfort or distress as judged by independent animal care personnel, animals were euthanized consistent with the recommendations of the Panel of Euthanasia of the American Veterinary Medical Association. Mice were housed in an AALAAC-accredited facility and were given food, water, and libitum.

Tissue Harvesting and Processing.

Mice were sacrificed 1 or 4 days post-NP injection by $CO_2$ asphyxiation and transcardially perfused with PBS followed by 4% paraformaldehyde (pH 7.4). Brains, liver and spleen were removed and further fixed by immersion in 4% paraformaldehyde for 24 h before sinking in 30% sucrose for 48 h. The tissues were frozen in TissueTek OCT (Sakura inetek Europe B.V.) and sectioned coronally on a cryostat (Leica 17-20). Sections were collected on a positively-charged slides (Fisher) for histological examination, quantification studies and immunocytochemistry. 20 sections taken in 100 um levels were obtained from each liver and spleen.

Tissue Imaging. Every $5^{th}$ section was stained with 4',6-diamidino-2-phenylindole (DAPI) (Sigma Biochemical) (1 μg/ml), rinsed and mounted with fluorescent mounting medium (DAKO) then examined under a fluorescence microscope. DAPI fluorescence was detected using epifluorescence excitation/emission filters of 340-380/420 nm (LP) (UV-2A, Nikon). HB1.F3.C1.eGFP NSCs were detected suing an epifluorescence filter (465-495 nm excitation, 515-555 nm emission; B-2E/C). Red NPs were detected using excitation/emission filters of 540-580 nm and 600-660 nm (Y-2E/C). Images of the injection and tumor site were obtained using equivalent exposure were obtained using a Nikon Eclipse TE2000-U microscope (Nikon Instruments) equipped with a SPOT RT Slider digital camera (Diagnostic Instruments). Images were recorded and stored using SPOT Advanced and Adobe Photoshop software. Open source Reconstruct software was used to construct 3D projections of NP distribution within the injection and tumor sites Fiala JC (2005) Reconstruct: a free editor for serial section microscopy. J Microscopy 218:52-61.

Tumor presence in DAPI stained slides was obvious from the dense, large glioma nuclei, but was confirmed using immunohistochemistry with a polyclonal antibody generated in rabbit against firefly luciferase protein (MBL International). Sections were rinsed, permeabilized with 0.3% Triton X-100/PBS for 30 min and incubated in blocking solution (5% BSA+3% normal horse serum+0.1% Triton X-100) for 1 hour. Sections were then incubated sequentially with primary antibody (1:250 dilution) for 24 h at 4° C., then a biotinylated goat anti-rabbit IgG (Vector Laboratories) that was amplified for 1 hour using Vectastain ABC Elite kit (Vector Laboratories) and developed upon exposure to DAB substrate (Vector Laboratories). Adjacent sections were also stained with hematoxylin and eosin.

Dark-field hyperspectral imaging was performed using a CytoViva dark field microscope system (Auburn, Ala.) equipped with CytoViva Hyperspectral Imaging System 1.2. First, a spectral signature library was created by scanning a reference sample of a Polystyrene Nanoparticles with the hyperspectral imaging system. The library was then mapped onto images of interest using the mapping method, spectral angel mapper, provided by the ENVI hyperspectral analysis software. PSt NPs only, PSt NPs on Tissue and Tissue without PSt NPs were used as controls.

Statistical Analysis.

Data are presented as mean±SEM unless otherwise stated. Statistical significance was determined using students t-test (* $p<0.1$,  $p<0.05$, * $p<0.01$).

Results and Discussion

NSC-NP Coupling.

Figures 26A, 26B, 26C, 26D:
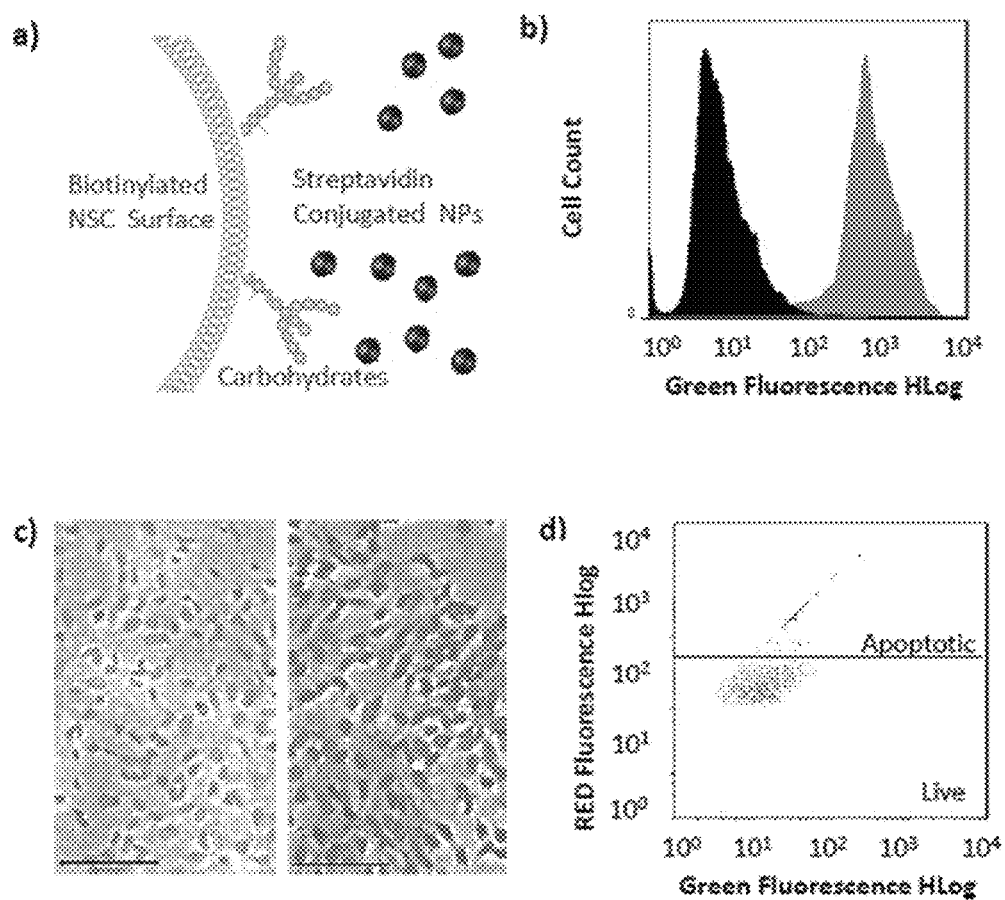
FIG. 26 illustrates NSC biotinylation and NP coupling according to one embodiment. A) Schematic depicting the bond between biotinylated NSCs and streptavidin-conjugated NPs that will stabilize NPs on NSC surface. B) Flow cytometric analysis of control NSCs (black) modified to contain exogenous cell surface biotin moieties (gray) detected by fluorescein-conjugated avidin. C) Brightfield microscopic images of hematoxylin-stained NSCs (left panel) and biotinylated NSCs (right panel) that were incubated with an avidin-horseradish macromolecular complex that develops brown upon exposure to DAB substrate. Scale bar=100 µm. D) Flow cytometric analysis of live or dead (propidium iodide+) cells. E) Flow cytometric analysis of biotinylated NSCs (black) after incubation with nile red-labeled streptavidin-conjugated nanoparticles (gray). F) Fluorometric determination of the dose-dependant increase in nanoparticle binding to biotinylated NSCs when coupled using solutions containing increasing nanoparticle concentrations. Representative images of control NSCs (upper panel) and biotinylated NSCs+NPs (lower panel) are shown in (G-H). (G) is a Confocal image showing a z-stack projection spanning the entire thickness of each cell, complied from optical slices acquired every 1 µm along the z-axis? Cells were stained with phalloidin and DAPI to visualize the nucleus and cytoskeleton, respectively. The right panel shows a single optical slice from the z-stack shown in the left panel. Scale bar=10 µm. (H) shows SEM images demonstrating NP distribution on the NSC surface Scale bar=5 µm.

NSC-NP coupling was achieved by incubating streptavidin-conjugated NPs with biotinylated NSCs (FIG. 26A). The NPs were characterized to assess the average effective particle diameter (797.7 nm with a 0.0137 polydispersity index value), and surface charge of $-21.32\pm3.20$ mV. NSCs were biotinylated as previously described (Krishnamachari et al. 2008) with no significant impairment in cell viability (96±2% live cells) observed, and 82±10% of the cells contained biotin moieties (FIG. 26B-26C). Each NSC contained an average of $3.64\pm1.1\times10^7$ biotin moieties as determined using the HABA-avidin competition assay.

Figures 26E, 26F, 26G, 26H:
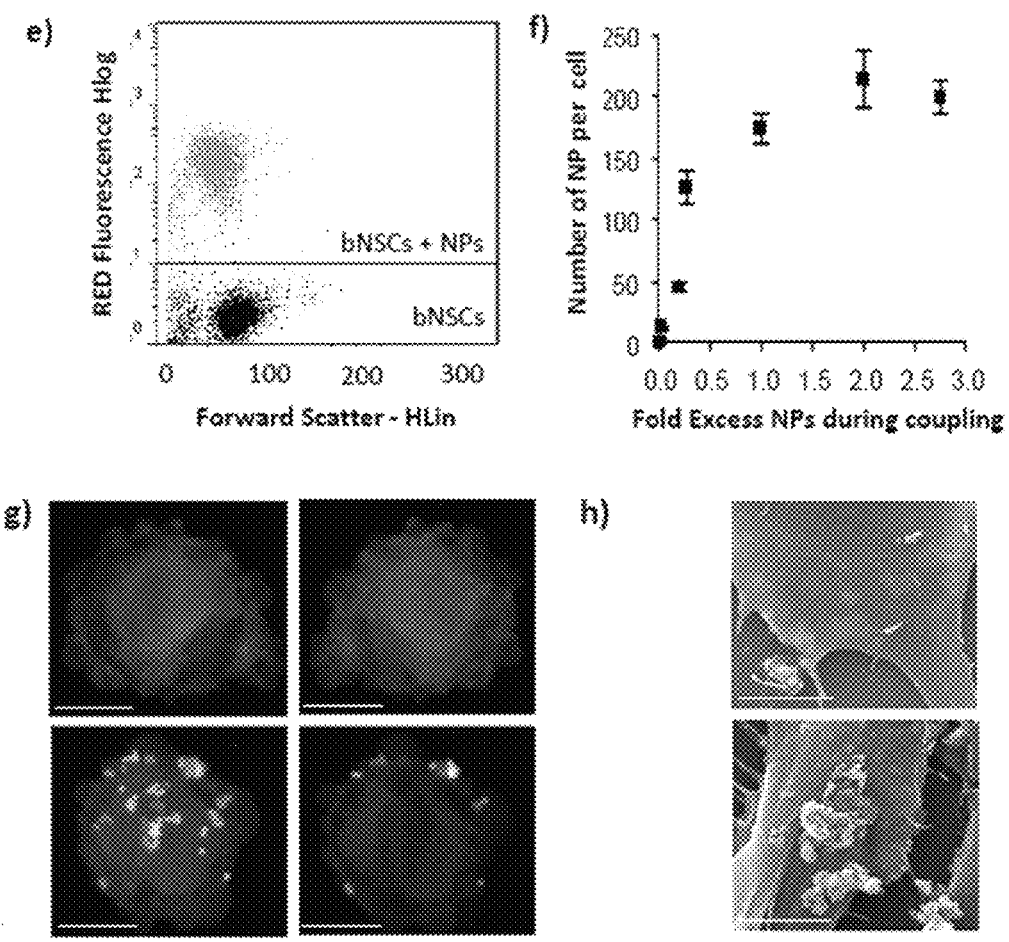

Cell viability was not significantly impaired (92±7% live) (FIG. 26D) after biotinylated NSCs were incubated in a NP suspension at an initial coupling ratio of 1 particle per biotin moiety. After extensive rinsing, 98±2% of NSCs contained surface-associated NPs as assessed by FACs analysis (FIG. 26E). Fluorimetric quantification was used to determine that there were 175±12 NPs per NSC (FIG. 26F) at a 1:1 biotin moiety:NP coupling ratio, and that the number of NSC-coupled NPs can be modulated by adjusting this ratio (FIG. 26F).

When injected in vivo, most NSCs arrive at tumor foci within 50 minutes (<10% increase over the next 1-2 weeks) (Kim et al. 2010). Confocal microscopy was performed 1 hour after coupling to analyze cellular NP localization after this critical 50 minute period. To distinguish intracellular from extracellular located NPs, the cellular cytoskeleton was visualized using Alexafluor 488-phalloidin conjugate. Images reveal that particles reside on the NSC surface (FIG. 26G), suggesting that NPs can be transported to the tumor while still on the NSC surface.

Scanning electron microscopy (SEM) provided higher resolution images that demonstrate that the NPs are attached to the NSC surface in clusters. Some of these clusters are entangled by microvilli (FIG. 26H). These aggregates may form before NSC binding due to coagulation of charged NPs with polymeric serum proteins, or may form due to clustering of biotin moieties on the NSC surface (Lorenz et al. 2008; Kim et al. 2012).

NP-Coupled NSCs Retain Tumor Tropism In Vitro.

Figures 27A, 27B, 27C:
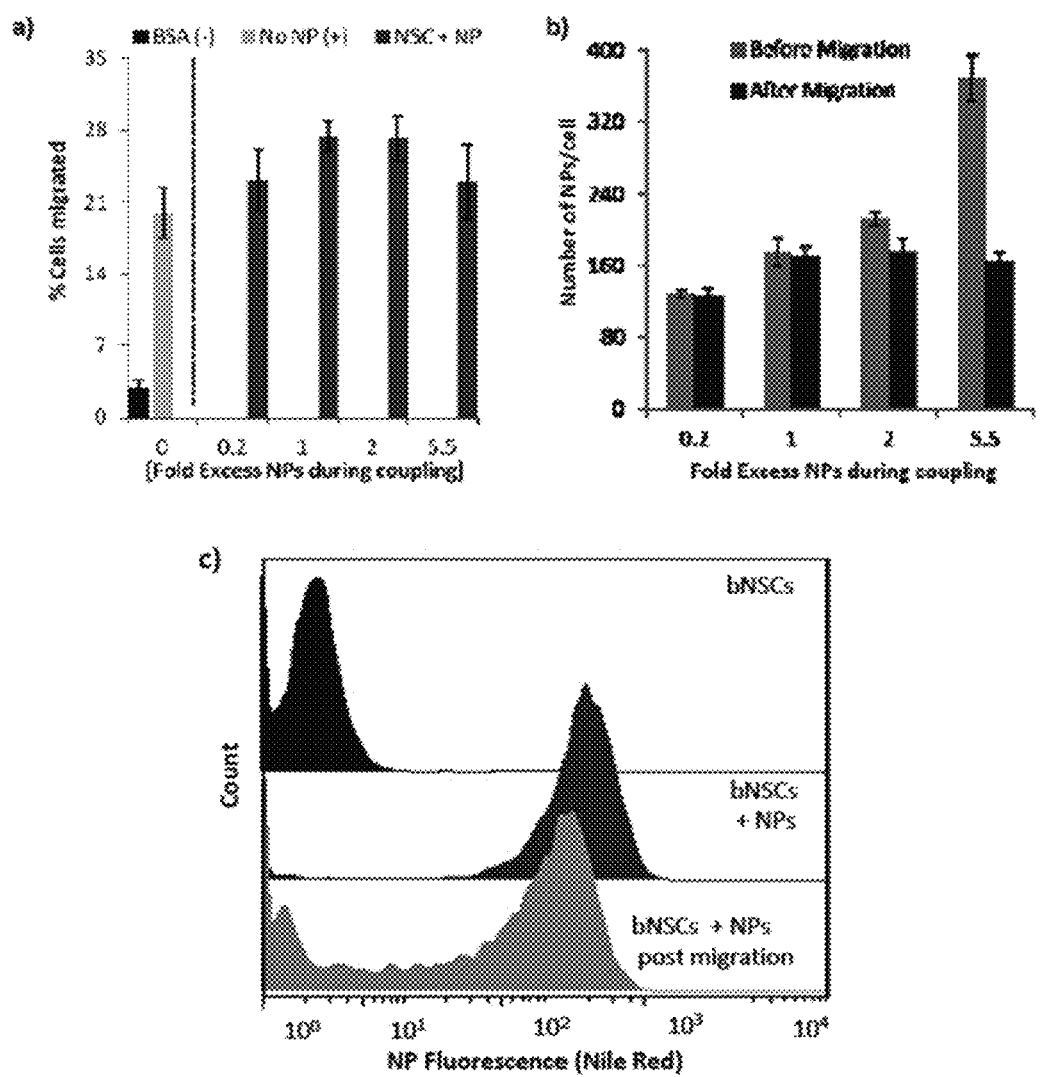
FIG. 27 illustrates that nanoparticle coupling does not affect NSC migration in vitro according to one embodiment. A) Transmigration of control (left of dotted line) or particle coupled NSCs (right of dotted line) seeded in the upper well of a transwell chamber after addition of glioma conditioned media (light and dark gray bars) or BSA-containing negative control media (black bar) into the lower chamber. The fraction of transmigrating NSCs is shown. B) Quantitative fluorimetry was used to determine the number of particles per NSC before (gray bars) and after (black bars) migration after coupling with solutions of increasing NP concentrations. C) The fluorescence profile of NSC-bound NPs before (black) and after (dark gray) coupling at a 1:1 NP:biotin moiety ratio are shown. Particle retention after transmigration is seen with the fluorescence profile of surface bound NPs after migration (light gray).
Figures 32A, 32B, 32C, 32D:
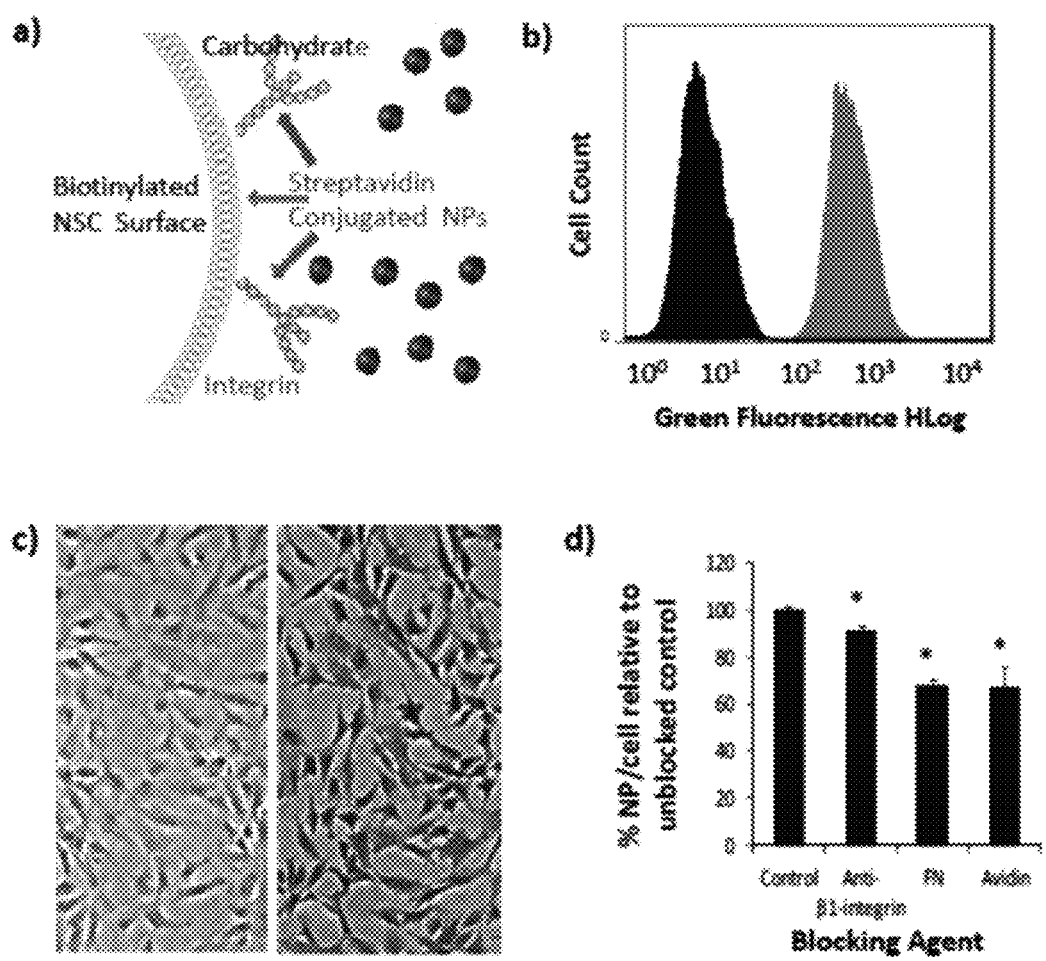
FIG. 32 illustrates non—specific bonding mechanisms that may contribute to NSC-NP binding according to one embodiment. Schematic depicting three different bonding mechanisms between biotinylated NSCs and streptavidin-conjugated NPs that will stabilize NPs on NSC surface: green arrow=the strong, specific biotin-streptavidin bond; red arrow=the interaction between cell surface integrins and RYD-peptides within streptavidin; and blue arrow=adsorption of polystyrene to cells (A). Flow cytometry analysis confirming the presence of endogenous cell surface β1-integrins on NSCs incubated either with a monoclonal β1-integrin antibody (gray) or a mouse IgG control (black) then detected indirectly using an alexafluor 488-conjugated anti-mouse secondary antibody (B). Brightfield microscopic images of hematoxylin-stained NSCs (both panels) that were incubated either with a monoclonal β1-integrin antibody (right panel) or a mouse IgG control (left panel) before standard histological staining (C). Scale bar=100 µm. Adsorption may also be a prominent cause for interaction given incomplete blockage of particle binding when cell surface biotin moieties or integrins are blocked using avidin, or anti-β1-integrins/Fibronectin (FN) respectively (D).

A Boyden-chamber transmigration assay was used to test if NP-coupled NSCs retained their ability to migrate through a membrane towards media enriched with tumor-derived cytokines. Media containing bovine serum albumin (BSA) only was used as a negative control. Results demonstrate that NSCs coupled using increasing NP concentrations had unaltered ($p>0.01$) transmigration efficiencies compared to control NSCs (FIG. 27A). After migration, NSCs retained a maximum of 169±11 NPs per cell even when initially associated with more (FIG. 27B). While higher levels of particle coupling have been reported (e.g., 1500 NPs per cell; Li et al. 2011), their ability to remain bound post-migration was not assessed. FACs analysis demonstrated that 73±3% of cells retained particles after migration (FIG. 27C) when coupled at a ratio of 1 NP: 1 biotin moiety. Not all the NP retention can be attributed to the biotin-streptavidin bond, as non-specific, weaker bonding mechanisms such as streptavidin-integrin interactions (Alon et al. 1993) and passive adsorption of polystyrene to the cell surface (Mailander & Landfester 2009) also contribute to NP-NSC particle binding in vitro (FIG. 32). However, it is the high specificity and affinity of the streptavidin-biotin bond ($Kd\approx4\times10^{-14}$ M; Holmberg et al. 2005) that is expected to stabilize the NP-NSC interaction in vivo despite the shear forces present during transit to the tumor.

NSCs Improve NP Retention In Vivo.

Figures 28K, 28L:
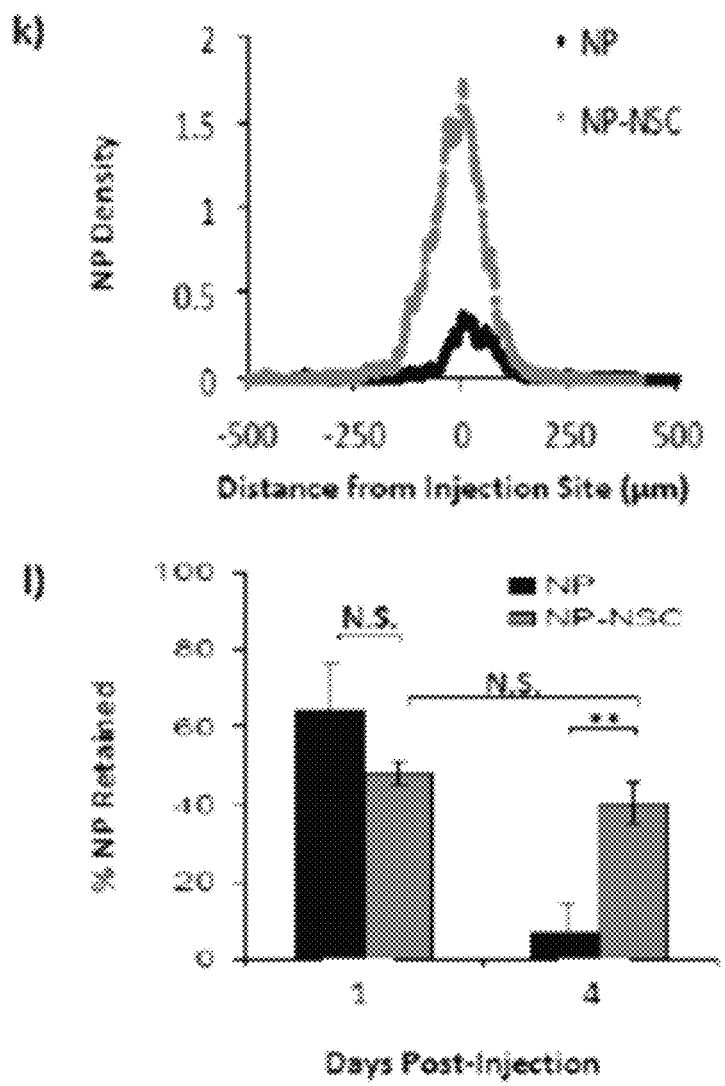
FIG. 28 shows the comparison of free—NP and NSC—coupled NP distribution in tumor—free brains according to one embodiment. Schematic depicting injection paradigm for upper (A) and lower (B) panels. C-F) Brains were sectioned and every 5th section throughout the entire injection site was imaged using fluorescence microscopy either 1 (C, E) or 4 (D, F) days after NP injection. A representative 10× red-green merged image of slices that contained the greatest surface area of red particles is shown. Scale bar=100 µm. G-J) 3D reconstruction software was used to align the sections, map the particle distribution in each slice and assemble a 3D projection of particle distribution around the injection site. Scale bar=100 µm. K) Reconstructed 3D projections were compressed into a single z-stack image, and Image J software was used to map the particle distribution. The density of particles as a function of distance from the injection site is plotted for representative brains on day 7. L) Image J software was used to quantify the surface area occupied by NPs in each slice and the volume of NPs within the brain was estimated considering the interslice distance. This volume was compared to the known volume of NPs initially injected in the brain to determine the % NPs retained on day 1 and 4. Asterisks indicate statistically significant difference (** $p<0.05$).
Figures 29A, 29B, 29C, 29D, 29E, 29F, 29G, 29H, 29I, 29J, 29K:
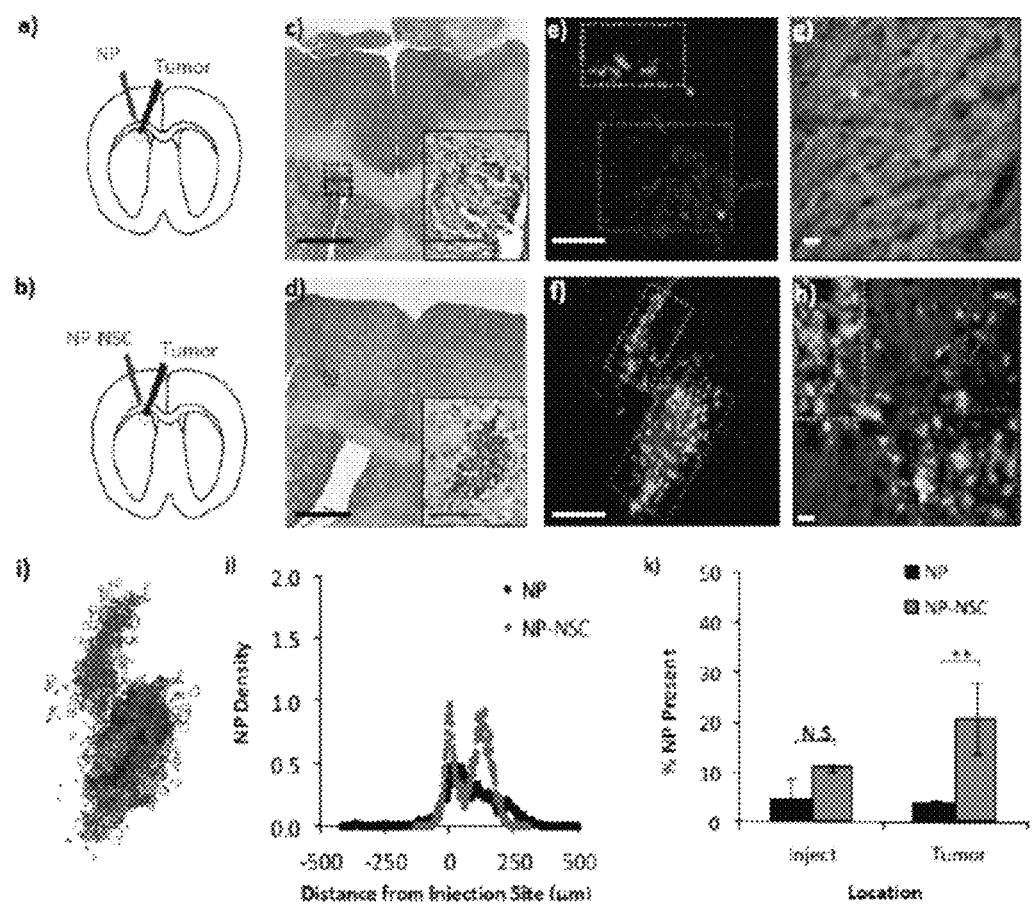
FIG. 29 shows the comparison of free—NP and NSC—coupled NP distribution when injected immediately adjacent to intracranial glioma according to one embodiment. Schematic depicting injection paradigm for upper (A) and middle (B) panels. Four days after NP injection, brains were sectioned and every 5th section throughout the entire injection and tumor site was imaged using fluorescence microscopy. The slice that contained the greatest surface area of red particles was identified and adjacent sections were used for hematoxylin and eosin staining (C, D) (scale bar=500 uM); as well as immunohistochemistry for anti-ffluc (insets in c,d) (scale bar=100 µm) to confirm the presence of tumor cells. Representative 20× fluorescent red-green-blue merged images are shown (E, F) (scale bar=100 µm). Tumors are visible with the dense clusters of blue DAPI-stained nuclei. The presence of polystyrene NPs was further confirmed by imaging on a darkfield microscope equipped with a 60× objective (G, H). Polystyrene NPs were identified based off their unique spectral profile, then pseudo-colored red to ease visualization (scale bar=10 µm). 3D reconstruction software was used to align the sections; map the particle distribution and tumor area in each slice, then assemble a 3D projection of particle distribution around the injection site and tumor (I). Reconstructed 3D projections with exclusion of the tumor volume were compressed into a single z-stack image, and Image J software was used to map the particle distribution (J). The density of particles as a function of distance from the injection site is plotted for representative brains on day 4. Image J software was used to quantify the surface area in each slice occupied by NPs both at the injection and tumor sites, then the volume of NPs within the brain was estimated considering the interslice distance (K). This volume was compared to the known volume of NPs initially injected in the brain to determine the % NPs retained on day 4. Asterisks indicate statistically significant difference (** $p<0.05$).
Figures 30A, 30B, 30C, 30D, 30E, 30F, 30G, 30H, 30I, 30J:
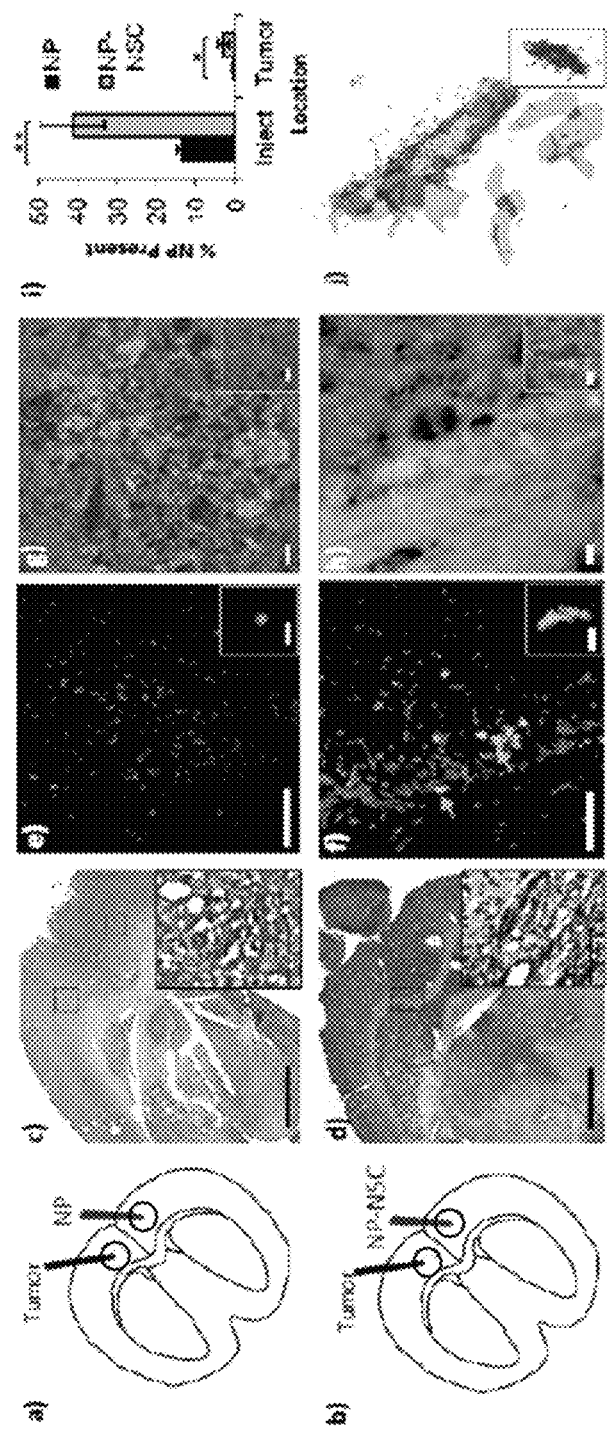
FIG. 30 shows the comparison of free—NP and NSC—coupled NP distribution to an intracranial glioma when injected in the contralateral hemisphere according to one embodiment. Schematic depicting injection paradigm for upper (A) and lower (B) panels. Four days after NP injection, brains were sectioned and every 5th section throughout the entire injection and tumor site was imaged using fluorescence microscopy. The slice that contained the greatest surface area of red particles was identified and adjacent sections were used for hematoxylin and eosin staining (C, D) (scale bar=500 uM); as well as immunohistochemistry for anti-ffluc (insets in C, D) (scale bar=100 µm) to confirm the presence of tumor cells. Representative 20× fluorescent red-green-blue merged images are shown (E, F) (scale bar=100 µm). Tumors are visible with the dense clusters of blue DAPI-stained nuclei. Red fluorescence from NP remaining at injection site is shown in inset (scale bar=100 µm). The presence of polystyrene NPs was further confirmed by imaging on a darkfield microscope equipped with a 60× objective (G, H). Polystyrene NPs were identified based off their unique spectral profile, then pseudo-colored red to ease visualization (scale bar=10 µm). Injection site is shown in inset (scale bar=20 µm). Image J software was used to quantify the surface area in each slice occupied by NPs both at the injection and tumor sites, then the volume of NPs within the brain was estimated considering the interslice distance (I). This volume was compared to the known volume of NPs initially injected in the brain to determine the % NPs retained on day 4. Asterisks indicate statistically significant difference (** $p<0.05$, * $p<0.1$). 3D reconstruction software was used to align the sections, map the particle distribution and tumor area in each slice, then assemble a 3D projection of particle distribution around the injection site and tumor (J).
Figures 31A, 31B, 31C, 31D, 31E, 31F, 31G, 31H, 31I, 31J:
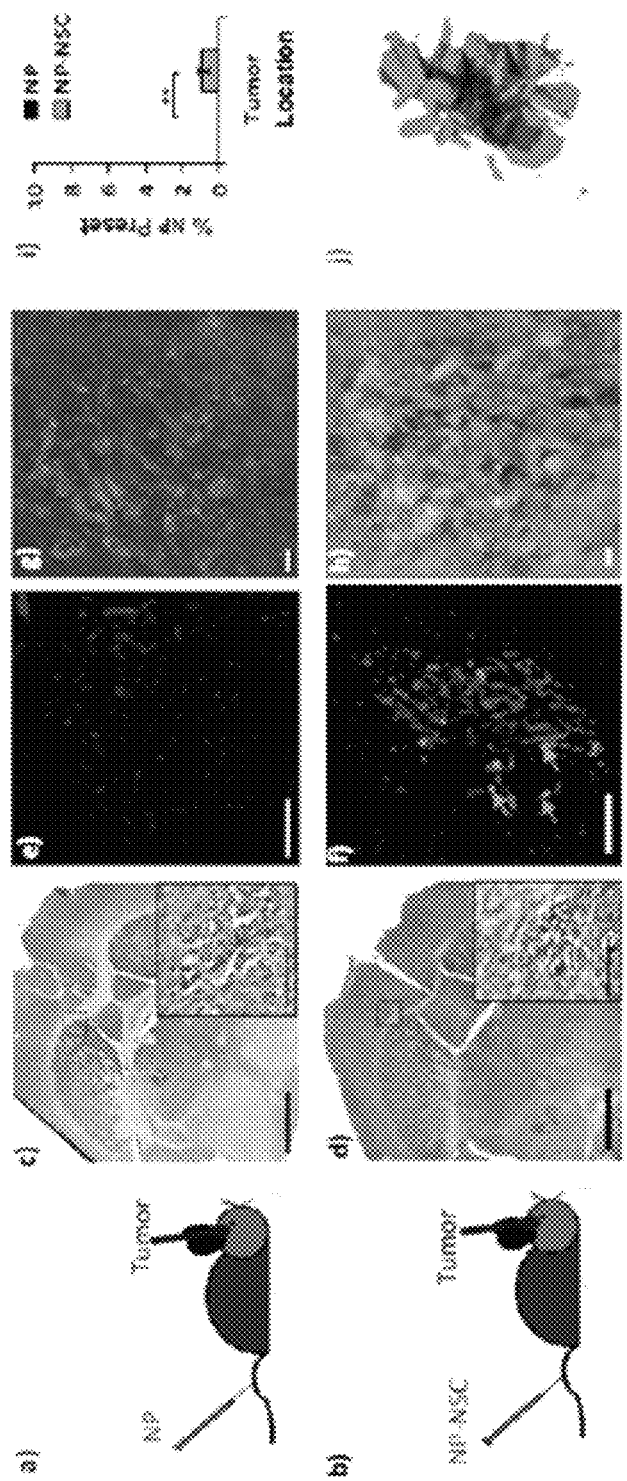
FIG. 31 shows the comparison of free—NP and NSC—coupled NP distribution to an intracranial glioma when injected intravenously according to one embodiment. Schematic depicting injection paradigm for upper (A) and lower (B) panels. Four days after NP injection, brains were sectioned and every 5th section throughout the entire injection and tumor site was imaged using fluorescence microscopy. The slice that contained the greatest surface area of red particles was identified and adjacent sections were used for hematoxylin and eosin staining (C, D) (scale bar=500 uM); as well as immunohistochemistry for anti-ffluc (insets in C, D) (scale bar=100 µm) to confirm the presence of tumor cells. Representative 20× fluorescent red-green-blue merged images are shown (E, F) (scale bar=100 µm). Tumors are visible with the dense clusters of blue DAPI-stained nuclei. The presence of polystyrene NPs was further confirmed by imaging on a darkfield microscope equipped with a 60× objective (G, H). Polystyrene NPs were identified based off their unique spectral profile, then pseudo-colored red to ease visualization (scale bar=10 µm). Image J software was used to quantify the surface area in each slice occupied by NPs both at the injection and tumor sites, then the volume of NPs within the brain was estimated considering the interslice distance (I). This volume was compared to the known volume of NPs initially injected in the brain to determine the % NPs retained on day 4. Asterisks indicate statistically significant difference (** $p<0.05$). 3D reconstruction software was used to align the sections, map the particle distribution and tumor area in each slice, then assemble a 3D projection of particle distribution around the injection site and tumor (J).
Figures 33A, 33B, 33C, 33D:
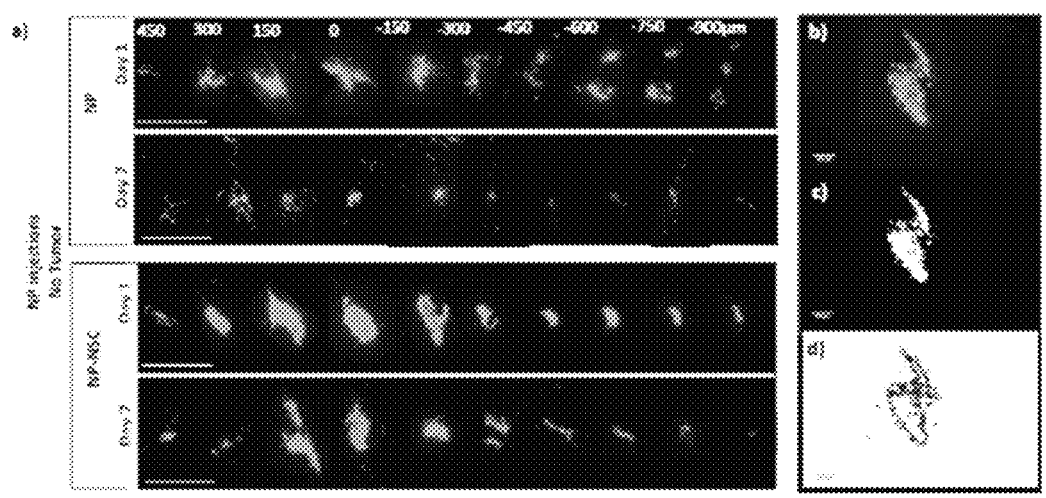
FIG. 33 shows the results of a suspension of NPs or NSC-NPs that were injected a maximum depth of 2 mm into the brain in a 3 different levels spaced 0.667 um apart according to one embodiment. Two minutes elapsed between each injection to minimize backflow through the needle track. In both tumor-free and tumor inoculated brains, nanoparticles distribution was determined by capturing a red-only fluorescent image of the NP injection site or tumor site within every 5th section of the brain. A) Representative distributions of 2 ul of fluorescently labeled polystyrene particles within tumor-free mouse brains sections. B) In both tumor-free and tumor containing brains, each fluorescent image (B) was converted into a binary image (C) with a threshold operation using Image J software. Pixels exhibiting at least 10% of the maximum fluorescence were included, and used to calculating the surface area occupied by NPs (D). A similar analysis approach was used by Neeves et al. Brain research 1180, 2007, 121-132. The surface area was integrated with the interslice distance to estimate the volume of particles within the brain.

To see if the NP-NSC interaction remained stable enough for NSCs to improve NP retention in vivo, NP distribution was observed in a tumor-free brain both one and four days after injecting either free NPs or NPs coupled to green fluorescent protein (eGFP) expressing NSCs (FIG. 28A-28B). Fluorometric quantification was used to ensure equal NP quantities were injected in each case. One day post-injection, brains were harvested, cryo-sectioned, and every $5^{th}$ section throughout the injection site was imaged using fluorescence microscopy (FIG. 33). Using only the red channel, the surface area occupied by NPs in each section was quantified, and the interslice distance was used to estimate the volume of NPs retained within the brain. This value was compared to the known volume of NPs initially injected in order to determine the NPs retained (FIG. 28L). Representative images are shown of sections that contained the largest NP surface area (FIG. 28C-28F). To visualize the cumulative particle dispersion, a 3D reconstruction of the entire injection site was performed and a z-stack image is also shown (FIG. 28G-H).

Day 1 results show no significant difference in NP retention; with 64±12% of free NPs and 48±8% of NSC-coupled NPs retained. Achieving intracerebral cellular or particulate injections without significant loss (34-40% on average (see Brady et al.) due to reflux is a recognized problem (Krauze et al. 2005; Hansen et al. 2010). The NPs are initially found as a mass near the injection site with some isolated NPs dispersed further away. The number of dispersed NPs was 2 fold higher in brains that had been injected with free-NPs as compared to NSC-coupled NPs; however no other notable differences were observed. In both cases, particles were observed distributed 2 mm along the injection tract. The maximum radial distance that NPs distributed was similar (Free NPs: 559±9 μm; NSC-coupled NPs: 509±12 μm), corresponding to a maximum volume of distribution (Vd) (Free NPs: 1.96±0.06 μl; NSC-coupled NPs: 1.63±0.08 μl) no larger than the 2 μl initial injection volume (Vi). If the NPs could diffuse freely, the Vd should be 5 fold larger than Vi given that the fraction of extracellular space in the brain is approximately 20% (Levin et al. 1970). Instead, most of the NP density for both free-NPs and NSC-coupled NPs was contained to a volume less than Vi, with most NPs distributed no more than 101-110 μm from the injection site. Similar results have been observed when injecting 100-200 nm polystyrene NPs into the brain (Chen et al. 2005).

On Day 4, no measurable NP diffusion or NSC mobility was observed, but the volume of NPs present within brains that had received free-NPs had decreased to 7±3% (FIG. 28L). This magnitude of free-NP clearance is within range of the relatively rapid clearance of hydrophilic lipid nanocapsules (half life of 7-10 hours; 94% cleared by day 3) previously observed (Allard et al. 2008; MacKay et al. 2005). While significantly longer retention times have been achieved (1% eliminated by 12 hours; Perlstein et al. 2008) by altering NP surface properties, the long residency time is usually attributed to NP endocytosis by host brain cells (Allard et al. 2009). A striking improvement in NP retention was observed in brains that had received NSC-coupled NPs (FIG. 28K). The % of NPs present remained near the 40±6% level observed on Day 1 (FIG. 28L). While these results cannot rule out the possibility that the NPs were endocytosed by the NSCs (Gennet et al. 2009) rather than remaining surface-bound; there is reason to believe that endocytosis happens minimally, as cells typically exhibit intrinsically low uptake of unmodified polystyrene NPs (Holzapfel et al. 2005) particularly if larger than 50-200 nm (Lorenz et al. 2006; Rejman et al. 2004), negatively charged (Verma & Stellacci 2010), and anchored to cell-surface proteins (Stephan & Irvine 2011). Regardless, if future studies find that NP endocytosis occurs in vivo, the kinetics of coupling and therapeutic NP delivery should be considered to ensure maximum NSC tropism takes place before NP internalization occurs.

NSCs Target NPs to Tumors In Vivo.

Figures 34A, 34B, 34C, 34D:
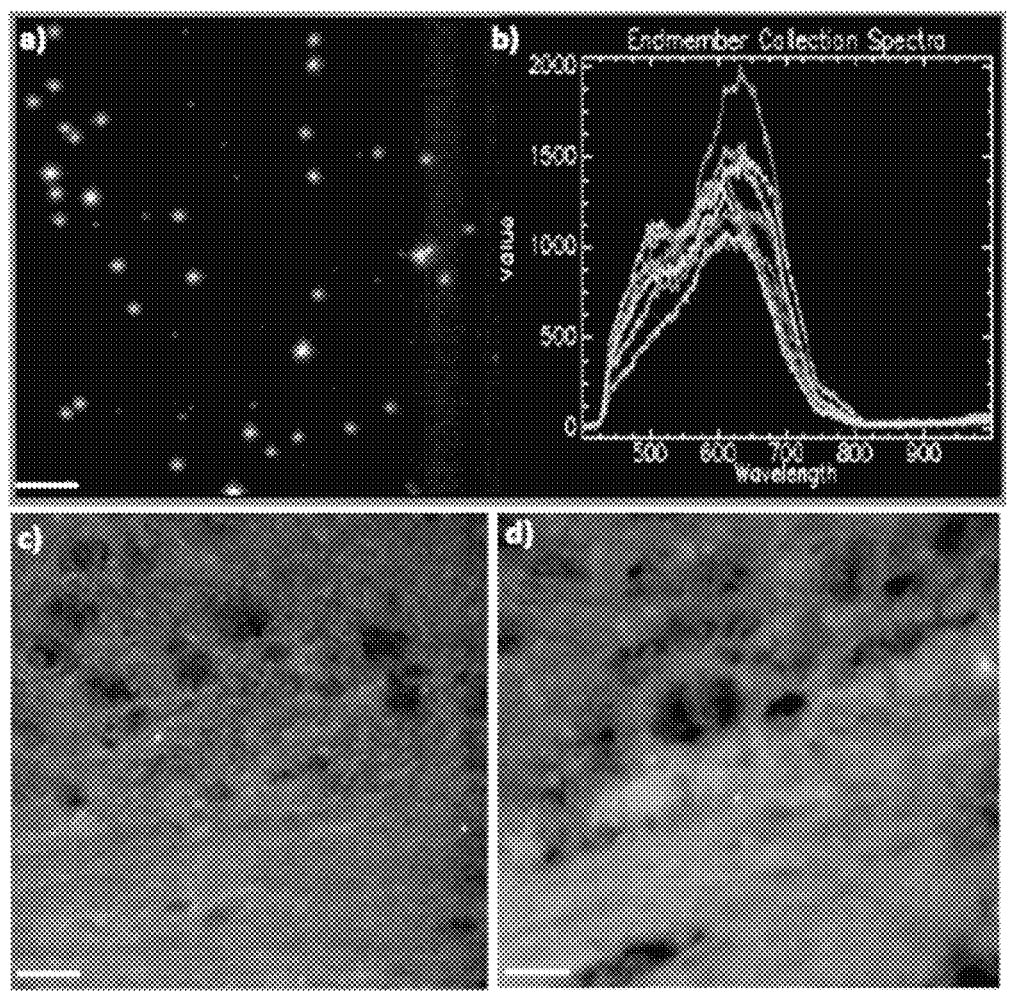
FIG. 34 illustrates the identification of a polystyrene nanoparticle within brain slices using dark—field hyperspectral imaging according to one embodiment. A reference sample of polystyrene nanoparticles (A) was scanned used to generate a spectral signature library (B) with the hyperspectral imaging system. Brain tissue slices that had received no nanoparticle injections were scanned and mapped to confirm the absence of positive signals using this spectral library (C). Brain tissue slices that had received nanoparticle injections were then scanned, and positive signals were pseudo-colored red to aid visualization (D). Scale bar=10 µm.

To determine if NSCs can distribute NPs selectively to tumor foci, NP distribution was evaluated in mice with established U251 tumors expressing firefly luciferase (ffluc) in the left hemisphere which grew ~0.2-0.5 mm in diameter by Day 7. Tumor-bearing mice received injections of either free-NPs or NSC-coupled NPs under three different injection paradigms with decreasing proximity to the intracranial tumor. NPs were injected either immediately adjacent to the tumor (<200 um away), into the contralateral hemisphere (>1 mm away), or into the tail vein. NP distribution was assessed 4 days post-NP injection; a time point within the 2-10 day range when HB1.F3 NSC presence within tumors peaks (Kim et al. 2010). Because polystyrene is difficult to identify once brought into biological systems (Mailander & Landfester 2009), NP distribution was assessed using 2 complimentary microscopic approaches. Fluorescence visualization of nile-red containing NPs was utilized as well as darkfield microscopy with spectral mapping. While polystyrene nanoparticles have been visualized using darkfield microscopy previously (Rebner et al. 2010), this technique has not yet been successfully applied to identify polystyrene particles within brain tissue slices, given the high degree of spectral overlap that exists between polystyrene and tissue. As described in FIG. 34, a polystyrene-specific spectral library was generated that was used to confirm NP presence at tumor foci. Due to the high degree of overlap, however, this technique likely underestimates the quantity of NPs present.

Paradigm #1: Ispilateral NP Injection.

The first injection paradigm involved free-NP or NSC-coupled NP injections immediately adjacent to established intracranial tumors, within the NP distribution range observed in the absence of a tumor to determine if tumor presence would alter NP retention or distribution patterns (FIG. 29A-29D). Results show that tumor presence had no significant effect on Day 4 NP retention, with 9±4% of free-NPs and 32±8% of NSC-conjugated NPs retained. In contrast, tumor presence did alter observed NP distribution patterns (FIG. 29E-29F). While the majority of free-NPs were still localized to the injection site, there was a slight asymmetric distribution favoring the direction of the tumor with 4±0.5% of injected NPs passively accumulating within the tumor region (FIG. 29J). In contrast, the majority of NSC-conjugated NPs (21±7% of injected NPs, ~66% of NPs retained in the brain) did not remain at the injection site but rather were redistributed to the tumor (FIG. 29I,29K). Aside from the injection site, no NPs were observed in non-tumor regions. Spectrally mapped dark field images confirm the presence of NPs at both the injection site and the tumor site (FIG. 29G-29H). To better visualize NP distribution throughout a representative brain, reconstruction software was utilized to generate a 3D projection of the injection and tumor site (FIG. 29I).

Paradigm #2: Contralateral NP Injection.

Figures 35A, 35B, 35C, 35D:
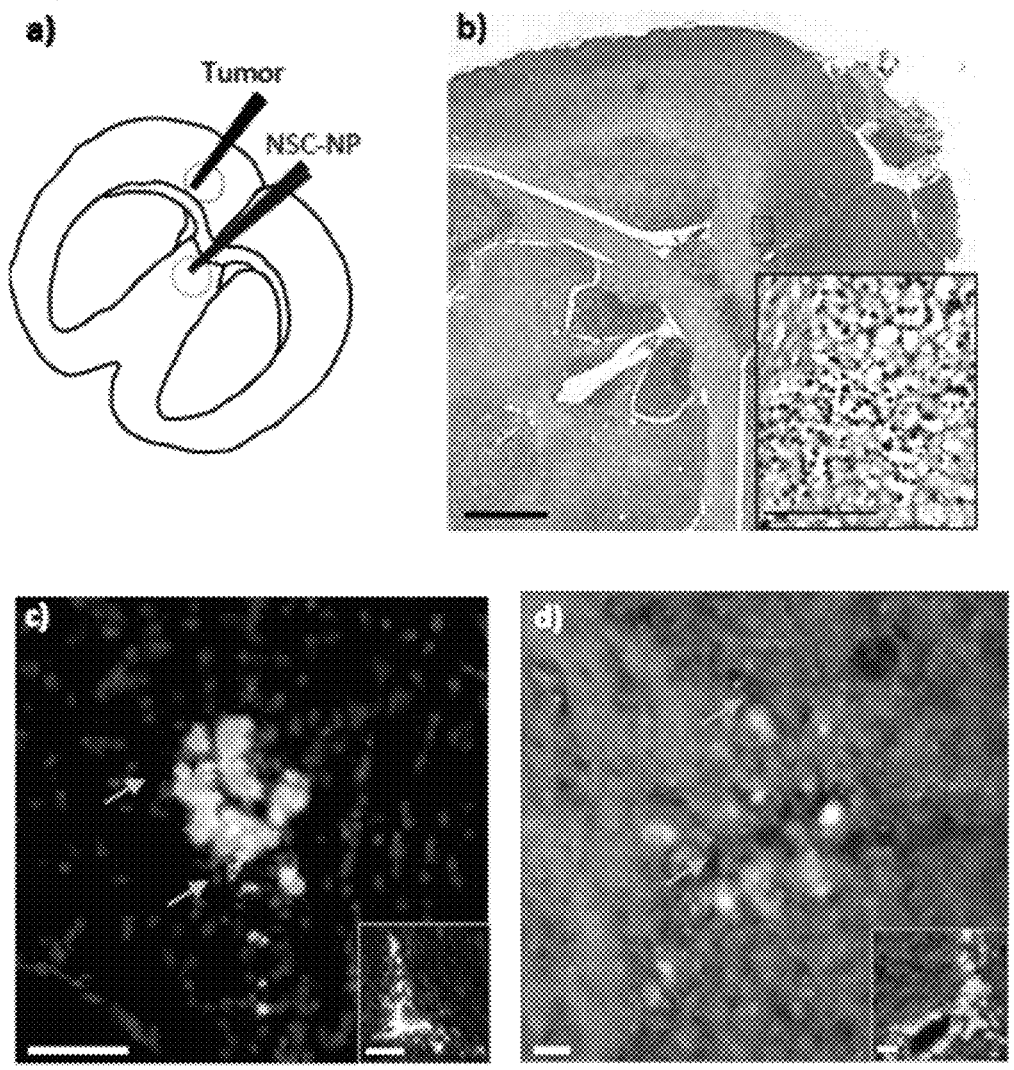
FIG. 35 shows a comparison of free—NP and NSC—coupled NP distribution when separated by a white mater track according to one embodiment. White matter tracks like the corpus collosum are known to be more conducive to NP transport (CED of adenovirus into Rat Brain) than gray matter, and may provide a pathway of least resistance between the NP injection site and the tumor. To further ensure that NSCs could distribute NPs to tumors located in grey matter when no white matter track bridged the two sites, NSCs were injected below the corpus collosum and challenged to distribute NPs above this white matter tract. A) Schematic depicting injection paradigm. b) Four days after NP injection, brains were sectioned and every 5th section throughout the entire injection and tumor site was imaged using fluorescence microscopy. The slice that contained the greatest surface area of red particles was identified and adjacent sections were used for hematoxylin and eosin staining (B) (scale bar=500 uM); as well as immunohistochemistry for anti-ffluc (inset in b) (scale bar=100 µm) to confirm the presence of tumor cells. C) Representative 20× fluorescent red-blue merged image is shown (scale bar=100 μm). Red fluorescence from NP remaining at injection site is shown in inset (scale bar=100 μm). D) The presence of polystyrene NPs was further confirmed by imaging on a darkfield microscope equipped with a 60× objective. Polystyrene NPs were identified based off their unique spectral profile, then pseudo-colored red to ease visualization (scale bar=10 μm). Injection site is shown in inset (scale bar=20 μm).
Figure 37A:
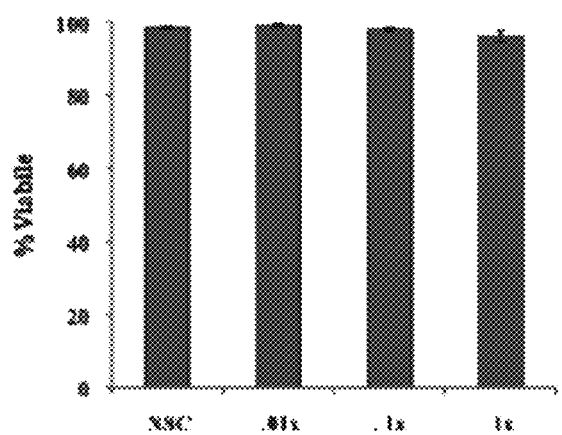
FIG. 37 illustrates the impact of MUTAB-AuNR uptake on NSC viability according to one embodiment. The viability of NSCs incubated for 16 h with [0.01×], [0.1×], [1×], or [5×] MUTAB-AuNRs was evaluated by A) Guava EasyCyte technology, B) PicoGreen DNA Quantification, and C)-F) LIVE/DEAD staining imaged via fluorescence microscopy using a 10× objective.
Figure 37B:
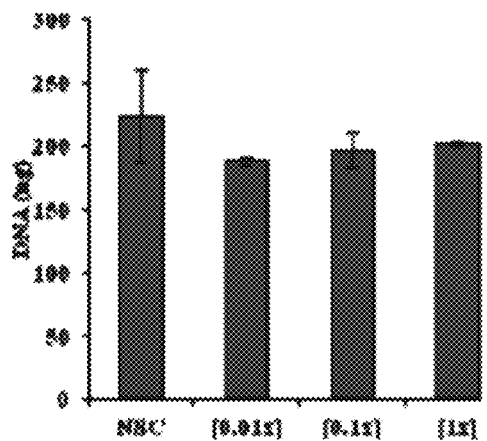
Figure 37C:
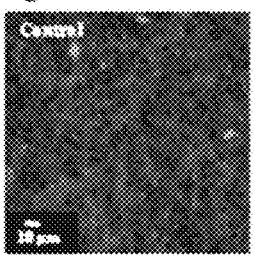
Figure 37D:
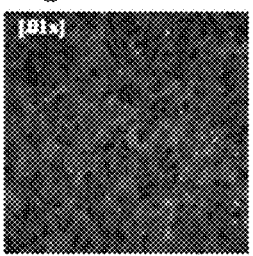
Figure 37E:
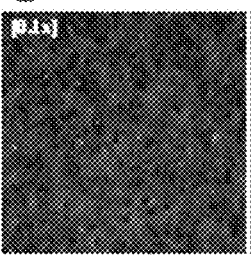
Figure 37F:
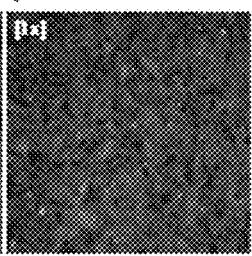

The second injection paradigm involved free-NP or NSC-coupled NP injections in the contralateral hemisphere (FIG. 30A-30D). This distance to the tumor was >1 mm and would be outside the possible distribution range for large polystyrene NPs, but very feasible for NSCs given previous studies demonstrating that a percentage of injected NSCs (typically 1-10%) can migrate along the corpus collosum distances of 3-7 mm specifically towards tumors in the contralateral hemisphere (Jackson et al. 2010; Kim et al. 2010; Tang et al. 2003; Flexman et al. 2011). Injection of free-NPs resulted in NP distribution around the injection site with no measurable NPs observed at the contralateral tumor site using either fluorescence (FIG. 30E, 30I) or dark-field microscopic techniques (FIG. 30G). In contrast, when NPs were conjugated to NSCs, 3±1.5% of the injected NPs (~7% of those present in the brain) are re-distributed selectively to the tumor site in the contralateral hemisphere (FIG. 30F, 30I). Spectrally mapped dark field images confirm the presence of NPs at the tumor site (FIG. 30H). 3D reconstruction software was again used to better visualize NP distribution throughout the entire injection and tumor site in a representative brain (FIG. 30J). Further experiments confirmed that NSCs could selectively distribute NPs to tumor foci even when the injection and tumor sites were impeded, rather than bridged by a prominent white matter tract (FIG. 35).

Paradigm #3: Intravenous NP Injection.

The final injection paradigm involved free-NP or NSC-coupled NP injections into the tail vein (FIG. 31A-31D). While the intravenous route of administration would be less invasive for NP delivery to glioma, no report of particles greater than 200 nm into the brain exists (Chen et al. 2005) due to the presence of the tumor brain barrier. Numerous studies have confirmed, however, that intravenously injected NSCs can access intracranial tumors, albeit at low (~0.5-1%) efficiency (Jackson et al. 2010; Tang et al. 2003). The low efficiency is unsurprising given that delivery of cells to the brain depends on the presence of endothelial adhesion molecules, the disruption of tight junctions, and penetration across the basal lamina surrounding the vessels (Karp & Teo 2009). As expected, no NPs were detected at the tumor site using either fluorescence (FIG. 31E, 31I) or dark-field microscopy (FIG. 31G) following intravenous injection of free-NPs. In contrast, when NPs were conjugated to NSCs, 0.9±0.2% of the injected NPs were observed at the intracranial tumor site but nowhere else in the brain (FIG. 31F, 31I). Spectrally mapped dark field images confirmed the presence of NPs at the tumor site (FIG. 31H). 3D reconstruction software was again used to better visualize NP distribution throughout the entire tumor site in a representative brain (FIG. 31J). While the efficiency needs to be optimized, this is the first study to demonstrate that intravenously injected tumor tropic NSCs can target large (~800 nm) NPs to an intracranial tumor. Note that the majority of NPs were still subject to clearance by the liver and spleen (data not shown) as would be expected for intravenously injected NPs in this size range (Decuzzi et al. 2010).

In the studies described above, it was demonstrated that NP-conjugated NSCs retain viability and tumor tropic properties. While the biotin-streptavidin NP-NSC coupling scheme was sufficient for this proof-of-concept study, it may not be appropriate for clinical use given oxidative risks (Srinivas & Colburn 1984) and the immuogenicity of streptavidin (Meyer et al. 2001). Future studies will investigate using endogenous thiols Stephan et al. 2010), or receptor-antibody combinations (Li et al. 2011). Consistent with results achieved using MSCs (Li et al. 2011), intracranial NP retention was improved when surface-conjugated to NSCs. Further, it was demonstrated that tumor-tropic NSCs can deliver NPs to intracranial tumor foci when injected at three distant locations, though the tumor-tropic efficiency decreases at increasing distances from the tumor. These results suggest that tumor tropic cells can carry much larger NP cargo than has been previously reported, which may facilitate the delivery of relevant drug doses and will allow for easier particle modifications and a better environment for preventing siRNA degradation (Eseonu 2011). Together, these results raise the possibility of utilizing tumor-tropic cells to non-invasively deliver large NPs loaded with small molecule and/or siRNA-mediated therapies to intracranial tumors, as well as tumors located in the periphery. Combining the tropism that NSCs exhibit towards sites of pathology with the broad array of controlled-release NP platforms may enable unprecedented control over the spatiotemporal release of therapeutics.

Example 3: Generation of Drug Loaded pH-Responsive Nanoparticles for Glioma Treatment Temozolomide (TMZ) is a DNA alkylating agent that is regarded as the first-line chemotherapy for glioblastoma. In current use, TMZ is orally administered and has difficultly crossing the BBB, diffuses poorly into the interior of gliomas, has a short plasma half-life (1.8 hours), and causes frequent dose reduction due to its hematologic, neurologic, or other toxicities (Zhang et al. 2010). In contrast, when TMZ is delivered from hydrolytically degradable particles implanted directly into the tumor cavity, survival times doubled compared to oral administration (Zhang et al. 2010). The hydrolytically degradable particle used to release TMZ in this previous study are unsuitable for NSC-mediated distribution given their first-order drug release profile which would kill the NSCs prior to their migration through the tumor. However, the therapeutic efficacy of TMZ may be improved by using nanoparticles. For example, pH-responsive nanoparticles that can be safely conjugated to NSCs at pH=7.4, but will dissolve and release TMZ upon entering the weakly acidic (pH=5.7-7.8 (Vaupel 2004)) tumor environment may be used (Kim et al. 2006a). The tumor environment is acidic due to what is termed "Warburg's effect", where rapidly dividing cells have high levels of lactate production (Christofk et al. 2008). This acidic tumor pH may be exploited to ensure NSC-nanoparticle conjugates are able migrate to the tumor prior to TMZ release.

Figure 6:
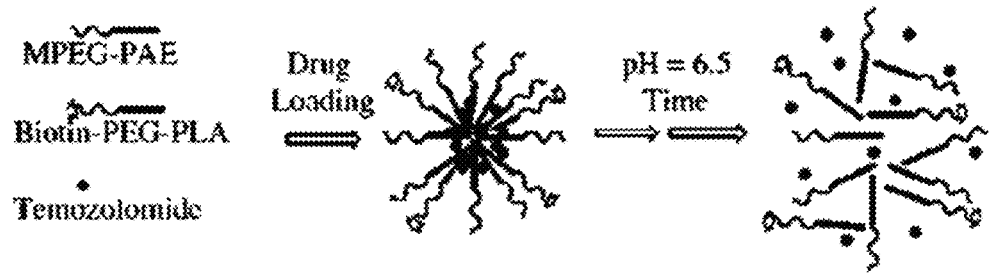
FIG. 6 illustrates fabrication of pH-responsive nanoparticles according to some embodiments. Particles may be prepared using both pH-labile and biotinylated polymers. Temozolomide (TMZ) is entrapped within the particles, coupled to NSCs that will transport them to the weakly acidic tumor environment. Drug release will ensue at the tumor.
Figure 7A:
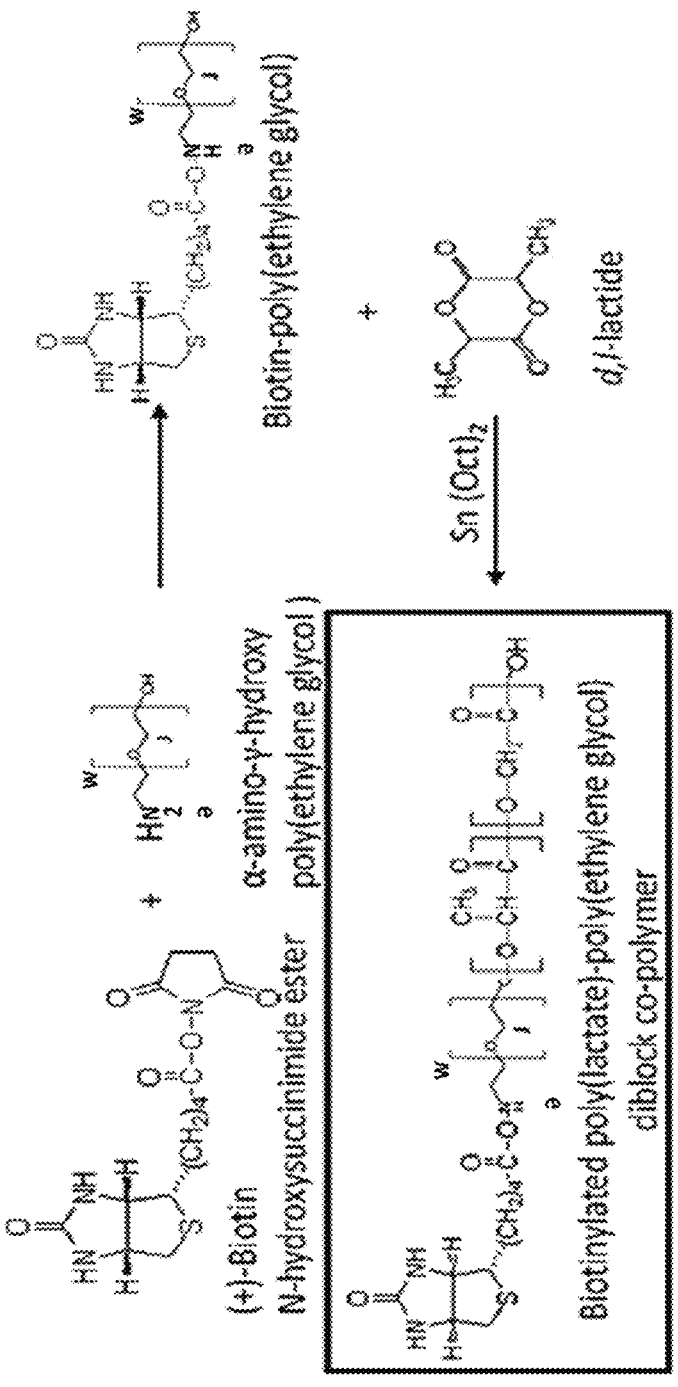
FIG. 7 illustrates a synthesis scheme for pH-labile and biotinylated polymers that includes synthesis of PEG-PLA-Biotin (FIG. 7A) and mPEG-BAE (FIG. 7B) according to one embodiment.
Figure 7B:
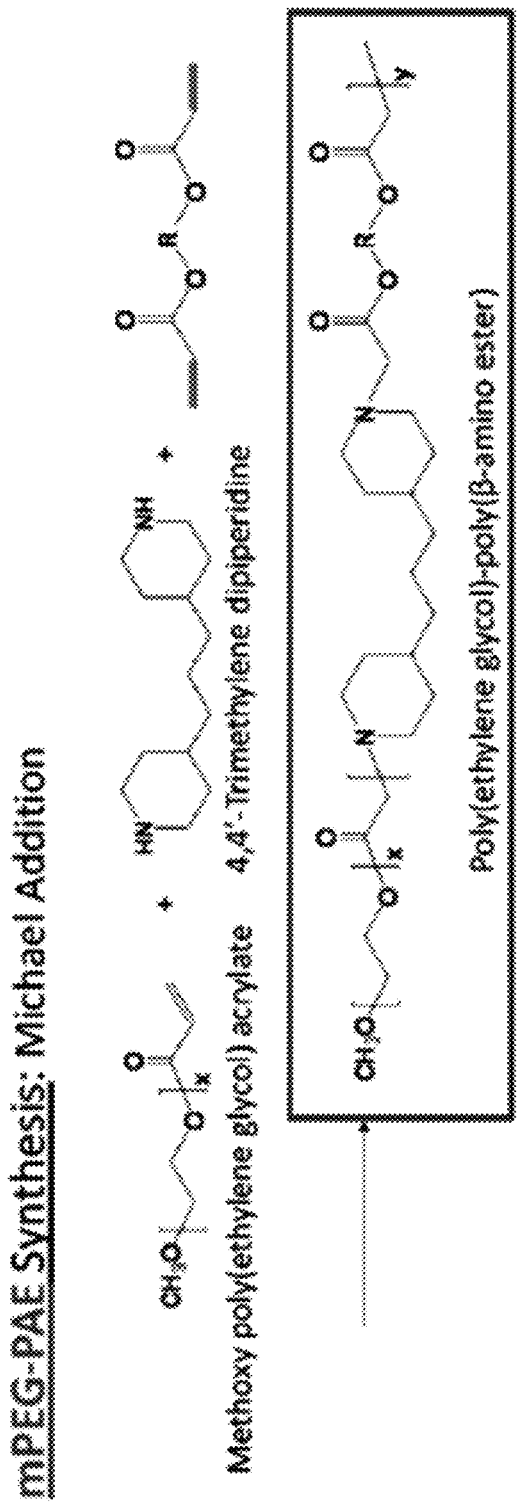
Figure 8:
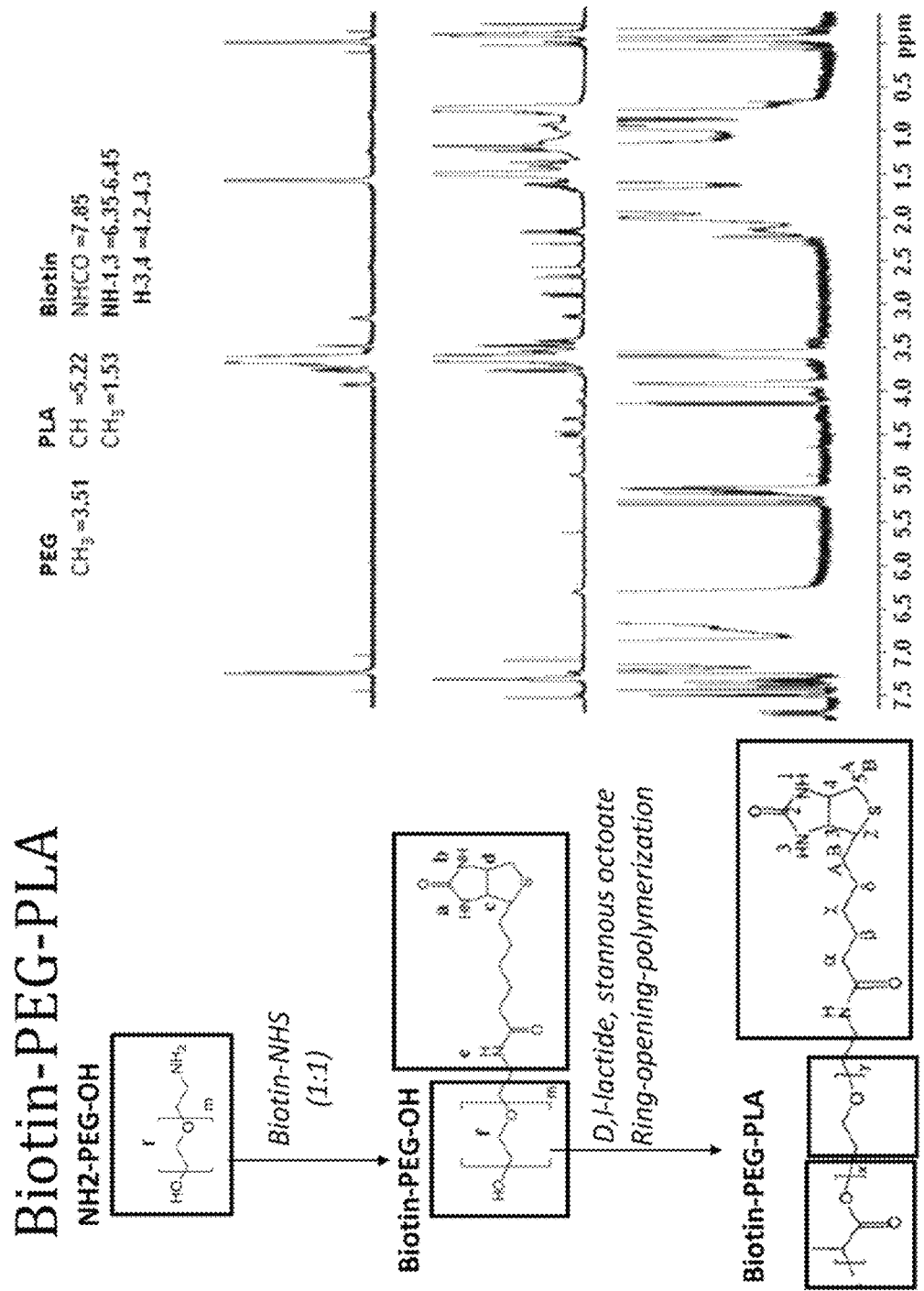
FIG. 8 shows $H^1$NMR results demonstrating successful synthesis of Biotin-PEG-PLA.
Figure 9:
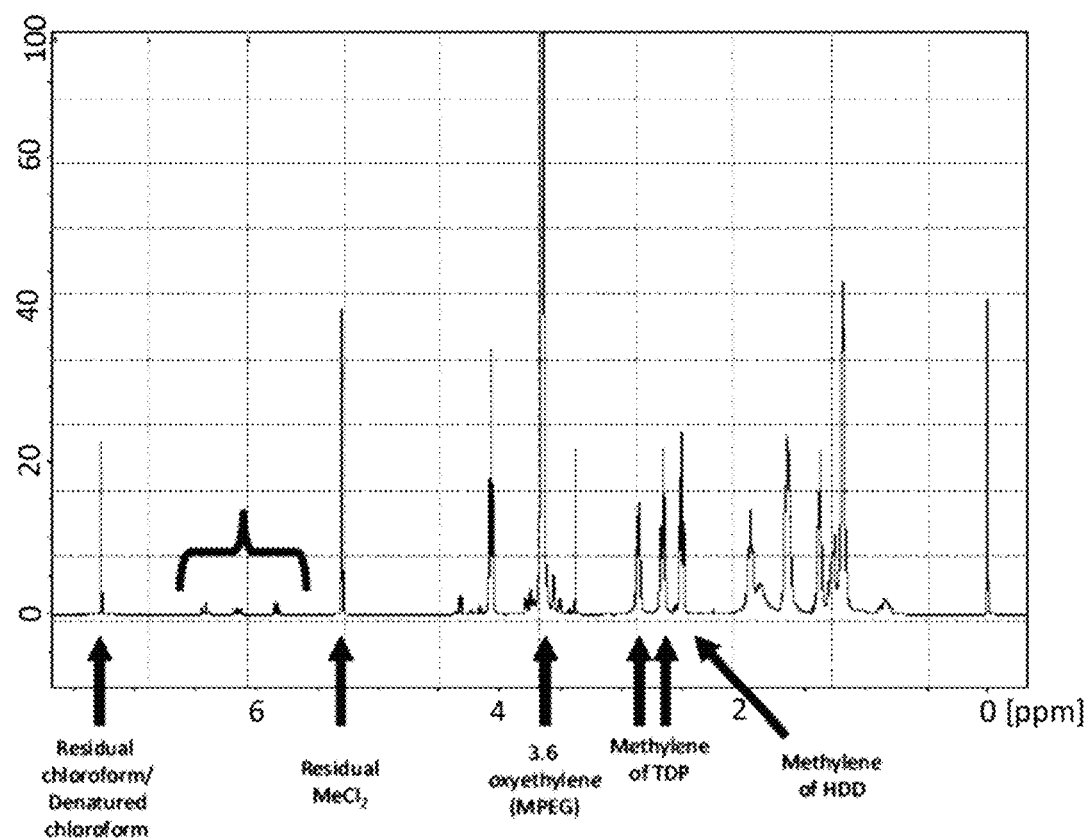
FIG. 9 shows $H^1$NMR results demonstrating successful synthesis of MPEG-BAE.
Figure 10:
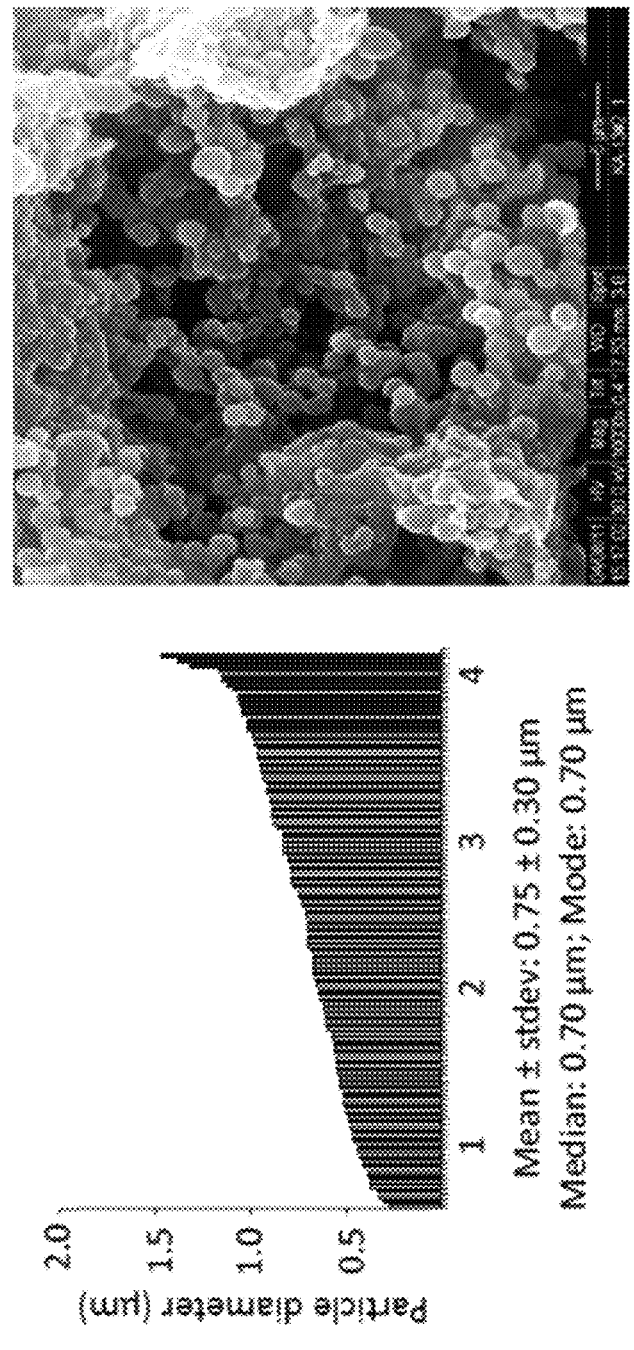
FIG. 10 shows the size distribution and image of synthesized nanoparticles as determined by SEM, according to one embodiment.
Figure 12:
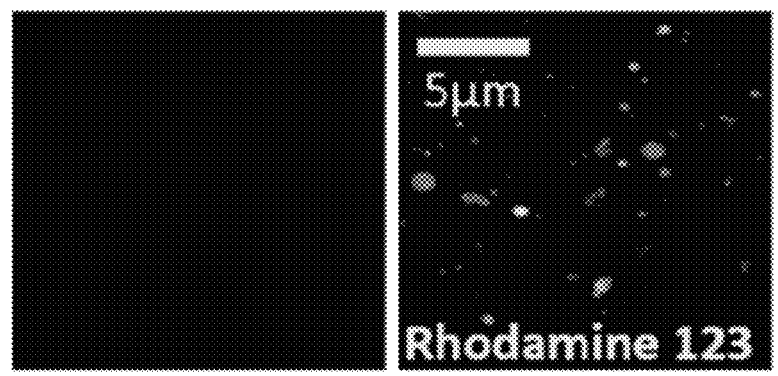
FIG. 12 shows representative images of unloaded particles and a molecule similarly sized to chemotherapeutics, rhodmaine123 (A) or Feraheme® (Iron) loaded particles (B) stained with Prussian Blue according to one embodiment. Respective loading efficiencies are listed.
Figure 12:
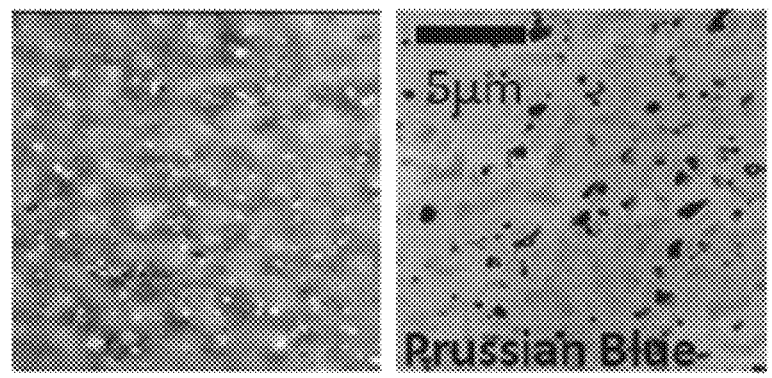
Figure 14:
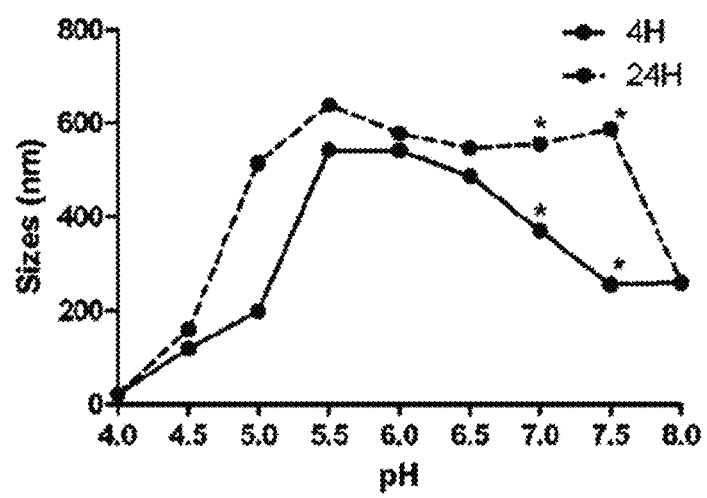
FIG. 14 shows dynamic light scattering evidence of pH-responsive articles that swell when pH decreases from pH=7.5 to pH=6.0 then undergo dissolution in more acidic environments, according to one embodiment.
Figure 15:
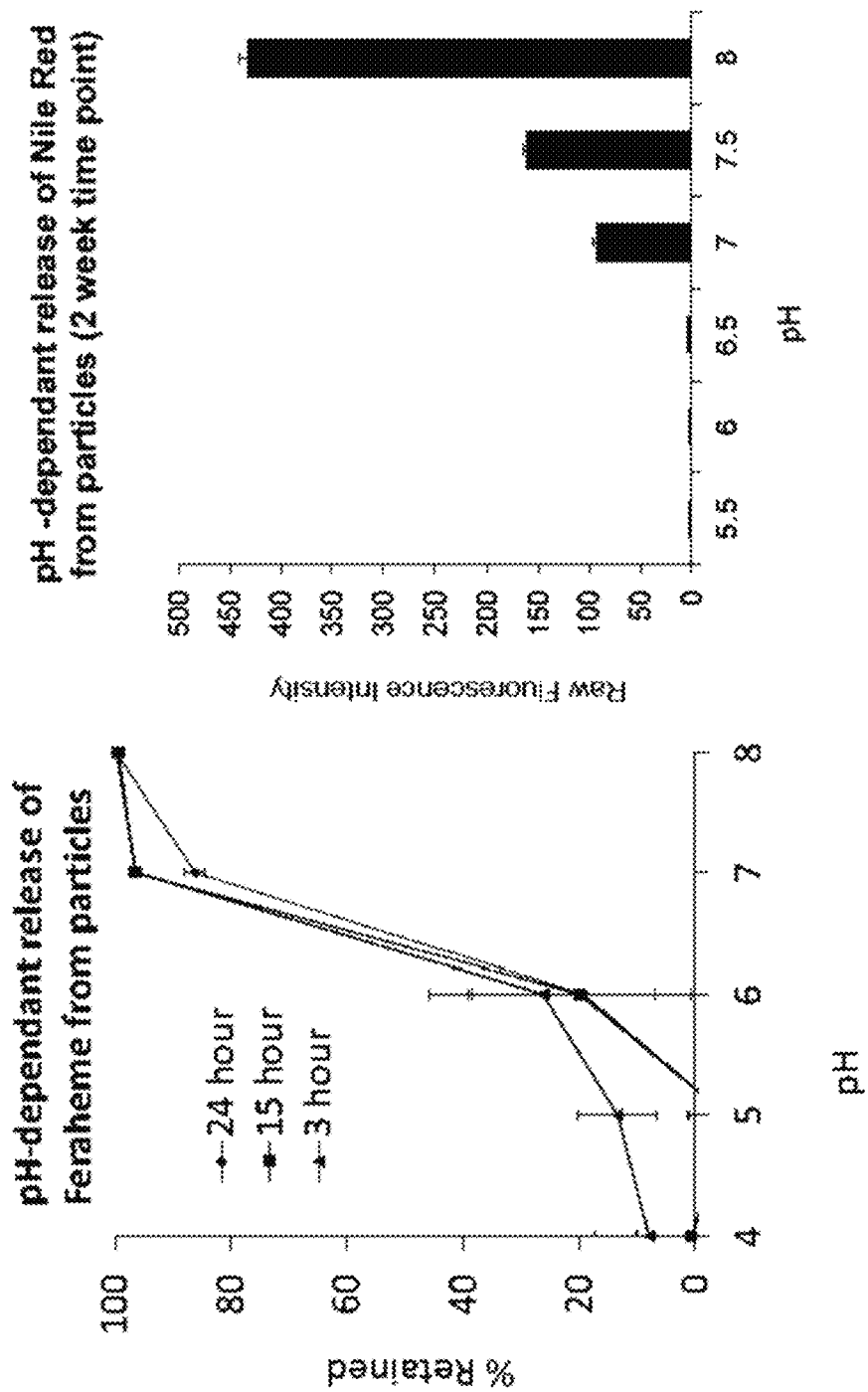
FIG. 15 shows pH-dependant release of entrapped Feraheme® (left panel) and the sample hydrophobic small molecule Nile Red (right panel), according to one embodiment.

To fabricate TMZ loaded, pH-responsive particles (FIG. 6), two polymers may be synthesized, purified, and characterized as previously described: 1) biotin-PEG-poly(lactide) (biotin-PEG-PLA) (FIGS. 7A and 8) (Krishnamachari et al. 2008), and 2) methyl ether PEG conjugated to a pH-labile linker poly($\beta$-amino ester) (MPEG-PAE) (Kim et al. 2006a) (FIGS. 7B and 9). This linker has a pKa of 6.5 and undergoes a conformational change in weak acid that results in nanoparticle dissolution (see FIGS. 14-15). These two polymers may be mixed in methylene chloride in a ratio of 9:1 pH-labile:biotinylated polymer prior to TMZ encapsulation using a standard water-oil-water double emulsion protocol (Kim et al. 2006a; Christofk et al. 2008) (FIG. 12). Hardened particles will be collected via centrifugation and washed prior to lyophilization for long-term storage. Nanoparticle size may be determined via scanning electron microscopy (Soderquist et al. 2010) (FIG. 10), and drug loading and release will be characterize via UV spectroscopy ($\lambda_{max}$ 327 nm) as previously described (Kim et al. 2006a) (FIG. 12). The sensitivity limit of TMZ using this absorbance technique has been determined to be from 0.6 ng/ml to and is linear over several orders of magnitude (data not shown). The IC50 of encapsulated TMZ may be determined with reference to free TMZ.

The size of the particles are between 300-500 nm as assessed by SEM, however (FIG. 10,14), the size range may be optimized by adjusting solvent:polymer ratios, sonication power, and stir rates if desired. It has been reported that pH-responsive nanoparticles placed in the acidic buffer condition may require a prolonged reaction time (a few hours) to present a pH-responsiveness and begin nanoparticle dissolution (Kim et al. 2006a). The use of a prolonged reaction time for the NSC-mediated distribution paradigm should not present a problem because the NSCs should retain the nanoparticles within the tumor environment. Other pH-responsive linkers may be used to prepare the particles (Gao et al. 2010) utilizing the emulsification/solvent evaporation preparation approach or by using the photopolymerized preparation approach described in Example 2 so that the tight mesh size also assists in entrapping the small molecule drugs prior to their arrival in the tumor environment. Alternatively, TMZ may be directly conjugated to a PEG-PLA polymers via a pH-labile linker eliminating the possibility of drug leakage (Aryal et al. 2010).

Upon particle dissolution, the drug release profile is expected to be $1^{st}$ order, where the majority of the payload is released in the first 24 hours (Kim et al. 2006a). This release profile has been successful at reducing tumor burden (Zhang et al 2010). Alternatively, to generate steady state drug concentrations, zero order or Higuchi release kinetics may be engineered using nanoparticle coatings or by adjusting the ratio of hydrolytically degradable to pH-labile macromer in the initial nanoparticle preparation. Initial doses of 4 mg TMZ/kg animal weight should be effective based on previous pre-clinical results (Zhang et al 2010). However, the TMZ dosage may be adjusted based on maximal TMZ loading within nanoparticles, any loss of activity. Cell number will be adjusted in order to achieve desired doses. (see below for in vivo studies).

Example 4: Generation of Diagnostic Loaded Non-Degradable Nanoparticles for Imaging Invasive Glioma To overcome challenges associated with endocytosis protocols and improve MRI detection sensitivity, SPIONs (Feraheme®) will be encapsulated into larger, biotinylated, nondegradable poly(ethylene) (PEG) and/or poly(lactic-co-glycolic acid) (PGLA) nanoparticles that will be conjugated to the surface of NSCs. Labeling NSCs with multiple SPION-loaded PEG nanoparticles should significantly increase MRI signal intensities without damaging or altering NSC fates.

Methods:

To fabricate non-degradable particles of uniform size distribution and efficient SPION loading, a particle preparation scheme will be employed similar to that previously described (Glangchai et al. 2008). An anti-stick, silicon template with molds sized 50×100 nm (Eulitha) will be filled with a photopolymerizable mixture containing photoinitiator (PI) (Irgacure 2959), Feraheme® SPIONs, a hydrogel-forming polymer, and a biotinylated polymer used to conjugate particles to NSCs. Upon exposure to low-intensity ultraviolet (UV) light, free-radical polymerization will ensue and permanently entrap the SPIONs within the biotinylated hydrogel mesh.

An initial SPION concentration of at least 40 mg/ml may be used based on calculations that if NSCs are labeled with 5 SPION-loaded nanoparticles, the MRI signal intensity should increase such that $5 \times 10^3$ cells are detectable, thus enabling MRI to approach the sensitivity levels of other techniques. SPION concentration may be adjusted based on sensitivity of MRI results.

Both the gel-forming polymer and the biotinylated polymer may be synthesized using established techniques. The gel-forming polymer (PEG-dimethacrylate, PEG-DMA) may contain a PEG backbone that has been endcapped with photoreactive methacrylate (MA) groups, purified, and characterized via $H^1 NMR$ as previously described (Sawhney et al. 1993). The biotinylated polymer (biotin-PEG-MA) will also contain a PEG backbone but may be functionalized on one end with a biotin moiety and on the other end with a MA group as previously described (Krishnamachari et al. 2008; Aboody et al. 2000; Glangchai et al. 2008; Sawhney et al. 1993; Clapper et al. 2008). The MA group will covalently tether the polymer within the hydrogel network while the biotin functionality will remain available for NSC coupling.

The PEG-DMA may be comprised of 4600 g/mol PEG and hydrogels may initially contain PI and macromer concentrations of 0.05% and 40% (w/w), respectively. These concentrations should result in a swollen-state hydrogel mesh size of 40 Å (Bryant & Anseth 2002) which ensures efficient, permanent SPION entrapment. SPION entrapment will be verified using a ferazine-based colorimetric assay. The PEG-DMA macromer weight percentage may be adjusted to ensure the SPIONs are stably entrapped. For example, if the SPION diffuses from the 40% (w/w) hydrogel, the PEG-DMA macromer weight percentage may be increased until the SPIONs are stably entrapped.

During polymerization, the particles may be isolated from each other by ensuring that residual polymer solution on the template surface has dried prior to UV exposure. Harvesting the nanoparticles from the template is facilitated as previously described (Glangchai et al. 2008). The template may then be incubated in $diH_2O$ to allow PVA dissolution and release of SPION-loaded nanoparticles. The nanoparticles will be incubated in excess avidin, washed and collected via centrifugation prior to lyophilization for long-term storage.

Figure 11:
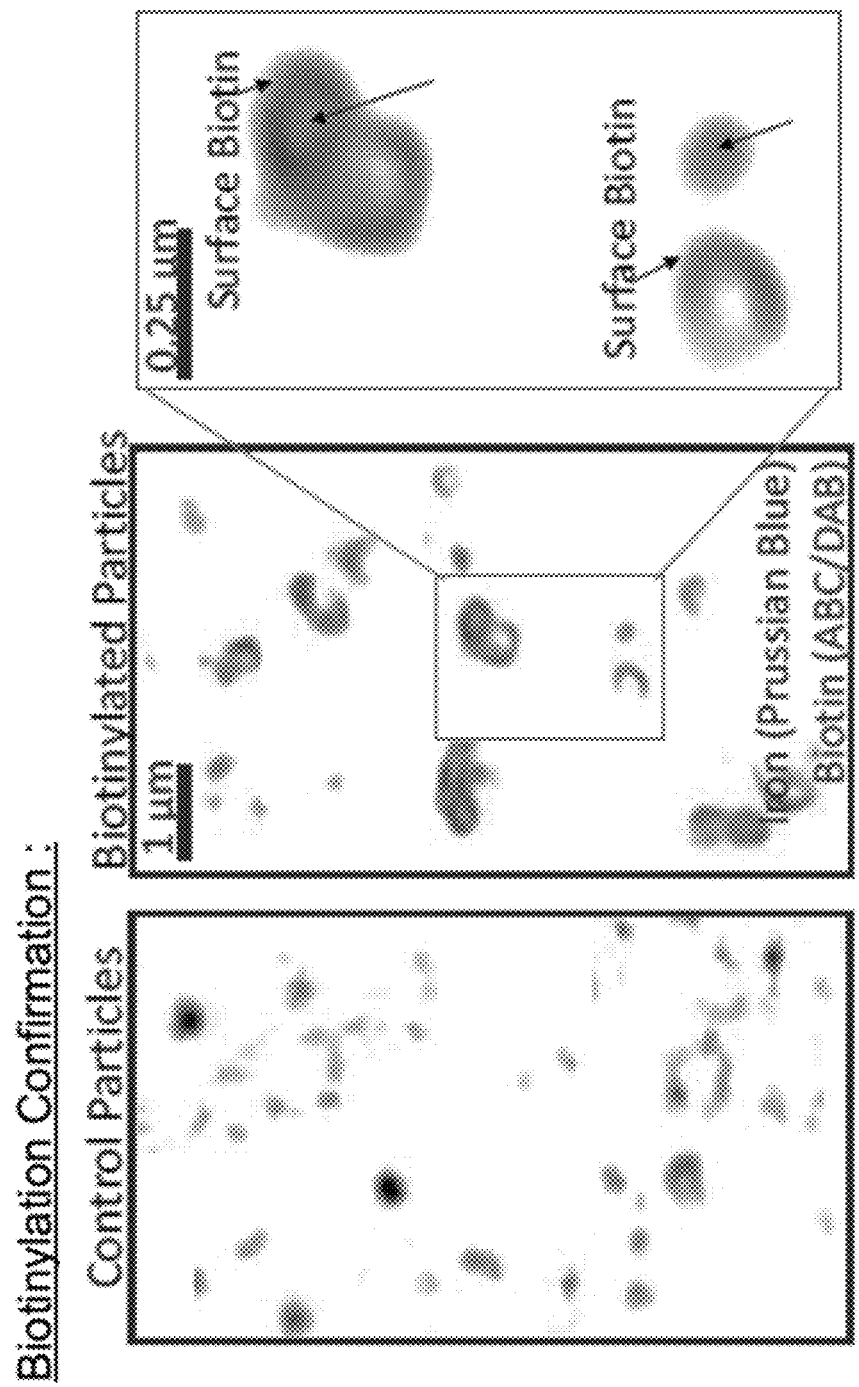
FIG. 11 demonstrates evidence of biotin moieties on the surface of iron loaded particles, according to some embodiments. The surface biotin has been amplified with an avidin, horse-radish peroxidase compound and developed using a DAB substrate to exhibit a brown color on the surface of the particles. Particles were imaged using bright field microscopy.

Nanoparticle surfaces should contain exposed biotin moieties that can be avidin-coupled to NSCs (FIG. 11). Initial biotin-PEG-MA concentrations will be 10% (w/w), though this concentration can be increased pending that the PEG hydrogel mesh size still entraps Feraheme®. Alternatively, a two-step polymerization approach may be employed in which the biotin-PEG-MA is reacted onto the surface of pre-polymerized PEG nanoparticles. This two-step approach exploits the presence of unreacted MA groups near the surface of PEG hydrogels (Peppas & Lang 2000) and is commonly employed to tether peptides onto PEG hydrogels (Moon et al. 2007).

In Vivo Assessments for Examples 2 and 3

Using the nanoparticle preparations generated in Examples 2 and 3 above, the diagnostic and therapeutic efficacy of NSCs-nanopartcle conjugates may be assessed. To allow for simultaneous diagnostic and therapeutic assessments, a combination of diagnostic and therapeutic nanoparticle preparations may be loaded onto NSCs.

In Vitro NSC-Nanoparticle Conjugate Preparation and Characterization.

Conjugate An average of 5 SPION-loaded nanoparticles and 5 TMZ-loaded nanoparticles may be conjugated to each NSC by incubating NSCs (e.g., cultured NSC cell line HB1.F3) in the presence of a mixed nanoparticle suspension. Alternatively, diagnostic NSC-conjugates and therapeutic NSC-conjugates may be separately prepared and the two populations co-injected as described below to allow for simultaneous therapeutic and diagnostic efficacy.

NSC viability and tumor tropism are confirmed at neutral pH in vitro. The MRI sensitivity limit for NSC-nanoparticle conjugates may also be established in vivo by titrating down intracranially injected cell number. A significant improvement in MRI sensitivity of tumor tropic NSCs will likely be observed and an improvement in viability and ease of NSC labeling provides an advantage in the field.

To confirm tumor toxicity in weak acid environments in vitro, the NSC-nanoparticle conjugates may be incubated with glioma cell lines. The amount of TMZ present is estimated based off TMZ and nanoparticle loading efficiencies. Glioma cells will be exposed to increasing doses of either 1) free TMZ, 2) particle entrapped TMZ, or 3)NSC-nanopartle conjugates loaded with TMZ. Cell viability is assessed after 72 hours and respective IC50 values will be determined as previously described for other drugs (Shubayev et al. 2009).

In Vivo Demonstration of Diagnostic and Therapeutic Efficacy of Tumor-Tropic NSC-Nanoparticle Conjugates.

Thirty (ten per group) 5-7 week old nude mice may receive a right frontal lobe injection of $3 \times 10^5$ human ffLuc expressing U251 glioma cells. After 1 week, the treatment group receives a tail vein injection of $1 \times 10^5$ NSC-nanoparticle conjugates. Control groups receive unmodified NSCs or unconjugated nanoparticle suspensions. NSC migration may be monitored in vivo via MRI on days 1, 4, 7, 10, and 30. On day 7, 3 mice per group are harvested to assess the ability of the NSC-generated MRI signal to accurately identify infiltrative tumor cells by comparing to histological evaluations. Tissues may also be collected to assess off-target NSC migration and/or nanoparticle deposition. Prussian blue staining is used to identify NSC-nanoparticle conjugates (Aboody et al. 2000). FIG. 6 shows an exemplar treatment regimen that may be used according to the embodiments of the disclosure, though the regimen may be adjusted or modified accordingly.

To confirm the presence of NSCs, anti-human nestin will be employed using standard immunological techniques. On day 30, 3 more mice per group are harvested to assess viable tumor volume in each treatment group after serial sectioning of brain, staining with hematoxylin and eosin, and employing 3D tumor reconstruction methods. The remaining 4 mice per group are then followed for long-term survival, with death as an endpoint.

The initial TMZ dose (4 mg/kg) may be adjusted based on the observed therapeutic effects. For example, the dose may be increased beyond levels typically given orally to determine if dose restrictions can be alleviated using NSC-nanoparticle conjugates. Alternatively, multiple tail vein injections can be attempted at 2 day intervals to increase the dose over a delayed timescale.

Example 5: Toxin Therapy Targeted to CD133$^+$ Glioma Stem Cells

Another reason that the glioma tumors might be so robust is that current therapies only target quickly dividing cells without regard to the cellular heterogenetity present within tumors. Combinatorial, ligand-specific techniques that eliminate known tumor populations as well as the purported, slowly dividing, CD133+ glioma stem cell (Ignatova et al. 2002), may be more efficacious than single-drug approaches. Combinatorial regimens that target IL-13 receptors, transferrin receptor, and CD133+ cells may also reduce off-target toxicities given the absence or low abundance of these ligands on healthy brain cells (Pfenninger et al. 2007). A combinatorial, targeted toxin cocktail may result in a more aggressive treatment and should decrease the likelihood that a population of cancer cells will be able to survive the treatment. To test this, a different tumor tropic NSC is used, a combinatorial targeted toxin regimen is empirically determined, a more relevant glioma animal model is used, and efficient delivery of the toxins should be ensured.

Isolation of Relevant Tumor-Tropic NSCs.

Primary neural stem cells may be isolated from the lateral ventricle wall of the subventricular zone in adult mice as previously described (Pfenninger et al. 2007). This source of neural stem cells was chosen because it has been shown to contain a population of $CD133^-$ adult neural stem cells (type B cells) that are capable of demonstrating tropism towards gliomas (Glass et al. 2005). The $CD133^-$ property of these cells is important for using these cells to deliver a toxic ligand that targeted $CD133^+$ cells. Briefly, tissue is dissected from 5 adult mice per experiment and the isolated tissue is dissociated into a single cell suspension using both mechanical and enzymatic means. Fluorescence-activated cell sorting (FACs) is then employed to separate the cell suspension into $CD133^+$ and $CD133^-$ fractions. The $CD133^-$ fraction may then be collected for experimentation. The collected neural stem cells are then cultured in BrdU containing media to label them for visualization once implanted back into an animal.

Empirical Combinatorial In Vitro Studies.

Primary glioma cells may be isolated as described above and the maximum effective concentration of each of the three toxic ligands applied in isolation may be determined by quantifying the ability of each to eliminate the greatest number of tumor cells in this mixed cell population in monolayer. These studies may be focused around a concentration of approximately 1 µg/ml based on the efficacy of this concentration demonstrated in previous studies (King et al. 2005). Cell death may be quantified using the Caspase-3 and ATP cell death/viability assays as described above. Next, each of the following four combinatorial cocktail combinations shown in Table 6 may be applied to the in vitro glioma cultures using the maximally effective concentration of each of the different toxic ligands.

TABLE 6

Combinatorial Treatment Regimen

| Combination | Toxic Ligands |
| --- | --- |
| 1 | CD133, IL-13 |
| 2 | IL-13, Transferrin |
| 3 | CD133, Transferrin |
| 4 | CD133, IL-13, Transferrin |

Cell death may be quantified using the Caspase-3 and ATP cell death/viability assays as described above. Further, one or more additional targeted toxins may be included in the combinatorial cocktail, such as a toxin that targets the IL-4 or TGF-α receptor (Weber et al. 2003; Sampson et al. 2003). The combinatorial cocktails described herein may eliminate most or all glioma cells, improve animal lifespan over treatments with a singular targeted toxin ligand, or a combination thereof.

Generation of a Relevant Animal Model.

The selected animal model mimics the complexity of a human glioma, in contrast to simpler glioma models that have previously been used to characterize the efficacy of glioma treatment regimens (King et al. 2005). The simple glioma models are associated with a discrepancy that exists between clinical trial results and the results of pre-clinical trials. This discrepancy may be due to several factors, including the following. First, the simple glioma models are typically generated by implanting a suspension of homogeneous tumor cells obtained from a glioma cell line (Barth 1998), whereas spontaneously occurring human gliomas are notoriously heterogeneous and contain populations of cancer cells that are able to develop resistance to various treatment approaches (Cowen et al. 2002). In addition, in many of the simple glioma models, the therapeutic drug is implanted at the same time as the tumor cells rather than allowing the tumor time to establish itself and generate microsatellites (Desanknai et al. 2003). Therefore, by using a simple glioma model, the tumors are much easier to eliminate using a single therapeutic approach.

To address this discrepancy, a more realistic glioma animal model (GFAP-Cre/p53+/− mice) that closely recapitulates the pathophysiology of gliomas in humans has been developed, wherein accumulating somatic mutations in a single cell or a small number of cells result in the formation of a glioma tumor (Marumoto et al. 2008). To generate this model, Cre-loxP controlled lentiviral vectors are injected in an adult mouse brain. These vectors are able to transduce the activated form of oncogenes to both dividing NSCs and post mitotic, terminally differentiated astrocytes in a cell type and in a region specific manner in the adult mouse brain (Marumoto et al. 2008). This new glioma mouse model may be used for the experiments described herein to mimic the complexity of human gliomas as closely as possible.

Improved Delivery of Targeted Toxin Therapy

Targeted toxins are typically delivered through a process called convection-enhanced delivery (CED), where a plurality of catheters are placed in the targeted brain area and the targeted toxins are slowly infused at a slow, continuous rate (Saito et al. 2004). This delivery method is an effective way to achieve safe, widespread distribution of the toxins, however there is poor tumor selectivity and poor access to tumor satellites distant from the primary tumor. Delivery of the targeted toxins may be improved by employing a delivery vehicle that carries the toxins directly to the tumor microsatellites. The delivery of targeted toxins to tumor microsatellites may be improved by employing a live delivery vehicle such as a neural stem cell-particle hybrids.

Generation of Avidinylated NSCs that Demonstrate Tropism Towards Gliomas.

NSCs may be biotinylated as previously described (Krishnamachari et al 2008). Briefly, NSCs are biotinylated by converting native sialic acid residues on the cell surfaces into non-native aldehydes using a mild 1 mM $NaIO_4$ solution. Sialic acid is a ubiquitous terminal cell surface monosaccharide group (Prescher et al. 2004). The cells are then be washed with PBS and the aldehyde groups are reacted with a solution of 0.5 mM biotin-hydrazide in PBS to produce biotinylated cells. The cells are again washed with PBS, then incubated with avidin 20 minutes prior to particle coupling.

Generation of Biotinylated Microparticles that Release Targeted Toxins.

One advantage of PLGA delivery systems is that the rate at which a drug is released from the microparticle can be controlled by changing the ratio of polylactide to polyglycolide in the copolymer or by varying the molecular weight of either of the components. Generally, the rate at which drug is released is increased by decreasing the molecular weight of the copolymer, or by incorporating higher ratios of glycolic acid (Cohen 1991). When injected into the body, PLGA-based materials are degraded by hydrolysis, producing lactic acid and glycolic acid. These degradation products are removed from the body via the citric acid cycle (Panyam & Labhasetwar 2003).

Synthesis of Biotinylated Microparticles with Three Different Encapsulated Toxins.

Targeted-toxin loaded, avidin-saturated, degradable microparticles may be manufactured as previously described (Krishnamachari et al 2008). Briefly, a biotinylated copolymer composed of poly(ethylene glycol) and poly(lactid acid) (PLGA copolymer) is synthesized by reacting N-hydroxysuccinimide (NHS)-biotin with the amine terminus of bifunctional α-amine-ω-hydroxy-PEG. The α-amine-ω-hydroxy-PEG is prepared by reducing commercially available α-amine-ω-carboxylic acid-PEG with a mixture of 1M tetrahydrofuran-borane. $H^1$ NMR may then be employed to confirm the attachment of biotin to the PLGA copolymer. The product may be purified via rotary evaporation and ether precipitations.

Microparticles composed of biotinylated PLGA may be prepared using a double emulsion solvent evaporation methodology. This method involves creating a first emulsion by combining an organic solution of biotinylated PLGA dissolved in dichloromethane with an aqueous solution of a given targeted toxin dissolved in $diH_2O$. Hydrolyzed polyvinyl alcohol (PVA) is added to the aqueous solution to act as an emulsifying agent. In this first emulsion, the volume of the organic phase exceeds that of the aqueous phase by 50:1. The combined solutions are sonicated for 30 seconds. The first emulsion is then added to an aqueous solution of PVA in $diH_2O$; this time the volume of the aqueous phase will exceed the organic phase by a ration of 50:1. This mixture may be stirred overnight to allow the organic phase to evaporate and the microparticles to form. The microparticles are then washed 6 times in a series of centrifugation and resuspension steps. The particle size distribution may be determined using low vacuum scanning electron microscopy, and should be around 1 μm in diameter (Krishnamachari et al 2008). Stir rates and concentration of PVA may be adjusted accordingly to achieve microparticles in the desired size range.

Determination of the Targeted Toxin-Microparticle Loading Efficiency.

The efficiency with which each toxic ligand is loaded into microparticles may be determined by dissolving 1 mg of lyophilized microparticles in methylene chloride. This solvent dissolves the microparticle and releases the entrapped toxic ligand. The toxic ligand may be extracted using 1×TE buffer, then quantified using a commercially available BCA protein quantification assay. Three different microparticle preparations may be generated for the three different targeted toxins.

Controlling Dose and Duration of Targeted Toxin Delivery In Vitro:

Because the microparticles degrade via hydrolysis of the lactide and glycolide bonds, the entrapped toxic ligands are released from the microparticles. Delivery of 40 mls of targeted toxin solution at concentration of approximately 1 μg/ml of targeted toxin may be needed to reduce tumor volumes when CED is used (Kunwar 2003; Laske et al. 1997). Thus, a delivery load of about 40 μg of targeted toxin is released into the brain within a 30 minute time span. Microparticle mediated delivery avoids the need to infuse the brain with large volumes of liquid and allows a sustained release of the targeted toxin. Delivery of the targeted toxin in this way may also reduce the dosage requirements as the toxin is presented to the glioma tumor over a longer timescale. According to the studies described herein, a high dosage of targeted toxin may be released over the course of about 2 months to ensure that the NSCs have enough time to deliver the targeted toxin-loaded particles to distant tumor microsatellites.

Figure 13:
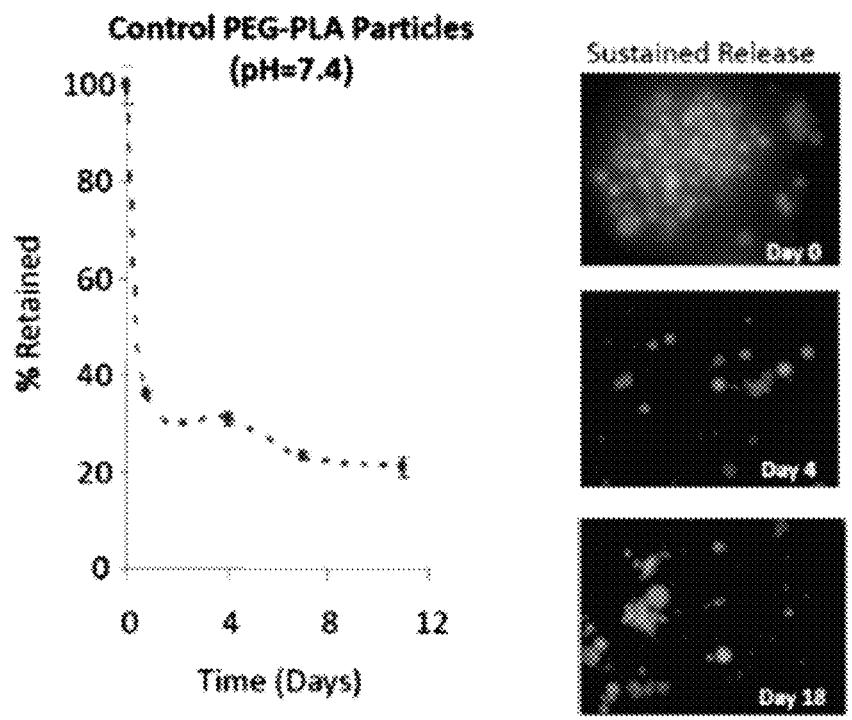
FIG. 13 shows on possible delayed release profile (first order) of rhodamine 123 from particles, according to one embodiment. Images confirm continued presence of rhodamine within the particles.

To monitor the release profile for each targeted toxin, a theoretical loading mass of 100 μg of targeted toxin per mg of microparticles may be loaded into a batch of microparticles prepared to degrade over the course of 2 months. Dextran may be co-encapsulated with the toxins to act as a co-dispersant that helps to stabilize the targeted toxins during particle manufacturing. The microparticles may be suspended in PBS for 2 months, or until the microparticles are completely degraded. The choice of PLGA copolymer governs the time-scale over which the toxic payload is released. Microparticles are initially prepared with a 50:50 copolymer of PLGA (m.w. 75000) based on the ability of this formulation to degrade over the course of 2 months. The suspension may be held in a water bath at 37° C. to mimic physiological temperature. At various time intervals, the particles may be pelleted via centrifugation. The supernatant may be removed for quantification and replaced with fresh PBS. The amount of targeted toxins released into the supernatant may be quantified using the BCA protein quantification assay. Each of the targeted toxins may have a similar release profile. An exemplar profile is shown in FIG. 13.

Toxins are Functional after Encapsulation Using In Vitro Studies.

The targeted toxins may be analyzed to determine if each is still functional after being encapsulated in microparticles, lyophilized, and then released over the course of 2 months. To assess the efficacy of micro-particle mediated delivery of targeted toxins, microparticles may be suspended within a glioma culture well contained in a membrane with a 0.45 μm mesh size. This membrane avoids microparticle uptake by astrocytes present in the glioma cell culture. The ability of released targeted toxins to eliminate ligand-specific glioma cells may be quantified using the Caspase-3 and ATP cell death/viability assays as well as immunohistochemistry. The efficacy of the targeted toxins released from the microparticles may be assessed in multiple experiments that cover the entire degradation profile of the microparticles to ensure that the targeted toxins are still effective after weeks of incubation at 37° C. Finally, all three microparticle preparations may be combined to assess the ability of the different microparticle preparations to release an effective cocktail of targeted toxins to the glioma cell cultures.

Generation of NSC-Microparticle Conjugates

Figure 5:
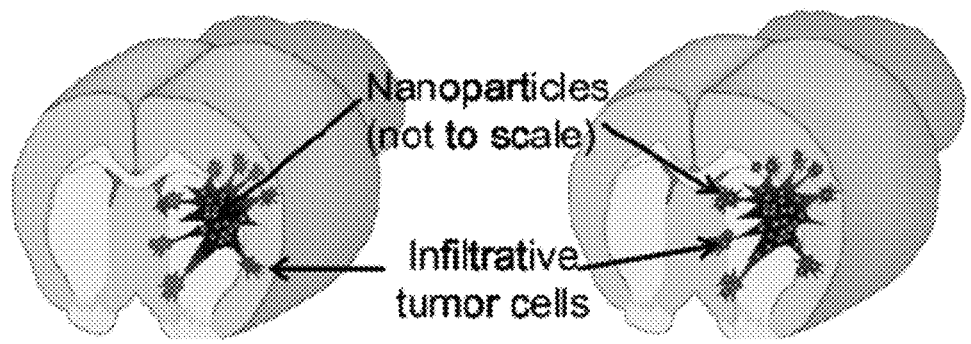
FIG. 5 is a schematic diagram illustrating the limitations of using nanoparticles as a delivery vehicle by themselves as compared to advantages of using nanoparticle-NSC conjugates or hybrids as the delivery vehicle for the treatment and diagnosis of tumors according to some embodiments. As shown in (A), nanoparticles by themselves do not efficiently or selectively distribute payloads to tumors. Thus, infiltrative tumor cells that are located near intact vasculature may escape or survive treatment. In (B), NSC-nanoparticle conjugates or hybrids selectively home to tumors where they may penetrate and distribute payloads to infiltrative tumor cells.

The preparation of cell-microparticle conjugates is schematically depicted in FIG. 5.

Microparticle Formulation Attached to NSCs Using Avidin.

Each of the three preparations of targeted-toxin loaded microparticles may be attached to NSCs as previously described (Krishnamachari et al 2008). Briefly, freshly avidinylated cells will be incubated with a 1 mg/ml solution of biotinylated, targeted-toxin loaded microparticles prepared as described above. The cells are washed with PBS to remove unbound microparticles. A separate reaction may then be performed for each of the three targeted toxin-specific microparticle preparations.

For each of the three NSC-particle conjugate preparations, NSC cell viability may be assessed immediately after cell-particle conjugate formation, 1 week after cell-particle conjugate formation, and 1 month after cell-particle conjugate formation using the Caspase-3 and ATP cell death/viability assays as well as using trypan-blue. It is important to confirm that the releasing targeted toxins do not kill the NSC delivery cells that are used for their tropism towards glioma microsatellites.

NSC-Particle Conjugates are Toxic to Glioma Cultures In Vitro.

It is also important to assess if the targeted toxins released from NSC-particle conjugates are able to release targeted toxins that are capable of eliminating glioma cells in vitro. To assess the efficacy of NSC-particle mediated delivery of targeted toxins, each of the three NSC-particle conjugate preparations may be co-cultured along with a primary glioma cell culture. The ability of released targeted toxins to eliminate ligand specific glioma cells over the long term may be quantified using the Caspase-3 and ATP cell death/viability assays described as well as immunohistochemistry. Finally, all three NSC-particle conjugate preparations may be combined to assess the ability of the different conjugate preparations to release an effective cocktail of targeted toxins to the glioma cell cultures.

NSC-Particle Conjugates are Able to Track Malignant Gliomas.

Approximately 3 months after inducing the tumor in one hemisphere (e.g., the right hemisphere) of five GFAP-Cre/p53+/− mice per experiment, the mice are anesthetized, and will receive an implant of BrdU labeled, CD133−, NSC-particle conjugates suspended in PBS. The particles will be blank, unloaded particles containing no targeted toxin. The NSC-particle conjugates will be injected stereotactically into the opposite hemisphere (e.g., left hemisphere). Fibroblasts may also be injected as a non-migratory negative control as is standard (Aboody et al. 2000). Blood pressure and rectal temperature may be monitored and heat lamps may be used to maintain body temperature at 37° C. Mice may also be treated with Cyclosporin to mediate immune response. Animals may be sacrificed on days 12 and 21. The brains are isolated, fixed in paraformaldehyde, and cryosectioned. Immunohistochemistry may be performed on brain sections. Anti-BrdU may be used to visualize transplanted NSCs, and anti-GFAP and anti-Cox-2 (Prayson 2002) expression may be used to visualize the tumor distribution.

Assessment of NSC-Microparticle Conjugate In Vivo Efficacy.

Approximately 3 months after inducing the tumor in one hemisphere (e.g., the right hemisphere) of ten GFAP-Cre/p53+/− mice per experiment, the mice may be anesthetized and may receive an implant of BrdU labeled, CD133−, NSC-particle conjugates suspended in PBS. The particles may be loaded with targeted toxins. Targeted toxins may then be administered at a concentration of no less than approximately 1 µg/ml as is typical for targeted toxins (King et al. 2005), but may be higher based on the maximally effective concentration identified during the in vitro studies. The transferrin receptor targeted toxin will be used as a positive control as this toxin is reported to be the most effective against complex malignant gliomas (King et al. 2005). Saline may be used as a negative control. Animal survival time will be quantified to determine effectiveness.

A combination of NSC-particle conjugates may be used so that all three targeted toxins are included in the treatment cocktail. The NSC-particle conjugates may be injected stereotactically directly into the tumor bed. Fibroblasts may also be injected in separate mice to be used as a non-migratory negative control as is standard (Aboody et al. 2000). Blood pressure and rectal temperature may be monitored and heat lamps may be used to maintain body temperature at 37° C. Mice may be treated with Cyclosporin to mediate immune response. Five animals may be sacrificed on day 21 to monitor tumor volume both with and without treatment. Tumor volume may be assessed using standard immunohistochemistry where anti-GFAP and anti-Cox-2 (Prayson 2002) expression may be used to visualize the tumor distribution. The other 5 animals may be left alive to assess survival time both with and without treatment.

Sustained release of targeted toxins encapsulated in microparticles is likely be more effective than a 30 minute infusion of targeted toxins via CED (The targeted toxin may be administered to the affected brain region via polyethylene catheters (e.g., PE-50) with positive pressure infusion for 30 minutes at a constant rate of 0.5 µl/minute (Vavra et al. 2004)). Also, coupling the particles to NSCs should improve the ability of the targeted toxins to be delivered to elusive tumor microsatellites. Using targeted toxins that are capable of not only eliminating a diverse array of glioma cells, but also eliminating the glioma stem cell should significantly reduce the ability of tumor cells to survive treatment. Moreover, an additional NSC-particle conjugate that is capable of releasing either an anti-inflammatory protein or a toxic ligand targeted towards immune cells may also be used to prevent an immune response against the implanted NSCs or particles, thereby reducing the possibility of an adverse immunogenic response to the therapy. Therefore, the NSC-mediated delivery of a combinatorial targeted toxin regimen such as those described herein should be more effective in shrinking tumor volume and improving survival time relative to the standard treatment regimen.

Example 6: Gold Nanoparticle-Loaded Neural Stem Cells for Photothermal Ablation of Cancer As described above, gold nanoparticles (AuNPs) have recently been identified as a prospective non-cytotoxic cancer therapy due to their ability to enhance light scattering and absorption that can be used for photothermal ablation of tumors. Photothermal therapy uses AuNPs to convert near-infrared light into thermal energy intense enough to destroy surrounding tumor cells. While this therapy holds much promise, AuNPs freely injected into the bloodstream have limited penetration into poorly vascularized hypoxic tumor regions, are unable to cross the blood-brain barrier, and are not efficiently retained at the tumor site (often <10% of the injected dose is found at the tumor)—commonly accumulating in off-target sites such as the liver and spleen. Neural stem cells (NSCs), given their inherent tumor-tropic properties, can potentially overcome these obstacles by selectively delivering AuNRs to invasive and metastatic tumor foci, even in the brain.

To develop therapeutics that enable NSCs to destroy tumor cells and tumors, NSCs may be loaded with NPs. Early work in the nascent field of stem cell/nanoparticle conjugates has focused on decorating the surface of the stem cells with NPs carrying a chemotherapeutic drug (Cheng et al. 2010; Roger et al. 2010; Li et al. 2011). In this approach, however, care must be taken to ensure that surface functionalization does not disrupt the stem cells' natural properties. An alternative approach involves loading NPs inside the stem cells. Magnetic resonance tracking of NSCs has been previously accomplished by loading the NSCs with iron oxide nanoparticles, demonstrating that NSCs can transport internalized nanoparticles to tumor foci in vivo (Gutova et al. 2012). To use this approach therapeutically, the internalized NPs should be non-toxic to the NSCs during transport and then activate when the tumor is reached.

The combination of NSCs and AuNRs allows for a targeted, drug-free, photothermal treatment approach to cancer treatment. The NSCs provide a tumor tropic delivery system that is able to traverse the BBB and penetrate poorly vascularized tumor regions (Zhao et al. 2008). In the Examples below, in vitro and in vivo studies demonstrate that NSCs are able to internalize AuNRs for photothermal ablation of tumor cells. No significant changes in viability or tumor tropism were found for NSCs that internalized AuNRs (NSC.AuNRs) as compared to control NSCs. Significantly, when stimulated with a NIR laser, the NSC.AuNRs are able to eradicate tumor cells.

Materials and Methods

Cell Culture.

The human NSC line HB1.F3.CD was maintained in Dulbecco's Modified Eagle Medium (DMEM, Gibco) supplemented with 10% fetal bovine serum (FBS, Gem-Cell), 2 mM L-glutamine (Gibco), 100 U/mL penicillin, and 100 mg/mL streptomycin and maintained at 37° C. under 6% $CO_2$. The same culture medium was used for the human glioblastoma cell line U87 and the human metastatic breast cancer cell line MDA-MB-231-BR. To obtain conditioned media, the cell lines U87 and MDA-MB-231-BR were grown to 80% confluency. Cultures were then rinsed twice with PBS and incubated for 48 hours in serum-free DMEM supplemented with 2 mM L-glutamine, 100 U/mL penicillin and 100 mg/mL streptomycin (Mediatech). After the 48 hour incubation, conditioned media were collected and immediately used to assess migration of NSCs.

Preparation of MUTAB Coated AuNR Solutions.

Strongly bound, 10×41 nm (FIG. 36A) 11-mercaptoundecyltrimethylammonnium bromide (MUTAB) coated gold nanorods (AuNRs) with longitudinal plasmon resonances at 810 nm were supplied by Nanopartz, a division of Concurrent Analytical, Inc. The samples were maintained in DI water at 4° C. at a concentration of 36.1 mg/ml prior to use. MUTAB-AuNR concentrations of [0.01×], [0.1×], and [1×] were calculated using the number of nanoparticles/mL. MUTAB-AuNRs were then centrifuged at 14,000 rpm, 0° C., for 15 mins and gently resuspended into the appropriate volume of FBS containing DMEM prior to NSC loading with each concentration.

Loading NSCs with MUTAB-AuNRs.

NSCs are first cultured to 80% confluency in DMEM supplemented with 10% FBS, 2 mM L-glutamine, 100 U/mL penicillin, and 100 mg/mL streptomycin. NSCs are grown to 80% confluency and then plated at a density of $1\times10^5$ cells/cm$^2$ for 24 hours prior to MUTAB-AuNR treatment. Already prepared MUTAB-AuNR solutions at concentrations of [0.01×], [0.1×], and [1×] will then be incubated with the NSCs for 16 hours. After 16 hours, NSCs will be thoroughly washed several times with FBS containing DMEM to remove any remaining MUTAB-AuNRs in the media not taken up by the NSCs.

Assessment of NSC Viability after MUTAB-AuNR Treatment.

In order to assess NSC viability after MUTAB-AuNR uptake, Guava EasyCyte technology, a PicoGreen DNA quantification assay, and a LIVE/DEAD stain were used. NSCs were cultured and treated with MUTAB-AuNRs at concentrations of [0.01×], [0.1×], and [1×] as previously described. First, Guava EasyCyte was employed, which is a flow cytometer used for cell counting and viability. Briefly, cells were transferred to a 96 well v-bottom plate and centrifuged for 5 mins at 1,500 rpm. Treated and nontreated NSCs were gently resuspended in a 1:1 of PBS to ViaCount and viability was assessed using Guava EasyCyte software. Next, a PicoGreen DNA quantification assay was used as another method to assess viability by correlation of the amount of DNA to cell number. A standard curve using Quick Load 100 bp DNA was prepared for quantification of DNA in NSC samples. Cells were treated first with Triton X-100 detergent solution for 15 mins at room temperature. Following cell lysis, samples of DNA from each NSC condition were added to TE buffer and PicoGreen dye in a 384 well plate in duplicate-triplicates. DNA standards and samples were then read using a SpectraMax microplate reader. Further, LIVE/DEAD is a fluorescence-based cellular viability assay that can discriminate between a population of live cells from dead cells. To prepare the LIVE/DEAD solution, 4 μL of calcein AM (stains live cells green) and 1 μL EtBr (stains dead cells red) were added to 2 mL to PBS. Complete media was removed from each condition and cells were incubated in the LIVE/DEAD solution at room temp in the dark for 15 mins. The stained cells were then imaged using a Nikon Eclipse TE2000-U Fluorescent microscope (Nikon Instruments) under 10× magnification.

Transmission Electron Microscopy of MUTAB-AuNR Uptake by NSCs.

To determine whether MUTAB-AuNRs were internalized by NSCs, transmission electron microscopy (TEM) was employed. Approximately 8-10 million cells are grown in a T175 flask and incubated with MUTAB-AuNRs for 16 hours. MUTAB solutions were then removed, cells were trypsinized and centrifuged, and a the cell pellets were fixed with 2% glutaraldehyde in 0.1 M Cacodylate buffer (Na $(CH_3)_2AsO_2.3H_2O$), pH 7.2, at 4° C., overnight. The cell pellets were washed three times with 0.1 M Cacodylate buffer, pH 7.2, fixed with 1% $OsO_4$ in 0.1 M Cacodylate buffer for 30 mins and washed three times with 0.1 M Cacodylate buffer. The samples were then dehydrated through 60%, 70%, 80%, 95% ethanol, 100% absolute ethanol (twice), propylene oxide (twice), and were left in propylene oxide/Eponate (1:1) overnight at room temperature. The next day the vials were left open for 2-3 hours to evaporate the propylene oxide. The samples were infiltrated with 100% Eponate and polymerized at ~64° C. for 48 hours. Ultra-thin sections (~70 nm thick) were cut using a Leica Ultra cut UCT ultramicrotome with a diamond knife and picked up on 200 mesh copper EM grids. Grids were stained with 2% uranyl acetate for 10 minutes followed Reynold's lead citrate staining for 1 minute. Electron microscopy was done on an FEI Tecnai 12 transmission electron microscope equipped with a CCD camera.

Dark Field Imaging of MUTAB-AuNR Uptake by NSCs.

Dark field microscopy was used in conjunction with TEM to confirm uptake of MUTAB-AuNRs by NSCs. Cells were grown on No. 1 cover slips and treated with MUTAB-AuNR solutions accordingly. Post MUTAB-AuNR treatment, NSCs were fixed in 4% Paraformaldehyde and No. 1 cover slips were transferred to a glass slide and imaged under oil immersion at 60× magnification. The CytoViva Hyperspectral Imaging System (HSI) was used to provide spectral analysis of the MUTAB-AuNRs.

ICP-MS Measurement of MUTAB-AuNR Uptake by NSCs.

NSCs were loaded with MUTAB-AuNRs at [0.1×], [1×] and [10×] concentrations as described. MUTAB-AuNR loaded NSCs were carefully washed with PBS buffer (1×) three times to remove unloaded MUTAB-AuNR. Then ultrapure Nitric Acid (5%) was added to dissolve the MUTAB-AuNR loaded NSCs. Au concentrations were determined with an HP 4500 series ICP-MS. Nebulization was effected with a flow of 1.3 liters per minute of argon using a Teflon concentric nebulizer in a teflon Scott-type spray chamber. A platinum inject transferred sample aerosol into the plasma. The argon plasma power was 1150 W with a flow of 15 liters per minute and an auxiliary flow of 1.1 liters per minute. Data was analyzed quantitatively in a spreadsheet program using external standardization.

In Vitro Transwell Boyden Migration Assay.

NSCs were loaded with MUTAB-AuNRs at [0.01×], [0.1×], and [1×] concentrations and conditioned media was prepared as described. In a 24-well tissue culture plate 500 μL of target media (BSA negative control, U87 positive control, and MDA-MB-231-BR metastatic breast cancer cell lines) was added to each well. At a density of 1×10$^5$ cells/well, MUTAB-AuNR loaded NSCs in DMEM and 5% w/v BSA were placed in the Transwell chambers and incubated at 37° C. for 4 hours. After the incubation period, the Transwell chambers were placed in a new 24-well tissue culture plate containing accutase and incubated 10 mins at 37° C. Detached cells were then transferred to a 96 well v-bottom plate, centrifuged at 1,500 rpm for 5 mins, and resuspended in 1:1 PBS to ViaCount. NSC migration to conditioned media of MUTAB-AuNR treated and nontreated cells was assessed using Guava EasyCyte technology.

In Vitro Photothermal Heating of MUTAB-AuNR Loaded NSCs.

To characterize the killing of MUTAB-AuNR loaded NSCs using near-IR laser light, MUTAB concentrations of [0.01×], [0.1×], and [1×] (compared to NSCs alone) were used. Immediately after NSCs were incubated with MUTAB-AuNRs, samples were heated in a 96-well tissue culture plate using a Zeiss LSM 510 two-photon inverted confocal microscope and 10× objective at 810 nm and 2,000 mW for 100 iterations. A targeted region was heated in each condition. Brightfield images were taken before and after heating. Post-heating, treated and nontreated NSCs were stained with calcein AM LIVE solution and imaged with a 5× objective to clearly visualize the targeted region.

Assessment of TNBC Killing Effect In Vitro Using Near-IR Laser Heating by Co-Culturing MUTAB-AuNR Loaded NSCs and MDA-MB-231-BR.

NSCs were loaded with concentrations of [0.01×], [0.1×], and [1×] MUTAB-AuNRs as previously described. MDA-MB-231-BR cells were plated in a 96-well tissue culture plate at a density of 1×10$^5$ cells/cm$^2$ concurrently to the NSCs incubation with MUTAB-AuNRs. After the 16-hour incubation period, NSCs at each condition were detached with trypsin-EDTA (Gibco) and transferred to the wells containing MDA-MB-231-BR cells at ratios of 1:1, 1:10, 1:100, 1:1,000, and 1:10,000 by using serial dilutions. The number of NSCs treated and untreated were counted and adjusted to number of MDA-MB-231-BR cells in a sample cell count. Each condition and ratio was done in triplicates. Cells were co-cultured for 8 hours and then near-IR laser heated, LIVE stained, and imaged as previously described.

Results and Discussion

To facilitate future translation of NSC.AuNRs towards the clinic, the HB1.F3.CD NSCs were used. The MDA-MB-231-BR human breast cancer cell line was chosen because tumors derived from these cells display many of the challenges the NSC.AuNR therapy is intended to overcome, as they often have large hypoxic areas and frequently metastasize to the brain (Fulford et al. 2006). For the AuNRs, dimensions of 40 nm long by 10 nm in diameter were selected for plasmonic heating to occur when stimulated with an 810 nm NIR laser (Kelly et al. 2002; Link & El-Sayed 1999). As a coating for the AuNRs, 11-mercaptoundecyltrimethylammonnium bromide (MUTAB) was selected due to its cationic charge, which promotes cell uptake, and its ability to covalently bind to the AuNRs (See FIG. 36 for characterization of MUTAB-AuNRs). MUTAB proved a superior coating for uptake and transport of AuNRs by NSCs as compared to the more common coatings cetylammounium bromide, which is toxic when dissociated from the AuNRs (von Maltzahn et al. 2009; Chakraborty et al. 2011; Niidome et al. 2007), and polyethylene glycol, which decreases cell uptake (Niidome et al. 2006; Grabinski et al. 2011; Liu et al. 2007).

First, the impact of MUTAB-AuNR uptake on NSC viability was assessed using three orthogonal viability assays (FIG. 37): Guava EasyCyte technology, which counts live cells by flow cytometry with its specialized DNA binding dyes called ViaCount, PicoGreen DNA quantification, which correlates to the cell number, and LIVE/DEAD staining, a fluorescence-based assay that stains live cells with Calcein AM (green) and dead cells with ethidium bromide (red). NSCs were treated with several concentrations of MUTAB-AuNRs: 5.7×10$^{10}$ NPs/mL, 5.7×10$^{11}$ NPs/mL), 5.7×10$^{12}$ NPs/mL, and 2.85×10$^{13}$ NPs/mL. For clarity and convenience, these concentrations have been denoted as [0.01×], [0.1×], [1×], and [5×] respectively. NSCs exposed to MUTAB-AuNRs at [0.01×], [0.1×], or [1×] had no change in morphology or viability as assessed by the three assays (FIG. 37), and the NSCs continued to proliferate after a 24-hour incubation with the MUTAB-AuNRs (data not shown). When the NSCs were exposed to the [5×] concentration, the number of NSCs counted by the viability assays decreased although the percentage measured as "alive" remained unchanged. At this concentration, NSC morphology also appeared to change slightly, so only [0.01×], [0.1×], or [1×] were further evaluated.

Having determined that NSCs remained viable when exposed to up to [1×] MUTAB-AuNRs, it was next investigated whether the uptake of the MUTAB-AuNRs into the NSCs was dependent on the concentration of MUTAB-AuNRs that the NSCs were exposed to. As mentioned above, the MUTAB coating was selected in large part because the cationic charge was expected to enable efficient cell uptake (Niidome et al. 2007; Huff et al. 2007). MUTAB-AuNRs were incubated for 16 h at concentrations of [0.01×], [0.1×], and [1×] with NSCs and uptake was assessed using transmission electron microscopy (TEM) and dark field imaging (FIG. 38). TEM imaging clearly demonstrated the ability of MUTAB-AuNRs to be taken up and retained in endosomes by the NSCs (FIG. 38A-38D). Moreover, as the concentration of MUTAB-AuNRs was increased, more MUTAB-AuNRs were taken up as indicated by the more densely packed MUTAB-AuNRs in each endosome and the increased number of areas of MUTAB-AuNRs accumulation in each cell. Hyperspectral mapping of dark-field microscopy was performed to image the uptake of the MUTAB-AuNRs over a relatively large area. To establish what hyperspectral signal to map in the experimental samples, first MUTAB-AuNRs alone were imaged by dark-field microscopy and a hyperspectral spectra was recorded for each pixel in the image. A collection of spectra was then obtained by selecting pixels corresponding to the MUTAB-AuNRs. To assess the uptake and distribution of the MUTAB-AuNRs in cells, dark-field images were obtained of MDA-MB-231-BR cells exposed to different concentrations of MUTAB-AuNRs. Then, a mapping was performed on these images to false-color each pixel red that matched one of the hyperspectral spectra from the MUTAB-AuNRs sample. Using this technique, dose dependent uptake of the MUTAB-AuNRs was clearly seen (FIG. 38E-38H). In order to quantify this uptake, inductively coupled plasma mass spectrometry (ICP-MS) was used to analyze the gold content in equal numbers of NSCs exposed to either media alone, or [0.01×], [0.1×], or [1×] MUTAB-AuNRs. ICP-MS measurements demonstrated that the amount of gold internalized by the NSCs increased nearly 10× as the amount of MUTAB-AuNRs the NSCs were exposed to was increased by 10×.

Figure 39:
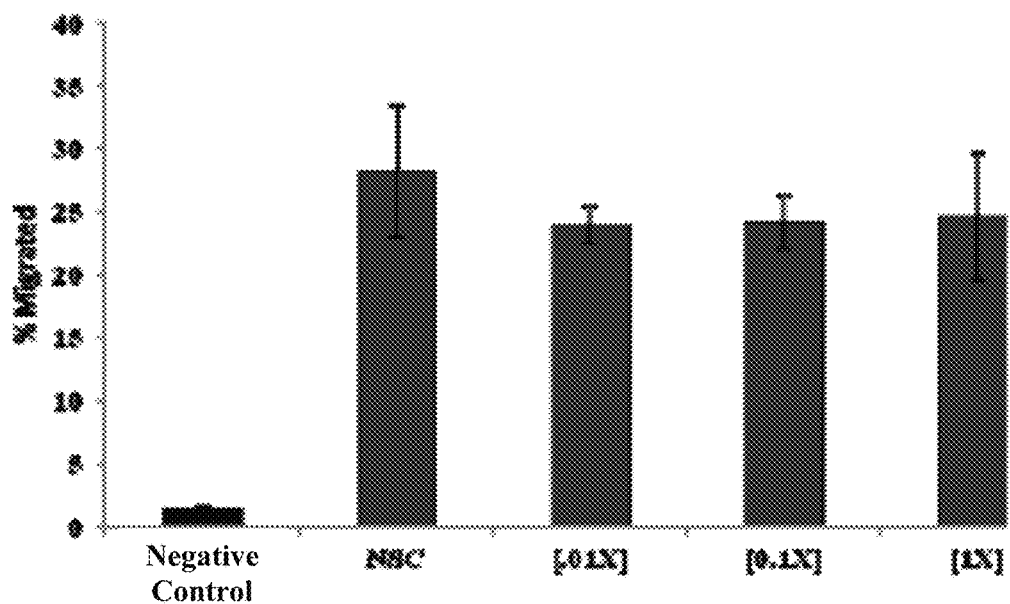
FIG. 39 shows a comparison of chemotaxis toward tumor conditioned media between unloaded NSCs and NSCs loaded with MUTAB-AuNRs in accordance with one embodiment. Migration of NSC.AuNRs to MDA-MB-231-BR conditioned media was assessed using a Boyden chamber assay. Media containing just bovine serum albumin was used as a negative control for chemotaxis (black bar); unloaded NSCs (red bar) were used as a positive control. Migration to the tumor conditioned media was unimpaired for all NSC.AuNRs. Conditions were done in triplicates; bars, SD.

Having demonstrated that significant uptake of MUTAB-AuNRs did not affect NSC viability, the ability of the NSC.AuNRs to migrate towards tumor specific signals was evaluated. An in vitro Transwell Boyden migration assay was used to measure NSC.AuNRs movement towards tumor conditioned media. In this assay, the NSC.AuNRs or just NSCs (positive control) were loaded on top of a thick porous membrane and the bottom of the membrane was immersed in either media containing just bovine serum albumin (negative control) or media that had been used to grow MDA-MB-231-BR cells (tumor conditioned media). After 4 h, the number of NSCs that had migrated through the membrane was counted. No difference in chemotaxis towards the tumor conditioned media was observed between the unloaded NSCs and NSCs loaded with MUTAB-AuNRs at [0.01×], [0.1×], or [1×] (FIG. 39). NSC.AuNRs robustly migrated towards MDA-MB-231-BR conditioned media suggesting that NSCs retain their tumor tropism post-AuNR loading.

Figure 40:
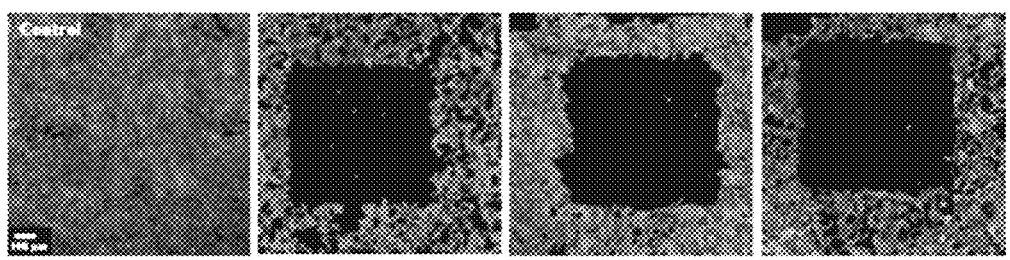
FIG. 40 shows NSCs that were incubated with (A) media alone, (B) [0.01×], (C) [0.1×], or (D) [1×] MUTAB-AuNRs, then a square in the center of the image was exposed to an 810 nm laser (2 W/cm$^2$, 3 min) and the entire area was stained with Calcium AM (live cells green) in accordance with one embodiment. Control NSCs were unaffected by NIR laser light, while NSC.AuNRs were completely eliminated in the exposed region.
Figures 41A, 41B, 41C, 41D:
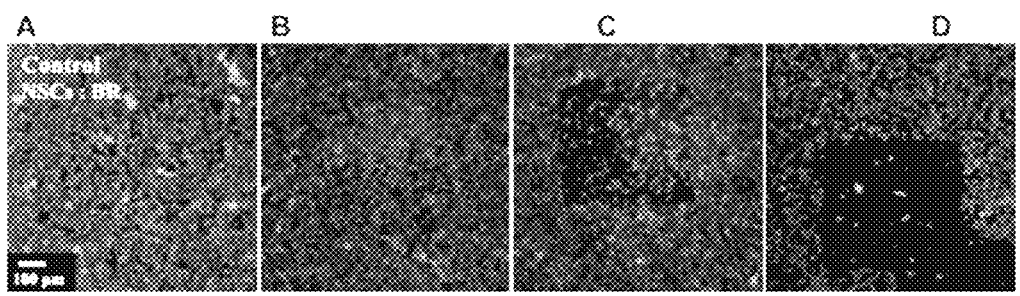
FIG. 41 shows NSCs alone (A) or loaded with MUTAB-AuNRs at [0.01×] (B), [0.1×] (C), or [1×] (D) were co-cultured with MDA-MB-231-BR cells in a 1:1 ratio.
Figures 42A, 42B, 42C:
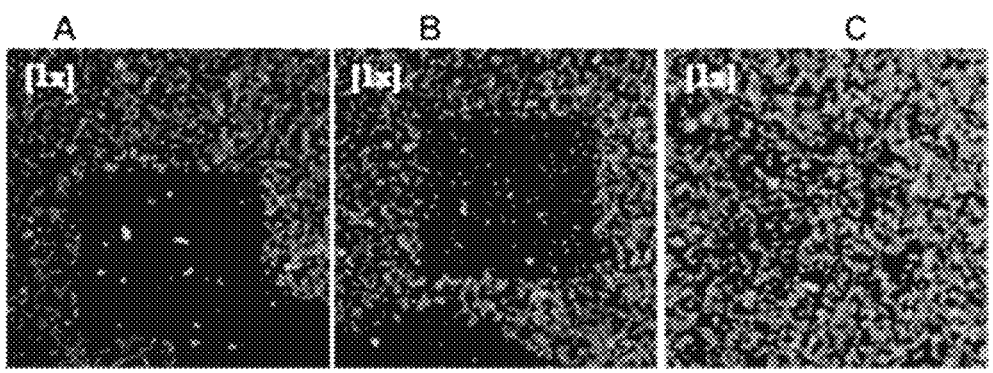
FIG. 42 shows NSCs loaded with [1×] MUTAB-AuNRs were co-cultured with cancer cells in a 1:1 ratio(A), a 1:10 ratio (B), and a 1:100 ratio (C) in accordance with one embodiment. In all cases, a square in the center of the co-cultures was exposed to an 810 nm laser (2 W/cm$^2$, 3 min) and then the entire area was stained with Calcein AM (live cells green) and imaged.

Having shown that NSCs maintained their viability and tumor tropism upon loading with MUTAB-AuNRs, photothermal ablation of MDA-MB-231-BR cells by NSC.AuNRs was demonstrated. It was first verified that the MUTAB-AuNRs maintained their laser heating properties after being internalized by NSCs (FIG. 40).

Samples of NSCs alone and NSCs exposed to [0.01×], [0.1×], or [1×] MUTAB-AuNRs were prepared in a 96 well plate in triplicates. A small square in the center of each well was exposed to an 810 nm Ti-sapphire two-photon laser at 2 W/cm$^2$ using a pulse sequence in which each pixel was exposed for 1.6 μs one hundred times, as a result of the number of pixels exposed there was a delay of 1.7 s between each exposure for an individual pixel. Thus, each area of the square was exposed for a total of 160 μs during a total scan time of approximately 3 min. Following NIR laser treatment, each well was stained with calcein AM and imaged. Control NSCs were unaffected by exposure to the NIR laser, whereas for all three concentrations of MUTAB-AuNRs tested, the NSC.AuNRs were completely eliminated in the treatment region.

Moreover, the ability of NSC.AuNRs to kill MDA-MB-231-BR cells upon exposure to NIR light was evaluated. For these experiments, NSCs or NSC.AuNRs were initially co-cultured with MDA-MB-231-BR cells in a 1:1 ratio. The same methodology as described above for NSC.AuNRs alone was followed. However, in this case, there was a dramatic difference between the different NSC(AuNR)s. The NSC.AuNRs prepared with [0.01×] MUTAB-AuNRs were unable to achieve cell killing in the coculture conditions. Some cell killing was observed for NSC.AuNRs prepared with [0.1×] MUTAB-AuNRs, while those prepared with [1×] were able to generate enough heat to eliminate nearly all of the cells, both NSCs and cancer cells, in the treated region. Thus, the [1×] NSC.AuNRs were further tested at ratios of 1:10 and 1:100 for NSCs:cancer cells. Significant cell killing was still observed at the 1:10 ratio, but at the 1:100 ratio only slight cell killing was observed (FIGS. 7A-7C).

Figures 43A, 43B, 43C, 43D:
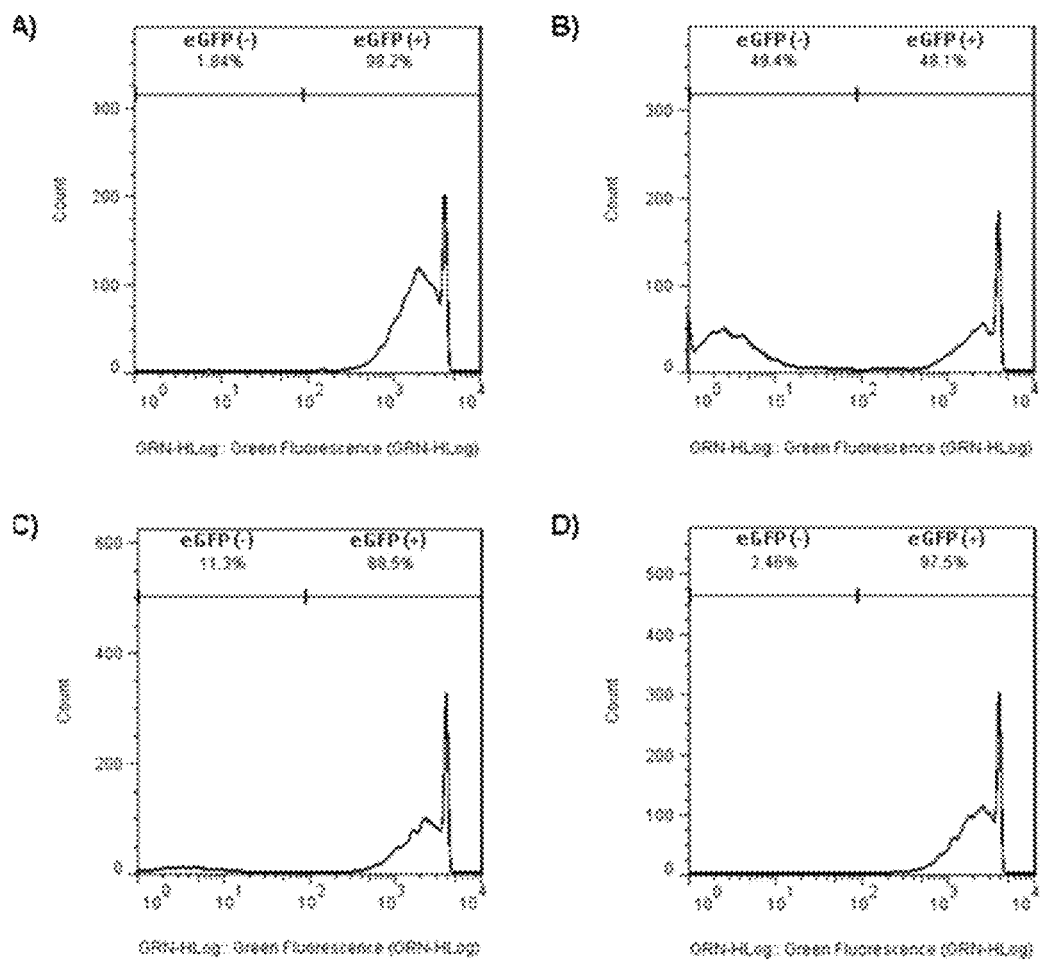
FIG. 43 illustrates quantification of the fraction of HB1.F3 NSCs and MDA-MB-231.BR.eGFP tumor cells contained within co-cultures immediately before laser heating using flow cytometry in accordance with one embodiment. Prior to analysis, freshly trypsinized co-cultures were rinsed with PBS and diluted to a concentration of 2×10$^6$ cells/ml. The fraction of eGFP (+) tumor cells and eGFP (−) NSCs present in each culture was quantified using a Guava EasyCyte flow cytometer and FlowJo software. Representative flow cytometric analyses of a) MDA-MB-231.BR.eGFP only cultures or b-d) NSC: MDA-MB-231.BR.eGFP co-cultures are shown. The ratio of NSCs: tumor cells in the co-cultures decreased from b) 1:1; to c) 1:10; to d) 1:100.

Additionally, fluorescence-activated cell sorting measurements confirming the ratios of NSCs to cancer cells for the thermal ablation experiments, as shown in FIG. 43.

These results demonstrate efficient cellular uptake of MUTAB coated AuNRs by NSCs, with the NSC.AuNRs maintaining their viability and tumor tropism. When exposed to NIR laser light, the NSC.AuNRs efficiently kill surrounding cancer cells. This effect is correlated with AuNR loading in a dose dependent fashion and the most efficient killing demonstrated was 10 cancer cells for every NSC. The work reported here represents a proof-of-principle for the development of NSCs as tumor specific delivery agents for AuNRs, or other internalized responsive nanoparticles, to enable efficient photothermal tumor ablation.

Figure 44:
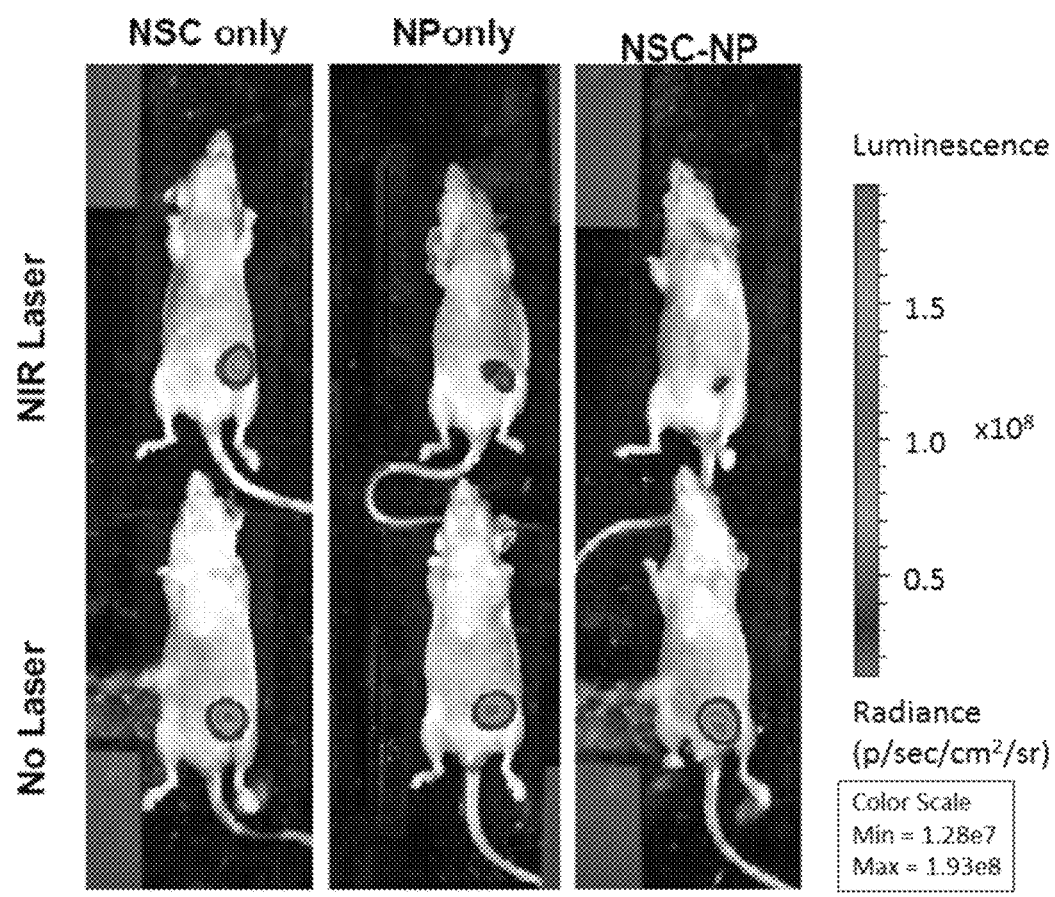
FIG. 44 illustrates photothermal destruction of human breast cancer tumors in mice using NSC-loaded AuNPs. Mice harboring MDA-MB-231 tumors were treated with NSCs only (left panel), NPs only (center panel), or NSCs loaded with NPs (right panel). When treated with near infrared radiation (NIR Laser) (811 nm, 2 W/cm2, 2 min), tumors shrunk (see upper right image) when compared to mice that were not treated with near infrared radiation (No Laser).

Example 7: AuNP-Hybrids for Photothermal Ablation of Triple Negative Breast Cancer To demonstrate that human breast cancer tumors can be targeted and eradicated, mice harboring MDA-MB-231tumors in the 4th mammary fat pad were injected intratumorally with either NSCs only, NPs only, or NSCs loaded with NPs. 72 hours were allowed for any free NPs to clear from circulation, then the tumors of half the mice in each group were exposed to near infrared radiation (NIR) (811 nm, 2 W/cm2, 2 min). Xenogen imaging was performed 4 days later to visualize changes in tumor burden in each animal group. As shown in FIG. 44, treatment with NIR resulted in a reduced tumor size, indicating that the NSCs loaded with NPs resulted in targeted destruction of tumor cells.

Generation of pH Sensitive AuNP-Hybrids.

Figure 45:
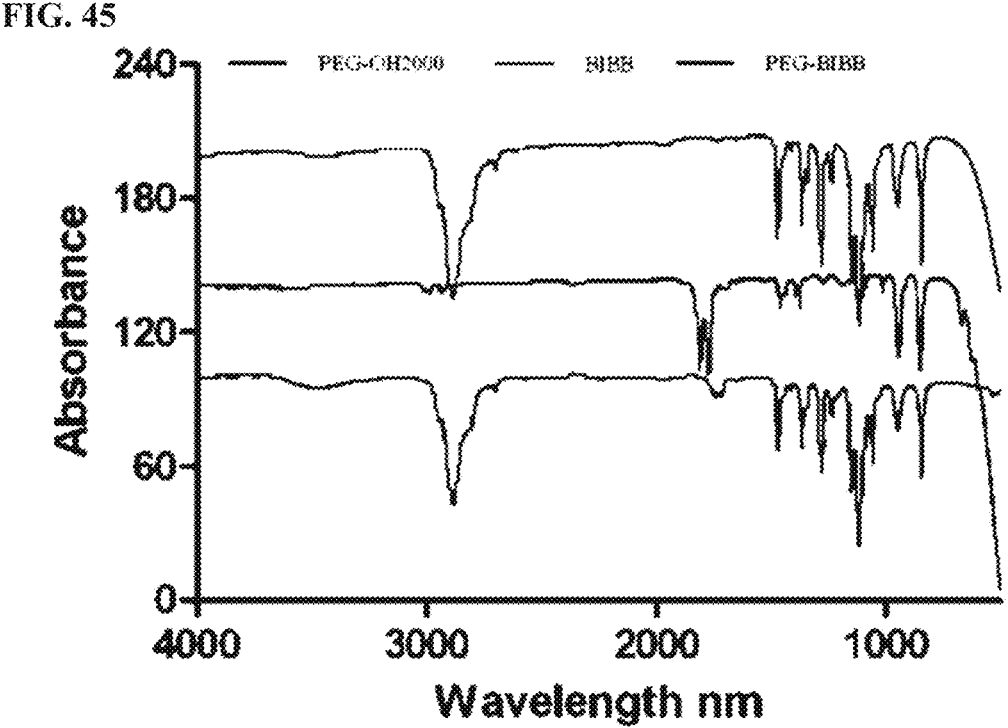
FIG. 45 is an FTIR analysis, illustrating the development of drug-loaded polymeric NP-NSC hybrids for triple negative breast cancer treatment.
Figure 46:
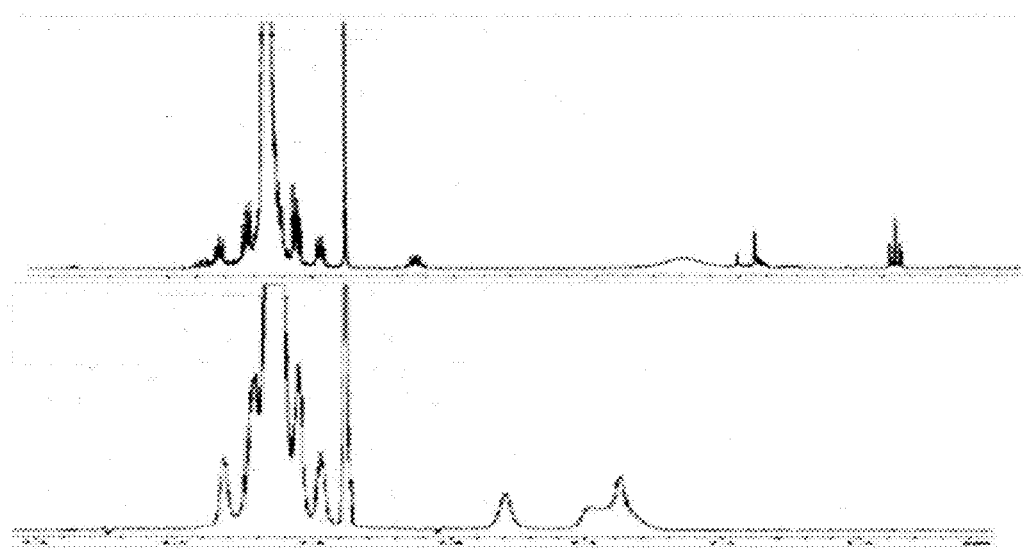
FIG. 46 shows the results of an NMR analysis used to confirm synthesis of the initiators needed for pH-responsive polymer synthesis.

Drug-loaded Polymeric NP-NSCs Hybrids for Triple Negative Breast Cancer Treatment were generated and their synthesis of the initiators needed for a pH-responsive polymer was confirmed by Fourier transform infrared spectroscopy (FTIR) and nuclear magnetic resonance (NMR) (FIGS. 45-46).

Figure 47A:
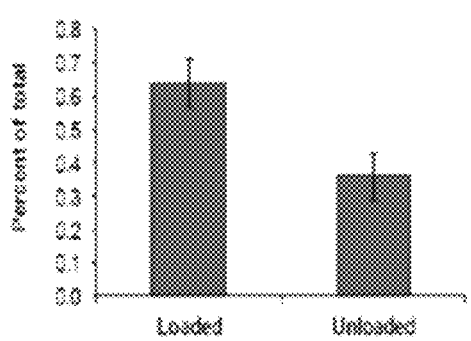
FIG. 47 shows quantification of the loading of the small molecule nile red into pH-responsive particles (A); the release of the small molecule nile red from particles in solutions of decreasing pH (B); and the 1050 of particle loaded Doxetaxel demonstrating killing efficacy against MDA.MB.231 (C) by fluorimetric analysis.
Figure 47B:
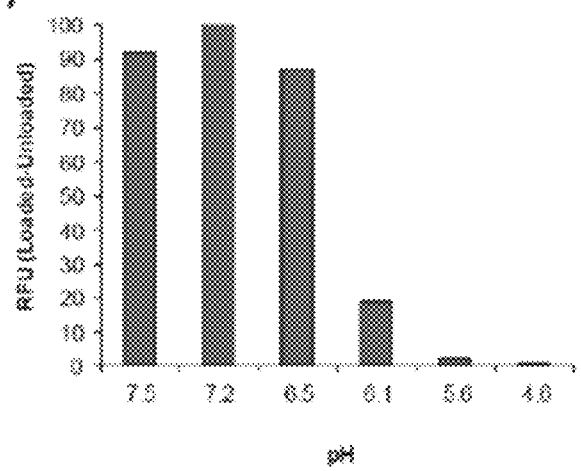
Figure 47C:
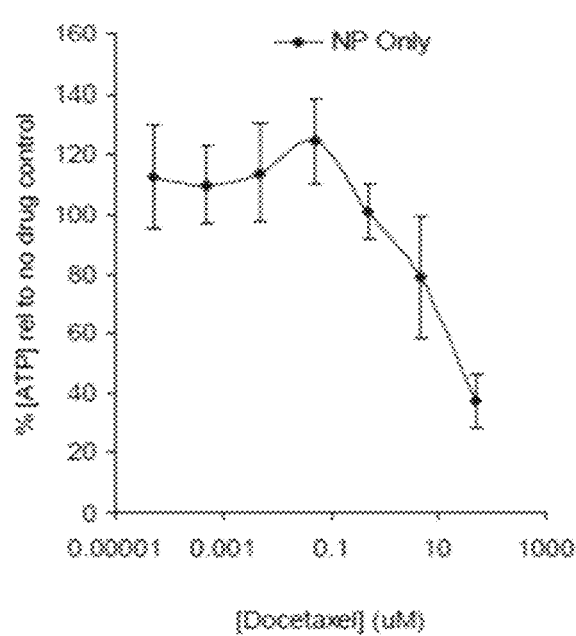

Loading of the small molecule nile red into the pH-responsive particles and the release of nile red from particles in solutions of decreasing pH were quantified using fluorimetric analyses (FIGS. 47A-47B). Further, the IC50 of particle loaded Doxetaxel demonstrated killing efficacy against MDA.MB.231 (FIG. 47C).

Figures 48A, 48B, 48C, 48D:
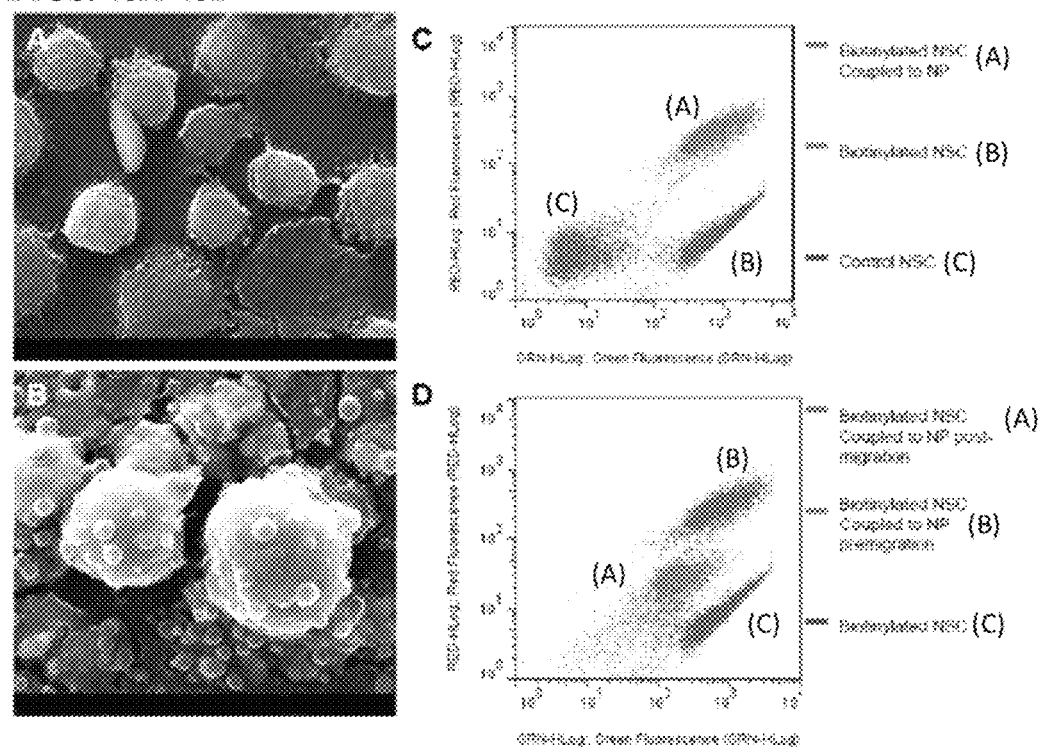
FIG. 48 A-B) Scanning electron microscopy was used to visualize both A) control NSCs; and B) Biotinylated NSCs that were avidin-linked to docetaxel-loaded, biotinylated pH-responsive NPs. C) FACs analysis was employed to confirm efficient avidinylation of NSCs (blue cells) where the avidin-fitc caused a right shift relative to the control NSCs (red cells). Upon coupling to nile-red loaded NPs, an upward shift occurred (yellow cells). D) FACs analysis was also performed after putting NSCs through an in vitro tumor tropism challenge. While some of the particles were lost post migration (yellow cells) relative to pre-migration (Blue cells); there were still particles present on the cells post-migration.

Scanning electron microscopy was then used to visualize both control NSCs (FIG. 48A) and biotinylated NSCs (FIG. 48B) that were avidin-linked to docetaxel-loaded, biotinylated pH-responsive NPs. FACs analysis was employed to confirm efficient avidinylation of NSCs where the avidin-fitc caused a right shift relative to the control NSCs (FIG. 48C). Upon coupling to nile-red loaded NPs, an upward shift occurred. FACs analysis was also performed after putting NSCs through an in vitro tumor tropism challenge (FIG. 48D). While some of the particles were lost post-migration relative to pre-migration, particles were still present on the cells post-migration.

Figure 49:
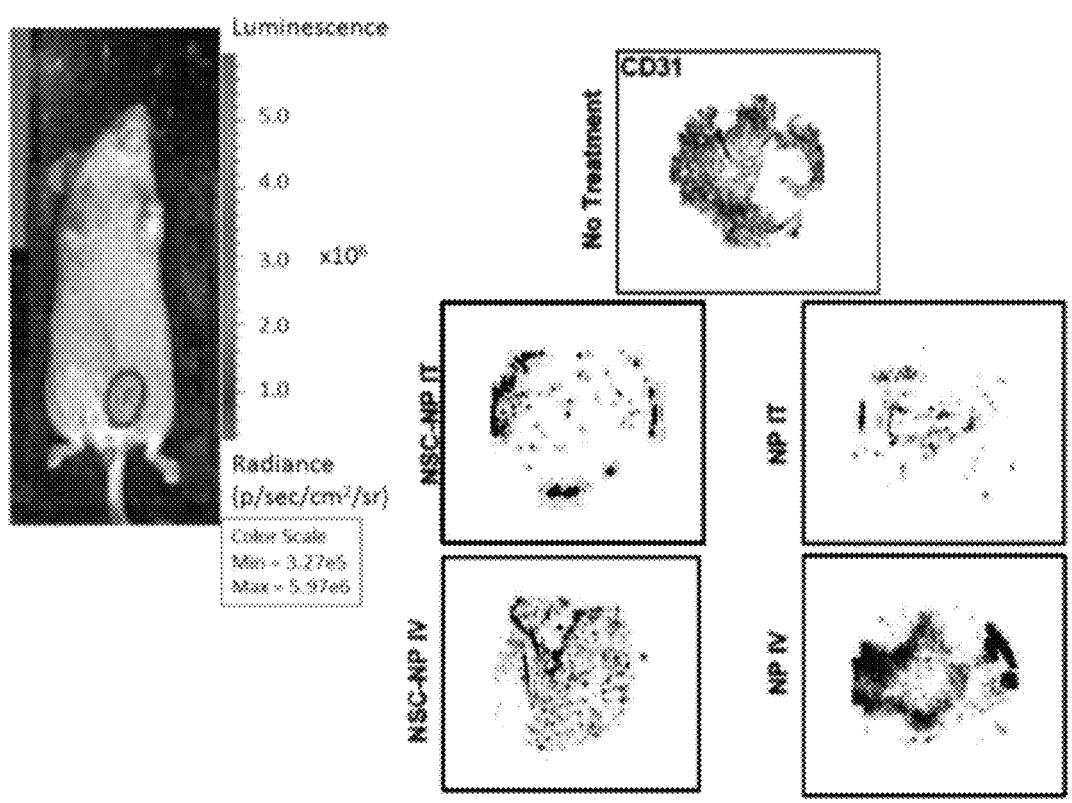
FIG. 49 Mice harboring MDA-MB-231 tumors in the 4th mammary fat pad were injected either intratumorally (IT) or intravenously (IV) with either Saline control, NSC-NPs or free-NPs. The NPs in each case were pH-responsive, docetaxel loaded NPs that should release their drug cargo within the acidic tumor environment. One week after treatment, mice were sacrificed, tumors harvested, fixed, cryosectioned and mounted on glass slides. Immunohistochemistry was performed to visualize the blood vessel density within the tumors (anit-CD31 staining) in each group. Reconstruct software was used to trace all positive vessels, and a map of representative tumor slice is shown for each group.

To demonstrate the efficacy of the pH-responsive particles, mice harboring MDA-MB-231tumors in the 4th mammary fat pad were injected either intratumorally (IT) or intravenously (IV) with either Saline control, NSC-NPs or free-NPs. The NPs in each case were pH-responsive, docetaxel loaded NPs that should release their drug cargo within the acidic tumor environment. One week after treatment, mice were sacrificed, tumors harvested, fixed, cryosectioned and mounted on glass slides. Immunohistochemistry was also performed to visualize the blood vessel density within the tumors (anit-CD31 staining) in each group. Reconstruct software was used to trace all positive vessels, and a map of representative tumor slice is shown for each group. As shown in FIG. 49, treatment with NSC-NP improved the targeting and destruction of tumor cells, as indicated by a reduction of cellular tissue in the left panels (FIG. 49, NSC-NP IT and NSC-NP IV).

REFERENCES

The references cited in the specification above and those listed below are hereby incorporated by reference as if fully set forth herein.

Aboody, K. S.; Brown, A.; Rainov, N. G.; Bower, K. A.; Liu, S.; Yang, W.; Small, J. E.; Herrlinger, U.; Ourednik, V.; Black, P. M.; Breakefield, X. O.; Snyder, E. Y., Neural stem cells display extensive tropism for pathology in adult brain: evidence from intracranial gliomas. *Proc Natl Acad Sci USA* 2000, 97 (23), 12846-12851.

Aboody, K. S.; Najbauer, J.; Schmidt, N. O.; Yang, W.; Wu, J. K.; Zhuge, Y.; Przylecki, W.; Carroll, R.; Black, P. M.; Perides, G., Targeting of melanoma brain metastases using engineered neural stem/progenitor cells. *Neuro-Oncology* 2006, 8 (2), 119-126.

Aboody, K., et al., *Translating Stem Cell Studies to the Clinic for CNS Repair: Current State of the Art and the Need for a Rosetta Stone*. Neuron. 2011. 70(4): p. 597-613.

Acharya S, Sahoo S K. PLGA nanoparticles containing various anticancer agents and tumour delivery by EPR effect. Advanced Drug Delivery Reviews. In press. doi: 10.1016/j.addr.2010.10.008.

Allard, E., C. Passirani, and J. P. Benoit, *Convection-enhanced delivery of nanocarriers for the treatment of brain tumors*. Biomaterials. 2009 April; 30(12):2302-18. Epub 2009 Jan. 24.

Allard, E., et al., *188Re-loaded lipid nanocapsules as a promising radiopharmaceutical carrier for internal radiotherapy of malignant gliomas*. Eur J Nucl Med Mol Imaging. 2008 October; 35(10):1838-46. Epub 2008 May 9.

Alon, R., E. A. Bayer, and M. Wilchek, *Cell adhesion to streptavidin via RGD-dependent integrins*. Eur J Cell Biol. 1993 February; 60(1):1-11.

Arbab A S, Yocum G T, Rad A M et al. Labeling of cells with ferumoxides-protamine sulfate complexes does not inhibit function or differentiation capacity of hematopoietic or mesenchymal stem cells. NMR Biomed. 18: 553-559. 2005.

Arbab A S, Yocum G T, Wilson L B et al. Comparison of transfection agents in forming complexes with ferumoxides, cell labeling efficiency, and cellular viability. Mol Imaging. 3: 24-32. 2004.

Aryal S, Hu C, Zhang L. Polymer-cisplatin conjugate nanoparticles for acid-responsive drug delivery. ACS nano. 4: 251-258. 2010.

Barth R F. Rat brain tumor models in experimental neurooncology: the 9L, C6, T9, F98, RG2, D74, RT-2, and CNS-1 gliomas. Journal of Neruooncology 1998; 36: 91-102.

Bobola M S, Tseng S H, Blank A, Berger M S, Silber J R. Role of O6-methylguanine-DNA methyltransferase in resistance of human brain tumor cell lines to the clinically relevant methylating agents temozolomide and streptozotocin. Clin Cancer Res, 2, 735, 1996.

Brady L. Martin, A. A., Ken Kubota, Karl Sillay, Marina E. Emborg, *Pathways of Flow for Infusions ino the Putamen*. (http://kineticsfoundation.org/wp-content/uploads/2012/06/PutamenInfusions20120415.pdt)

Brown, A. B., et al., *Intravascular delivery of neural stem cell lines to target intracranial and extracranial tumors of neural and non-neural origin*. Hum Gene Ther. 2003 Dec. 10; 14(18):1777-85.

Brownell G L, Marcum D, Hoop J R, Bohing B R. Quantitative dynamic studies using short-lived radioisotopes and positron detection in Proceedings of the Symposium on Dynamic Studies with Radioisotopes in Medicine, Rotterdam. IAEA. Vienna. 161, 1970.

Bryant S, Anseth K, Hydrogel properties influence ECM production by chondrocytes photoencapsulated in poly (ethylene glycol) hydrogels. J. Biomed. Mater. Res. 59: 63-72. 2002.

Burke, A. R.; Singh, R. N.; Carroll, D. L.; Wood, J. C. S.; D'Agostino Jr, R. B.; Ajayan, P. M.; Torti, F. M.; Torti, S. V., The resistance of breast cancer stem cells to conventional hyperthermia and their sensitivity to nanoparticle-mediated photothermal therapy. *Biomaterials* 2012, 33 (10), 2961-2970.

Carare, R. O., et al., *Solutes, but not cells, drain from the brain parenchyma along basement membranes of capillaries and arteries: significance for cerebral amyloid angiopathy and neuroimmunology*. Neuropathol Appl Neurobiol. 2008 April; 34(2):131-44. Epub 2008 Jan. 16.

Castro M G, Cowen R, Williamson I K, David A, Jimenez-Dalmaroni M J, Yuan X, Bigliari A, Williams J C, Hu J, Lowenstein P R. Current and future strategies for the treatment of malignant brain tumors. Pharmacol. Ther 2003; 98: 71-108.

Chakraborty, S.; Joshi, P.; Shanker, V.; Ansari, Z. A.; Singh, S. P.; Chakrabarti, P., Contrasting effect of gold nanoparticles and nanorods with different surface modifications on the structure and activity of bovine serum albumin. *Langmuir* 2011, 27 (12), 7722-7731.

Chen, J.; Wang, D.; Xi, J.; Au, L.; Siekkinen, A.; Warsen, A.; Li, Z. Y.; Zhang, H.; Xia, Y.; Li, X., Immuno gold nanocages with tailored optical properties for targeted photothermal destruction of cancer cells. *Nano Lett* 2007, 7 (5), 1318-1322.

Chen, M. Y., et al., *Surface properties, more than size, limiting convective distribution of virus-sized particles and viruses in the central nervous system*. J Neurosurg. 2005 August; 103(2):311-9.

Cheng, H.; Kastrup, C. J.; Ramanathan, R.; Siegwart, D. J.; Ma, M.; Bogatyrev, S. R.; Xu, Q.; Whitehead, K. A.; Langer, R.; Anderson, D. G., Nanoparticulate cellular patches for cell-mediated tumoritropic delivery. *ACS Nano* 2010, 4 (2), 625-631.

Christofk H, Heiden M, Harris M, Ramanathan A, Gerszten R, Wei R, Fleming M, Schreiber S, Cantley L. The M2 splice Isoform of Pyruvate Kinase Is Important for Cancer Metabolism and Tumour Growth. Nature. 452: 230-233. 2008.

Claes A, Idema A J, Wesseling P. Diffuse glioma growth: a guerilla war. Acta Neuropathology 2007; 114: 443-458.

Clapper J, Pearce M, Guymon C, Aliasger K. Biotinylated Biodegradable Nanotemplated Hydrogel Networks for Cell Interactive Applications. Biomacromolecules 9: 1188-1194. 2008.Cohen S. Controlled delivery systems for proteins based on poly(lactic/glycolic acid) microspheres. Pharmaceutical Research 1991; 8: 713-720.

Cole, J. R.; Mirin, N. A.; Knight, M. W.; Goodrich, G. P.; Halas, N. J., Photothermal Efficiencies of Nanoshells and Nanorods for Clinical Therapeutic Applications. *The Journal of Physical Chemistry C* 2009, 113 (28), 12090-12094.

Connor, E. E.; Mwamuka, J.; Gole, A.; Murphy, C. J.; Wyatt, M. D., Gold nanoparticles are taken up by human cells but do not cause acute cytotoxicity. *Small* 2005, 1 (3), 325-327.

Cowen R L, Williams J C, Emery S, Blakey D, Darling J L, Lowenstein P R, Castro M G. Adenovirus vector-mediated delivery of the pro-drug converting enzyme carboxypeptidase G2 in a secreted or GPI-anchored form: High-level expression of this active conditional cytotoxic enzyme at the plasma membrane. Cancer Gene Therapy 2002; 9: 897-907.

Cui W, Lu X, Cui K, Wu J, Wei Y, Lu Q. Photosensitive nanoparticles of chitosan complex for controlled release of dye molecules. Nanotechnology, 22, 065702, 2011.

Daniel, M. C.; Astruc, D., Gold nanoparticles: assembly, supramolecular chemistry, quantum-size-related properties, and applications toward biology, catalysis, and nanotechnology. *Chem Rev* 2004, 104 (1), 293-346.

Danks, M. K.; Yoon, K. J.; Bush, R. A.; Remack, J. S.; Wierdl, M.; Tsurkan, L.; Kim, S. U.; Garcia, E.; Metz, M. Z.; Najbauer, J.; Potter, P. M.; Aboody, K. S., Tumor-targeted enzyme/prodrug therapy mediates long-term disease-free survival of mice bearing disseminated neuroblastoma. *Cancer Res* 2007, 67 (1), 22-25.

Decuzzi, P., et al., *Size and shape effects in the biodistribution of intravascularly injected particles*. Journal of Controlled Release. 2010. 141(3): p. 320-327.

Deeken J F, Loscher W. The blood-brain barrier and cancer: transporters, treatment, and Trojan horses. Clinical Cancer Research 2007; 13: 1663-1674.

Desanknai S, Lumniczky K, Esik O, Hamada H, Safrany G. Local Tumor irradiation enhances the anti-tumor effect of a double-suicide gene therapy system in a murine glioma model. The Journal of Gene Medicine 2003; 5: 377-385.

Ehtesham M, Kabos P, Gutierrez M A R, Chung N H C, Griffith T S, Black K L, Yu J S. Induction of glioblastoma apoptosis using neural stem cell-mediated delivery of tumor necrosis factor-related apoptosis-inducing ligand. Cancer Research 2002; 62: 7170-7174.

Ehtesham M, Kabos P, Kabosova A, Neuman T, Black K L, Yu J S. The use of interleukin 12-secreting neural stem cells for the treatment of intracranial glioma. Cancer Research 2002: 62; 5657-5663.

Elias M C, Tozer K R, Silber J R, Mikheeva S, Deng M, Morrison R S, Manning T C, Silbergeld D L, Glackin C A, Reh T A, Rostomily, R C. TWIST is Expressed in Human Gliomas and Promotes Invasion. Neoplasia, 7, 824, 2005.

El-Sayed, I. H.; Huang, X.; El-Sayed, M. A., Selective laser photo-thermal therapy of epithelial carcinoma using anti-EGFR antibody conjugated gold nanoparticles. Cancer Letters 2006, 239 (1), 129-135.

Eseonu, C., *Intracranial Drug Delivery of siRNA Nanopartides to Tumor Cells*. ProQuest Dissertations and Theses, 2011. Biomedical engineering.

Eskandary, H., et al., *The role of stem cells in tumor targeting and growth suppression of gliomas*. Biologics. 2011; 5:61-70. Epub 2011 Apr. 5.

Fang, J., H. Nakamura, and H. Maeda, *The EPR effect: Unique features of tumor blood vessels for drug delivery, factors involved, and limitations and augmentation of the effect*. Adv Drug Deliv Rev. 2011 Mar. 18; 63(3):136-51. Epub 2010 May 2.

Fay, F.; Scott, C. J., Antibody-targeted nanoparticles for cancer therapy. *Immunotherapy* 2011, 3 (3), 381-394.

Fernandez A M, Fernandez A, Carrero P, Garcia-Garcia M, Torres-Aleman I. Calcineurin in Reactive Astrocytes Plays a Key Role in the Interplay between Proinflammatory and Anti-Inflammatory Signals. The Journal of Neuroscience 2007; 27:8745-8756

Flax, J. D., et al., *Engraftable human neural stem cells respond to developmental cues, replace neurons, and express foreign genes*. Nat Biotechnol. 1998 November; 16(11):1033-9.

Flexman, J. A., et al., *Quantitative analysis of neural stem cell migration and tracer clearance in the rat brain by MRI*. Mol Imaging Biol. 2011 February; 13(1):104-11.

Frank J A, Miller B R, Arbab A S et al. Clinically applicable labeling of mammalian and stem cells by combining superparamagnetic iron oxides and transfection agents. Radiology, 228, 480, 2003.

Frank, R. T.; Edmiston, M.; Kendall, S. E.; Najbauer, J.; Cheung, C.-W.; Kassa, T.; Metz, M. Z.; Kim, S. U.; Glackin, C. A.; Wu, A. M.; Yazaki, P. J.; Aboody, K. S., Neural Stem Cells as a Novel Platform for Tumor-Specific Delivery of Therapeutic Antibodies. *PLoS ONE* 2009, 4 (12), e8314.

Fukui T, Kobayashi H, Hasegawa U, Nagasawa T, Akiyoshi K, Ishikawa I. Intracellular delivery of nanogel-quantum dot hybrid nanoparticles into human periodontal ligament cells. Drug Metab Lett, 2, 131, 2007.

Fukumor Y, Ichikawa H. Nanoparticles for cancer therapy and diagnosis. Adv Poweder Technol. 17: 1-28. 2002.

Fulford, L. G.; Easton, D. F.; Reis-Filho, J. S.; Sofronis, A.; Gillett, C. E.; Lakhani, S. R.; Hanby, A., Specific morphological features predictive for the basal phenotype in grade 3 invasive ductal carcinoma of breast. *Histopathology* 2006, 49 (1), 22-34.

Furnari F B, Fenton T, Bachoo R M, Mukasa A, Stommel J M, Stegh A, Hahn W C, Ligon K L, Louis D N, Brennan C, Chin L, DePinho R A, Cavenee W K. Malignant astrocytic glioma: genetics, biology, and paths to treatment. Genes and Development 2007; 21: 2683-2710.

Gao W, Chan J, Farokhzad O. pH-responsive nanoparticles for drug delivery. Molecular Pharmaceutics. 7:1913-1920. 2010.

Gennet, N., et al., *Microspheres as a vehicle for biomolecule delivery to neural stem cells*. N Biotechnol. 2009 September; 25(6):442-9. Epub 2009 Jun. 11.

Glangchai L, Caldorera-Moore M, Shi L, Roy K. Nanoimprint lithography based fabrication of shape-specific, enzymatically-triggered smart nanoparticles. Journal of Controlled Release. 125: 263-272. 2008

Glass R, Synowitz M, Kronenberg G, Walzlein J H, Markovic D S, Wang L P, Gast D, Kiwit J, Kempermann G K, Kettenmann H. Glioblastoma-Induced Attraction of Endogenous Neural Precursor Cells Is Associated with Improved Survival. The Journal of Neuroscience 2005; 25: 2637-2646.

Grabinski, C.; Schaeublin, N.; Wijaya, A.; D'Couto, H.; Baxamusa, S. H.; Hamad-Schifferli, K.; Hussain, S. M., Effect of gold nanorod surface chemistry on cellular response. *ACS Nano* 2011, 5 (4), 2870-2879.

Greish, K., Enhanced permeability and retention (EPR) effect for anticancer nanomedicine drug targeting. *Methods Mol Biol* 2010, 624, 25-37.

Guichard S, Morton C, Danks M, Potter P. Conversion of the CPT-11 Metabolite APC to SN-38 by Rabbit Liver Carboxylesterase. Clinical Cancer Research. 4: 3089-3094. 1998.

Gullotti E, Yeo Y. Extracellularly activated nanocarriers: a new paradigm of tumor targeted drug delivery. Mol. Pharm. 6: 1041-1051. 2009.

Guo P, Imanishi Y, Cackowski F C, Jarzynka M J, Tao H Q, Nishikawa R, Hirose T, Hu B, Cheng S Y. Up-regulation of angiopoietin-2, matrix metalloprotease-2, membrane type 1 metalloprotease, and laminin 5 gamma 2 correlates with the invasiveness of human glioma. Am J Pathol, 166, 877, 2005.

Gutova, M.; Shackleford, G. M.; Khankaldyyan, V.; Herrmann, K. A.; Shi, X. H.; Mittelholtz, K.; Abramyants, Y.; Blanchard, M. S.; Kim, S. U.; Annala, A. J.; Najbauer, J.; Synold, T. W.; D'Apuzzo, M.; Barish, M. E.; Moats, R. A.; Aboody, K. S., Neural stem cell-mediated CE/CPT-11 enzyme/prodrug therapy in transgenic mouse model of intracerebellar medulloblastoma. *Gene Ther* 2012.

Haiyan C, Yueqing G, Yuzhu H, Zhiyu Q. Characterization of pH- and Temperature-sensitive Hydrogel Nanoparticles for Controlled Drug Release. PDA Journal of Pharmaceutical Science and Technology. 61, 303, 2007.

Hansen, K., et al., *A 3-dimensional extracellular matrix as a delivery system for the transplantation of glioma-targeting neural stem/progenitor cells*. Neuro Oncol. 2010 July; 12(7):645-54. Epub 2010 Feb. 14.

Harrington, K. J.; Rowlinson-Busza, G.; Syrigos, K. N.; Uster, P. S.; Abra, R. M.; Stewart, J. S., Biodistribution and pharmacokinetics of 111 In-DTPA-labelled pegylated liposomes in a human tumour xenograft model: implications for novel targeting strategies. *British journal of cancer* 2000, 83 (2), 232-238.

Hirsch, L. R.; Stafford, R. J.; Bankson, J. A.; Sershen, S. R.; Rivera, B.; Price, R. E.; Hazle, J. D.; Halas, N. J.; West, J. L., Nanoshell-mediated near-infrared thermal therapy of tumors under magnetic resonance guidance. *Proc Natl Acad Sci USA* 2003, 100 (23), 13549-13554.

Holden C A, Yuan Q, Yeudall A W, Lebman D L, Yuang H. Surface engineering of macrophages with nanoparticles to generate a cell-nanoparticle hybrid vehicle for hypoxia-targeted drug delivery. International Journal of Nanomedicine 2010:5 25-36.

Holmberg, A., et al., *The biotin-streptavidin interaction can be reversibly broken using water at elevated temperatures*. Electrophoresis. 2005 February; 26(3):501-10.

Holzapfel, V., et al., *Preparation of Fluorescent Carboxyl and Amino Functionalized Polystyrene Particles by Miniemulsion Polymerization as Markers for Cells*. Macromolecular Chemistry and Physics, 2005. 206(24): p. 2440-2449.

Huang, X.; Jain, P. K.; El-Sayed, I. H.; El-Sayed, M. A., Plasmonic photothermal therapy (PPTT) using gold nanoparticles. *Lasers Med Sci* 2008, 23 (3), 217-228.

Huff, T. B.; Tong, L.; Zhao, Y.; Hansen, M. N.; Cheng, J. X.; Wei, A., Hyperthermic effects of gold nanorods on tumor cells. *Nanomedicine* (Lond) 2007, 2 (1), 125-132.

Ignatova T N, Kukekov V G, Laywell E D, Suslov O N, Vrionis F D, Steindler D A. Human cortical glial tumors contain neural stem-like cells expressing astroglial and neuronal markers in vitro. Glia 2002; 39:193-206.

Ikawa M, Tanaka N, Kwo W W, Verma I. Generation of transgenic mice using lentiviral vectors: a novel preclinical assessment of lentiviral vectors for gene therapy. Molecular Therapy 2003; 4: 666-673.

Iyer A K, Khaled G, Fang J et al. Exploiting the enhanced permeability and retention effect for tumor targeting. Drug Discov Today. 11: 812-818. 2006.

Jackson, J. S., et al., *Homing of stem cells to sites of inflammatory brain injury after intracerebral and intravenous administration: a longitudinal imaging study*. Stem Cell Res Ther. 2010 Jun. 15; 1(2):17.

Jain A, Chasoo G, Singh S, Saxena A K, Jain S K. Transferrin-appended PEGylated nanoparticles for temozolomide. Journal of Microencapsulation, 28, 21, 2011.

Jain, R. K. and T. Stylianopoulos, *Delivering nanomedicine to solid tumors*. Nat Rev Clin Oncol. 2010 November; 7(11):653-64. Epub 2010 Sep. 14.

Jain R. Delivery of molecular and cellular medicine to solid tumors. Adv. Drug Deliv. Rev. 46: 149-168. 2001.

James, W.; Hirsch, L.; West, J.; O'Neal, P.; Payne, J., Application of INAA to the build-up and clearance of gold nanoshells in clinical studies in mice. *Journal of Radioanalytical and Nuclear Chemistry* 2007, 271 (2), 455-459.

Johnson R M, Harrison S D, Maclean D. Therapeutic Applications of Cell-Penetrating Peptides. Cell-Penetrating Peptides: Methods and Protocols, Methods in Molecular Biology, 683: DOI 10.1007/978-1-60761-919-2_38, 2011.

Jolesz, F. A., MRI-guided focused ultrasound surgery. *Annu Rev Med* 2009, 60, 417-430.

Karp, J. M. and G. S. Leng Teo, *Mesenchymal Stem Cell Homing: The Devil Is in the Details*. Cell stem cell, 2009. 4(3): p. 206-216.

Kelly, K. L.; Coronado, E.; Zhao, L. L.; Schatz, G. C., The Optical Properties of Metal Nanoparticles: The Influence of Size, Shape, and Dielectric Environment. *The Journal of Physical Chemistry B* 2002, 107 (3), 668-677.

Kendall, S. E., et al., *Neural Stem Cell Targeting of Glioma Is Dependent on Phosphoinositide 3-Kinase Signaling*. STEM CELLS, 2008. 26(6): p. 1575-1586.

Kim, S. U.; Nakagawa, E.; Hatori, K.; Nagai, A.; Lee, M. A.; Bang, J. H., Production of immortalized human neural crest stem cells. *Methods Mol Biol* 2002, 198, 55-65.

Kim, S. U., Human neural stem cells genetically modified for brain repair in neurological disorders. *Neuropathology* 2004, 24 (3), 159-171.

Kim M, Hwang S, Han J, Choi E, Park H, Kim J, Lee, D. pH-responsive PEG-poly(betaamino ester) block copolymer micelles with a sharp transition. Macromol. Rapid Commun. 27: 447-451. 2006a.

Kim, S.-K.; Kim, S. U.; Park, I. H.; Bang, J. H.; Aboody, K. S.; Wang, K.-C.; Cho, B.-K.; Kim, M.; Menon, L. G.; Black, P. M.; Carroll, R. S., Human Neural Stem Cells Target Experimental Intracranial Medulloblastoma and Deliver a Therapeutic Gene Leading to Tumor Regression. *Clinical Cancer Research* 2006b, 12 (18), 5550-5556.

Kim, S. U., et al., *Production and characterization of immortal human neural stem cell line with multipotent differentiation property*. Methods Mol Biol. 2008; 438: 103-21.

Kim, J. H., et al., *Stereological analysis on migration of human neural stem cells in the brain of rats bearing glioma*. Neurosurgery. 2010 February; 66(2):333-42; discussion 342.

Kim, D.-S., et al., *Highly Pure and Expandable PSA-NCAM-Positive Neural Precursors from Human ESC and iPSC-Derived Neural Rosettes*. 2011. PLoS ONE. 7(7): p. e39715.

King G D, Curtin J F, Candolfi M, Kroeger K, Lowenstein P R, Castro M G. Gene Therapy and Targeted Toxins for Glioma. Current Gene Therapy 2005; 5: 535-557.

Kraitchman D, Heldman A, Atalar E, et al. In vivo magnetic resonance imaging of mesenchymal stem cells in myocardial infarction. Circulation. 10: 2290-2293. 2003.

Krauze, M. T., et al., *Reflux-free cannula for convection-enhanced high-speed delivery of therapeutic agents*. J Neurosurg. 2005 November; 103(5):923-9.

Krishnamachari Y, Pearce M E, Salem A K. Self-assembly of cell-microparticle hybrids. Advanced Biomaterials. 20: 989-993. 2008.

Krishnamachari Y M, Salem A K. Innovative strategies for co-delivering antigens and CpG oligonucleotides. Adv Drug Deliv Rev 2009: 61 205-217.

Krystofiak, E. S., et al., *Elimination of Tumor Cells Using Folate Receptor Targeting by Antibody-Conjugated, Gold-Coated Magnetite Nanoparticles in a Murine Breast Cancer Model*. Journal of Nanomaterials. 2012: p. 9.

Kunwar S. Convection enhanced delivery of the LI13-PE38QQR for treatment of recurrent malignant glioma: presentation of interim findings from ongoing phase 1 studies. Acta Neurochir Suppl 2003; 88: 105-111.

Kvols L K. Radiation Sensitizers: A Selective Review of Molecules Targeting DNA and non-DNA Targets. Journal of Nuclear Medicine, 46: 187s, 2005.

Laske D W, Youle R J, Oldfeild E H. Tumor regression with regional distribution of the targeted toxin TF-CRM107 in patients with malignant brain tumors. Nature Medicine 1997; 3: 1362-1368.

Levin, V. A., J. D. Fenstermacher, and C. S. Patlak, *Sucrose and inulin space measurements of cerebral cortex in four mammalian species*. Am J Physiol. 1970 November; 219(5):1528-33.

Li, L.; Guan, Y.; Liu, H.; Hao, N.; Liu, T.; Meng, X.; Fu, C.; Li, Y.; Qu, Q.; Zhang, Y.; Ji, S.; Chen, L.; Chen, D.; Tang, F., Silica nanorattle-doxorubicin-anchored mesenchymal stem cells for tumor-tropic therapy. ACS Nano 2011, 5 (9), 7462-7470.

Lin, D., et al., *Novel method for visualizing and modeling the spatial distribution of neural stem cells within intracranial glioma*. Neuroimage. 2007; 37 Suppl 1:S18-26. Epub 2007 May 13.

Link, S.; El-Sayed, M. A., Spectral Properties and Relaxation Dynamics of Surface Plasmon Electronic Oscillations in Gold and Silver Nanodots and Nanorods. *The Journal of Physical Chemistry B* 1999, 103 (40), 8410-8426.

Liu, Y.; Shipton, M. K.; Ryan, J.; Kaufman, E. D.; Franzen, S.; Feldheim, D. L., Synthesis, stability, and cellular internalization of gold nanoparticles containing mixed peptide-poly(ethylene glycol) monolayers. *Anal Chem* 2007, 79 (6), 2221-2229.

Lorenz, M. R., et al., *Synthesis of fluorescent polyisoprene nanoparticles and their uptake into various cells*. Macromol Biosci. 2008 Aug. 11; 8(8):711-27.

Lorenz, M. R., et al., *Uptake of functionalized, fluorescent-labeled polymeric particles in different cell lines and stem cells*. Biomaterials. 2006 May; 27(14):2820-8. Epub 2006 Jan. 23.

Love Z, Wang F, Dennis J et al. Imaging of mesenchymal stem cell transplant by bioluminiescence and PET. J Nucl Med. 48: 2011-2020. 2007.

MacEwan S, Callahan D, Chilkoti A. Stimulus-Responsive Macromolecules and Nanoparticles for Cancer Drug Delivery: Nanomedicine. 5:793-806. 2010.

MacKay, J. A., D. F. Deen, and F. C. Szoka Jr, *Distribution in brain of liposomes after convection enhanced delivery; modulation by particle charge, particle diameter, and presence of steric coating*. Brain Research, 2005. 1035(2): p. 139-153.

MacLauren D C, Toyokuni T, Cherry S R et al. PET imaging of transgene expression. Biol Psychiatry. 48: 337-348. 2000.

Mailander, V. and K. Landfester, *Interaction of Nanoparticles with Cells*. Biomacromolecules, 2009. 10(9): p. 2379-2400.

Malugin, A.; Ghandehari, H., Cellular uptake and toxicity of gold nanoparticles in prostate cancer cells: a comparative study of rods and spheres. *J Appl Toxicol* 2010, 30 (3), 212-217.

Marumoto T, Freidmann-Morvinski D, Yang M, Hoffman R, Inder V. Novel mouse glioma model: cell-type and region specific activation of oncogenes using lentiviral vectors. Nature Protocols 2008; DOI: 10.1038/nprot.2008.207.

Mayer-Proschel M, Kalyani A J, Mujtaba T, Rao M S. Isolation of lineage-restricted neuronal precursors from multipotent neuroepithelial stem cells. Neuron 1997; 19: 773-785.

Meikle, S. R., et al., *Pharmacokinetic assessment of novel anti-cancer drugs using spectral analysis and positron emission tomography: A feasibility study*. Cancer Chemotherapy and Pharmacology, 1998. 42(3): p. 183-193.

Meyer, D. L., et al., *Reduced antibody response to streptavidin through site-directed mutagenesis*. Protein Sci. 2001 March; 10(3):491-503.

Mirza, A. N.; Fornage, B. D.; Sneige, N.; Kuerer, H. M.; Newman, L. A.; Ames, F. C.; Singletary, S. E., Radiofrequency ablation of solid tumors. *Cancer J* 2001, 7 (2), 95-102.

Moon J, Lee S, West J. Synthetic Biomimetic Hydrogels Incorporated with Ephrin-A1 for Therapeutic Angiogenesis. Biomacromolecules. 8: 42-49. 2007.

Muller F J, Snyder E Y, Loring J F. Gene therapy: can neural stem cells deliver? Nature Reviews 2006; 7: 75-84.

Murphy, C. J.; Sau, T. K.; Gole, A. M.; Orendorff, C. J.; Gao, J.; Gou, L.; Hunyadi, S. E.; Li, T., Anisotropic metal nanoparticles: Synthesis, assembly, and optical applications. *J Phys Chem B* 2005, 109 (29), 13857-13870.

Neeves, K. B., et al., *Dilation and degradation of the brain extracellular matrix enhances penetration of infused polymer nanoparticles*. Brain Res. 2007 Nov. 14; 1180: 121-32. Epub 2007 Aug. 29.

Neuberger T, Schopf B, Hofmann H et al. Superparamagnetic nanoparticles for biomedical applications: Possibilities and limitations of a new drug delivery system. J Magn Magn Mater. 293: 483-496. 2005.

Niidome, T.; Yamagata, M.; Okamoto, Y.; Akiyama, Y.; Takahashi, H.; Kawano, T.; Katayama, Y.; Niidome, Y., PEG-modified gold nanorods with a stealth character for in vivo applications. *J Control Release* 2006, 114 (3), 343-347.

Niidome, Y.; Honda, K.; Higashimoto, K.; Kawazumi, H.; Yamada, S.; Nakashima, N.; Sasaki, Y.; Ishida, Y.; Kikuchi, J., Surface modification of gold nanorods with synthetic cationic lipids. *Chem Commun* (Camb) 2007, (36), 3777-3779.

Paciotti, G. F.; Kingston, D. G. I.; Tamarkin, L., Colloidal gold nanoparticles: a novel nanoparticle platform for developing multifunctional tumor-targeted drug delivery vectors. *Drug Development Research* 2006, 67 (1), 47-54.

Panyam J, Labhasetwar V. Biodegradable nanoparticles for drug and gene delivery to cells and tissue. Adv Drug Deliv Rev 2003; 55: 329-47.

Pardridge W M. Blood-Brain Barrier Drug Targeting Enables Neuroprotection in Brain Ischemia Following Delayed Intravenous Administration of Neurotrophins adame Curie Bioscience Database Austin (Tex.): Landes Bioscience; 2000-2011, Landes Bioscience and Springer Science+Business Media.

Parkin D M, Bray F, Ferlay J, Pisani P. Global cancer statistics. Cancer Journal for Clinicians 2002; 55:74-108.

Patil R, Portilla-Arias J, Ding H, Inoue S, Konda B, Hu J, Wawrowsky K A, Shin P K, Black K L, Holler E, Ljubimova J Y. Temozolomide Delivery to Tumor Cells by a Multifunctional Nano Vehicle Based on Poly($\beta$-L-malic acid). Pharm Res, 11, 2317, 2010.

Peer, D.; Karp, J. M.; Hong, S.; Farokhzad, O. C.; Margalit, R.; Langer, R., Nanocarriers as an emerging platform for cancer therapy. *Nat Nano* 2007, 2 (12), 751-760.

Penas-Prado M, Glibert M R. Moleculary targeted therapies for malignant gliomas: advances and challenges. Expert Review of Anti-Cancer Therapy 2007; 7: 641-661.

Peppas N, Lang Z. Physiochemical Foundations and Structural Design of Hydrogels in Medicine and Biology. Annu. Rev. Biomed. Eng. 2:9-29. 2000.

Perlstein, B., et al., *Convection-enhanced delivery of maghemite nanoparticles: Increased efficacy and MRI monitoring.* Neuro Oncol. 2008 April; 10(2):153-61. Epub 2008 Mar. 3.

Petersen, M. A. and M. E. Dailey, *Diverse microglial motility behaviors during clearance of dead cells in hippocampal slices.* Glia. 2004 Apr. 15; 46(2):195-206.

Pfenninger C V, Roschupkina T, Hertwig F, Kottwitz D, Englund E, Bengzon J, Jacobsen S E, Nuber UA. CD133 Is Not Present on Neurogenic Astrocytes in the Adult Subventricular Zone, but on Embryonic Neural Stem Cells, Ependymal Cells, and Glioblastoma Cells. Cancer Research 2007; 6: 5727-5736.

Philipp, C. M.; Rohde, E.; Berlien, H. P., Nd:YAG laser procedures in tumor treatment. *Semin Surg Oncol* 1995, 11 (4), 290-298.

Pollenzi A, Ailles L E, Bakovic S, Geuna M, Naldini L. Gene transfer by lentiviral vectors is limited by nuclear translocation and rescued by HIV-1 pol sequences. Nature Genetics 2000; 25: 217-222.

Prayson R. Cyclooxygenase-2 (COX-2) expression by immunohistochemistry in glioblastoma multiforme. Annals of Diagnostic Pathology 2002; 6: 148-153.

Prescher J A, Dube D H, Bertozzi C R. Chemical remodeling of cell surfaces in living animals. Nature 2004; 430: 873-877.

Prudhomme, M.; Tang, J.; Rouy, S.; Delacretaz, G.; Salathe, R. P.; Godlewski, G., Interstitial diode laser hyperthermia in the treatment of subcutaneous tumor. *Lasers Surg Med* 1996, 19 (4), 445-450.

Rebner, K., et al., *Dark-field scattering microscopy for spectral characterization of polystyrene aggregates.* Opt Express. 2010 Feb. 1; 18(3):3116-27. doi: 10.1364/OE.18.003116.

Rejman, J., et al., *Size-dependent internalization of particles via the pathways of clathrin- and caveolae-mediated endocytosis.* Biochem J. 2004 Jan. 1; 377(Pt 1):159-69.

Roger, M.; Clavreul, A.; Venier-Julienne, M. C.; Passirani, C.; Sindji, L.; Schiller, P.; Montero-Menei, C.; Menei, P., Mesenchymal stem cells as cellular vehicles for delivery of nanoparticles to brain tumors. *Biomaterials* 2010, 31 (32), 8393-8401.

Saito R, Bringas J R, Panner A, Tamas M, Pieper R O, Berger M S, Bankiewicz. Convection-enhanced delivery of tumor necrosis factor-related apoptosis-inducing ligand with systemic administration of temozolomide prolongs survival in an intracranial glioblastoma xenograft model. Cancer Research 2004; 64: 6858-6862.

Salem A K. (Iowa City, Iowa, US), Krishnamachari, Yogita (Iowa City, Iowa, US) 2010 Self-Assembly of a Cell-Microparticle Hybrid. United States. The University of Iowa Research Foundation. 20100190257. http://www-.freepatentsonline.com/y2010/0190257.html Sampson J H, Akabani G, Archer G E, Bigner D D, Berger M S, Friedman A H, Friedman H S, Herndon J E, Kunwar S, Marcus S, McLendon R E, Paolino A, Penne K, Provenzale J, Quinn J, Reardon D A, Rich J, Stenzel T, Tourt-Uhlig S, Wikstrand C, Wong T, Williams R, Yuan F, Zalutsky M R, Pastan I. Progress report of a Phase I study of the intracerebral microinfusion of a recombinant chimeric protein composed of transforming growth factor alpha and a mutated form of the pseudomonas exotoxin termed PE-38 for the treatment of malignant brain tumors. J Neurooncol 2003; 65: 27-35.

Sanai N, Alvarez-Buylla A, Berger M S. Neural stem cells and the origins of gliomas. New England Journal of Medicine 2005; 353:811-822.

Sawhney A S, Pathak C P, Hubbell J A. Bioerodable hydrogels based on photopolymerized poly (ethylene glycol)-co-poly(alpha-hydroxy acid)diacryalte macromers. Macromolecules, 26: 581-587. 1993.

Schafer R, Kehlbach R, Muller M et al. Labeling of human mesenchymal stromal cells with superparamagnetic iron oxide leads to a decrease in migration capacity and colony formation ability. Cytotherapy. 11:68-78. 2009.

Schafer R, Kehlbach R, Wiskirchen J et al. Transferrin receptor upregulation: In vitro labeling of rat mesenchymal stem cells with superparamagnetic iron oxide. Radiology. 244: 514-523. 2007.

Schluep T, Hwang J, Hildebrandt I, Czernin J, Choic H, Alabi C, Mack C, Davis M. Pharmacokinetics and tumor dynamics of the nanoparticle IT-101 from PET imaging and tumor histological measurements. Proc Natl Acad Sci. 106: 11394-11399. 2009.

Schmidt N O, Przylecki W, Yang W, Ziu M, Teng Y, Kim S U, Black P M, Aboody K S, Carroll R S. Brain tumor tropism of transplanted human neural stem cells is induced by vascular endothelial growth factor. Neoplasia 2005: 7:623-629.

Seki, T.; Wakabayashi, M.; Nakagawa, T.; Imamura, M.; Tamai, T.; Nishimura, A.; Yamashiki, N.; Okamura, A.; Inoue, K., Percutaneous microwave coagulation therapy for patients with small hepatocellular carcinoma: comparison with percutaneous ethanol injection therapy. *Cancer* 1999, 85 (8), 1694-1702.

Seneterre, E. Taourel, P., Bouvier, Y., et al. Detection of hepatic metastases: Ferumoxides-enhanced MR imaging versus unenhanced MR imaging and CT during arterial portography. Radiology, 200, 785, 1996.

Shubayev V I, Pisanic T R, Jin S. Magnetic nanoparticles for theragnostics. Adv Drug Del iv Rev. 61:467-477. 2009.

Singh J P. Enabling Technologies for Homing and Engraftment of Cells for Therapeutic Applications. J Am Coll Cardiol Intv, 2, 803, 2009.

Singh S K, Hawkins C, Clarke I D, Squire J A, Bayani J, Hide T, Henkelman R M, Cusimano M D, Dirks P B. Identification of brain tumor initiating cells. Nature 2004; 432: 396-401.

Soderquist R, Sloane E, Loram L, Harrison J, Dengler E, Johnson S, Amer L, Young C, Lewis M, Poole S, Frank M, Watkins L, Milligan E, Mahoney M. Release of Plasmid DNA-Encoding IL-10 from PLGA Microparticles Facilitates Long-Term Reversal of Neuropathic Pain Following a Single Intrathecal Administration. Pharmaceutical Research. 27: 841-854. 2010.

Srinivas, L. and N. H. Colburn, *Preferential oxidation of cell surface sialic acid by periodate leads to promotion of transformation in J86 cells*. Carcinogenesis. 1984 April; 5(4):515-9.

Stephan M T, Moon J J, Um S H, Bershteyn A, Irvine D J. Therapeutic cell engineering with surface-conjugated synthetic nanoparticles. Nature Medicine 2010:16:1035-1041.

Stephan, M. T. and D. J. Irvine, *Enhancing Cell therapies from the Outside In: Cell Surface Engineering Using Synthetic Nanomaterials*. Nano Today. 2011 Jun. 1; 6(3): 309-325.

Stuart C McBain, Humphrey HPY, Dobson J. Magnetic nanoparticles for gene and drug delivery. Int J Nanomedicine. 3, 169, 2008.

Stupp R, Mason W P, Van den Bent M J, Weller M, Fisher B, Taphoorn M J, Belanger K, Brandes A A, Marosi C, Bogdahn U, Curschmann J, Janzer R C, Ludwin S K, Gorlia T, Allgeier A, Lacombe D, Cairncross J G, Eisenhauer E, Mirimanoff R O. Radiotherapy plus concomitant and adjuvant temozolomide for glioblastoma. New England Journal of Medicine 2005; 352: 987-996.

Sykov, E. and C. Nicholson, *Diffusion in Brain Extracellular Space*. Physiological Reviews, 2008. 88(4): p. 1277-1340.

Tang C, Russell P J, Martiniello-Wilks R, Rasko J, Khatri A. Concise Review: Nanoparticles and Cellular Carriers-Allies in cancer Imaging and Cellular Gene Therapy? Stem Cells: Translational and Clinical Research. 28: 1686-1702. 2010.

Tang, Y., et al., *In vivo tracking of neural progenitor cell migration to glioblastomas*. Hum Gene Ther. 2003 Sep. 1; 14(13):1247-54.

Thu M, Najbauer J, Kendall S, Harutyunyan I, Sangalang N, Gutova M, Metz M, Garcia E, Frank R, Kim S, Moats R, Aboody K. Iron Labeling and Pre-Clinical MRI Visualization of Therapeutic Human Neural Stem Cells in a Murine Glioma Model. 4: e7218. 2009

Tong, L.; Zhao, Y.; Huff, T. B.; Hansen, M. N.; Wei, A.; Cheng, J. X., Gold Nanorods Mediate Tumor Cell Death by Compromising Membrane Integrity. *Adv Mater* 2007, 19, 3136-3141.

van der Zee, J., Heating the patient: a promising approach? *Ann Oncol* 2002, 13 (8), 1173-1184.

Vaupel P. Tumor Microenvironmental Physiology and Its Implications for Radiation. Oncology Semin. Radiat. Oncol. 14: 198-206. 2004.

Vavra M, Ali M J, Kang E W, Navalitloha Y, Ebert A, Allen C V, Groothuis D R. Comparative pharmacokinetics of 14C-sucrose in RG-2 rat gliomas after intravenous and convection-enhanced delivery. Neuro-oncology 2004; 6:104-112.

Verma, A. and F. Stellacci, *Effect of surface properties on nanoparticle-cell interactions*. Small. 2010 January; 6(1): 12-21.

von Maltzahn, G.; Park, J.-H.; Agrawal, A.; Bandaru, N. K.; Das, S. K.; Sailor, M. J.; Bhatia, S. N., Computationally Guided Photothermal Tumor Therapy Using Long-Circulating Gold Nanorod Antennas. *Cancer Research* 2009, 69 (9), 3892-3900.

Wang Y M, Lin K T, Chen T J, Liu G C. Folate-receptor-targeting iron oxide nanoparticles coated with poly(ethylene glycol). United States Kaohsiung Medical University 7598335 http://www.freepatentsonline.com/7598335.html, 2009.

Weber F W, Floeth F, Asher A, Bucholz R, Berger M, Prados M, Chang S, Bruce J, Hall W, Rainov N G, Westphal M, Warnnick R E, Rand R W, Rommell F, Pan H, Hingorani V N, Puri R K. Local convection enhanced delivery of IL4-pseudomonas exotoxin for treatment of patients with recurrent malignant glioma. Acta Neurochir. Suppl 2003; 88: 93-103.

Weissleder R, Ntziachristos V. Shedding light onto live molecular targets. Nature Medicine 2003; 9:123-128.

Wen P Y, Kesari S. Malignant gliomas in adults. New England Journal of Medicine 2008; 359:492-507.

Wu Y, Xing D, Chen Q, Tang Y. Imaging of activated caspase-3 in living cell by fluorescence resonance energy transfer during photosensitization-induced apoptosis. SPIE 5630, 376. 2005.

Xing Y, Rao J, Quantumdot bioconjugates for in vitro diagnostics&in vivo imaging. Cancer Biomarkers 4, 307, 2008.

Yang, J., et al., *Tumor tropism of intravenously injected human-induced pluripotent stem cell-derived neural stem cells and their gene therapy application in a metastatic breast cancer model*. Stem Cells. 2012 May; 30(5):1021-9. doi: 10.1002/stem.1051.

Yesavage J. A. et al. Donepezil and flight simulator performance: Effects on retention of complex skills. Neurology, 59, 123, 2002.

Yu J S, Ehtesham M. Neural Stem Cells as Therapeutic Vehicles to Treat Malignant Glioma. Cedars-Sinai 2008; 6107:1-8.

Zhang Y, Zhang H, Liu J, Yue Z. Temozolomide/PLGA microparticles: a new protocol for treatment of glioma in rats. Med Oncol. DOI 10.1007/s12032-010-9531-2. 2010.

Zhang, J., et al., *Endogenously EGFP-Labeled Mouse Embryonic Stem Cells*. Aging Dis. 2011 February; 2(1): 18-29.

Zhao, D.; Najbauer, J.; Annala, A. J.; Garcia, E.; Metz, M. Z.; Gutova, M.; Polewski, M. D.; Gilchrist, M.; Glackin, C. A.; Kim, S. U.; Aboody, K. S., Human neural stem cell tropism to metastatic breast cancer. *Stem Cells* 2012, 30 (2), 314-325.

Zhao, D.; Najbauer, J.; Garcia, E.; Metz, M. Z.; Gutova, M.; Glackin, C. A.; Kim, S. U.; Aboody, K. S., Neural stem cell tropism to glioma: critical role of tumor hypoxia. Mol Cancer Res 2008, 6 (12), 1819-1829.

Ziu, M., et al., *Glioma-produced extracellular matrix influences brain tumor tropism of human neural stem cells*. J Neurooncol. 2006 September; 79(2):125-33. Epub 2006 Apr. 6.

What is claimed is:

1. A therapeutic delivery vehicle comprising a gold particle coated with a cationic thiol moiety internalized by a genetically modified neural stem cell, wherein the cationic thiol moiety is 11-mercaptoundecyltrimethylammonium bromide.

2. The therapeutic delivery vehicle of claim 1, wherein the genetically modified neural stem cell is an immortalized neural stem cell.

3. The therapeutic delivery vehicle of claim 1, wherein the genetically modified neural stem cell expresses cytosine deaminase, v-myc, or both cytosine deaminase and v-myc.

4. The therapeutic delivery vehicle of claim 1, wherein the gold particle is a gold nanorod.

5. The therapeutic delivery vehicle of claim 1, wherein the average longest dimension of the gold particle is about 41 nm.

6. The therapeutic delivery vehicle of claim 1, wherein the gold particle is about 10 nm by about 41 nm.

* * * * *